(12) United States Patent
Gao

(10) Patent No.: US 6,429,191 B1
(45) Date of Patent: *Aug. 6, 2002

(54) TREATMENT OF HEARING IMPAIRMENTS

(75) Inventor: Wei-Qiang Gao, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/823,717

(22) Filed: Mar. 30, 2001

Related U.S. Application Data

(63) Continuation of application No. 08/778,357, filed on Jan. 2, 1997, now Pat. No. 6,225,282.
(60) Provisional application No. 60/044,407, filed on Jan. 5, 1996, now abandoned.

(51) Int. Cl.$^7$ .......................... A61K 38/00; A61K 31/43

(52) U.S. Cl. ............................. 514/2; 514/12; 514/192; 514/198; 514/199

(58) Field of Search ............................. 514/2, 12, 192, 514/198, 199

(56) References Cited

FOREIGN PATENT DOCUMENTS

WO          WO 95/30434          11/1995

OTHER PUBLICATIONS

Anniko et al., "Cisplatin: Evaluation of its Ototoxic Potential," *Am. J. Otolaryngol.*, 7:276–293 (1986).
Apfel et al., "Nerve Growth Factor Prevents Toxic Neuropathy in Mice," *Annals of Neurology*, 29(1): 87–90 (Jan. 1991).
Ard et al., "Trophic Interactions Between the Cochleovestibular Ganglion of the Chick Embryo and its Synaptic Targets in Culture," *Neuroscience*, 16(1):151–170 (1985).
Au et al., "Aminoglycoside Antibiotics Preferentially Increase Permeability in Phosphoinositide–containing Membranes: a Study with Carboxyfluorescein in Liposomes," *Biochimica et Biophysica Acta*, 902:80–86 (1987).
Baird et al., "Cerebellar Target Neurons Provide a Stop Signal for Afferent Neurite Extension in vitro," *The Journal of Neuroscience*, 12(2):619–634 (Feb. 1992).
Barbacid, "The Trk Family of Neurotrophin Receptors: Molecular Characterization and Oncogenic Activation in Human Tumors," *Molecular Genetics of Nervous System Tumors*, pp. 123–136 (1993).
Barde et al., "Purification of a New Neurotrophic Factor From Mammalian Brain," *EMBO Journal*, 1(5):549–553 (1982).
Bareggi et al., "Gentamicin Ototoxicity: Histological and Ultrastructural Alterations After Transtympanic Administration," *Pharmacological Research*, 22(5):635–644 (1990).

Barker et al., "Disruption of NGF Binding to the Low Affinity Neurotrophin Receptor p75$^{LNTR}$ Reduces NGF Binding to TrkA on PC12 Cells," *Neuron*, 13:203–215 (1994).
Berggren et al., "Intermediate Filament Proteins in the Embryonic Inner Ear of Mice Under Normal Conditions and After Exposure to Ototoxic Drugs," *Acta Otolaryngol*, 109:57–65 (1990).
Berkemeier et al., "Neurotrophin–5: A Novel Neurotrophic Factor That Activates trk and trkB," *Neuron*, 7:857–866 (Nov. 1991).
Boettcher et al., "Concentration of Salicylate in Serum and Perilymph of the Chinchilla," *Arch. Otolaryngol Head Neck Surg.*, 116:681–684 (1990).
Boettcher et al., "Effects of Sodium Salicylate on Evoked–response Measures of Hearing," *Hearing Research*, 42:129–142 (1989).
Boettcher et al., "Salicylate Ototoxicity: Review and Synthesis," *Am. J. Otoloaryngol.*, 12:33–47 (1991).
Carenza et al.,"Peripheral Neuropathy and Ototoxicity of Diclorodiamineplatinum: Instrumental Evaluation," *Gynecologic Oncology*, 25:244–249 (1986).
Chao, "Gene Transfer and Molecular Cloning of the Human NGF Receptor," *Science*, 232:518–521 (1986).
Chao, "Growth Factor Signaling: Where is the Specificity!," *Cell*, 68:995–997 (Mar. 20, 1992).
Cheng, Alan G. et al., "Calpain inhibitors protect auditory sensory cells from hypoxia and neurotrophin–withdrawal induced apoptosis," *Brain Research*, vol. 850, pp. 234–243 (1999).
Clary et al., "An Alternatively Spliced Form of the Nerve Growth Factor Receptor TrkA Confers an Enhanced Response to Neurotrophin 3," *Proc. Natl. Acad. Sci, USA*, 91:11133–11137 (1994).
Clary et al.,"TrkA Cross–linking Mimics Neuronal Responses to Nerve Growth Factor," *Molecular Biology of the Cell*, 5:549–563 (1994).
Cohen et al., "Neurotrophin–4/5 (NT–4/5) Increases Adult Rat Retinal Ganglion Cell Survival and Neurite Outgrowth in vitro," *Journal of Neurobiology*, 25(8):953–959 (1994).
Cordon–Cardo et al., "The trk Tyrosine Protein Kinase Mediates the Mitogenic Properties of Nerve Growth Factor and Neurotrophin–3," *Cell*, 66:173–183 (Jul. 12, 1991).

(List continued on next page.)

Primary Examiner—Zohreh Fay
(74) Attorney, Agent, or Firm—Knobbe Martens Olson & Bear LLP

(57) ABSTRACT

Compositions and methods are provided for prophylactic or therapeutic treatment of a mammal for hearing impairments involving neuronal damage, loss, or degeneration, preferably of spinal ganglion neurons, by administration of a therapeutically effective amount of a trkB or trkC agonist, particularly a neurotrophin, more preferably NT-4/5. Also provided are improved compositions and methods for treatments requiring administration of a pharmaceutical having an ototoxic side-effect, wherein the improvement includes administering a therapeutically effective amount of a trkB or trkC agonist to treat the ototoxicity.

38 Claims, 10 Drawing Sheets

OTHER PUBLICATIONS

Corwin et al., "Auditory Hair Cells: Structure, Function, Development, and Regeneration," *Annu. Rev. Neuroscience*, 14:301–333 (1991).

Cotanche et al., "Regeneration of Hair Cells in the Vestibulocochlear System of Birds and Mammals," *Current Opinion in Neurobiology*, 4:509–514 (1994).

Davies et al., "Different Factors From the Central Nervous System and Periphery Regulate the Survival of Sensory Neurones," *Nature*, 319:497–499 (1986).

Davies et al., "p75–Deficient Trigeminal Sensory Neurons Have an Altered Response to NGF but Not to Other Neurotrophins," *Neuron*, 11:565–574 (Oct. 1993).

Davies et al., "Neurotrophin–4/5 is a Mammalian–specific Survival Factor for Distinct Populations of Sensory Neurons," *J. Neuroscience*, 13(11):4961–4967 (Nov. 1993).

De Moura, "Inner Ear Pathology in Acoustic Neurinoma," *Arch. Otolaryng.*, 85:21–29 (125–133) (Feb. 1967).

Dublin, W., "Anatomic Principles With Some Functional and General Pathologic Applications," *Fundamentals of Sensorineural Auditory Pathology*, (Chapter 3), Springfield, Illinois: Charles C. Thomas pp. 18–103 (1976).

Duckert et al., "Morphological Correlates of Functional Recovery in the Chicken Inner Ear After Gentamycin Treatment," *The Journal of Comparitive Neurology*, 331:75–96 (1993).

Ernfors et al., "Function of the Neurotrophins in the Auditory and Vestibular Systems: Analysis of BDNF and NT–3 Gene Knockout Mice," *ARO Abstracts*, (Abstract 759) p. 190 (1995).

Ernfors et al., "Mice Lacking Brain–derived Neurotrophic Factor Develop with Sensory Deficits," *Nature*, 368:147–150 (Mar. 10, 1994).

Ernfors et al., "Molecular Cloning and Neurotrophic Activities of a Protein With Structural Similarities to Nerve Growth Factor: Developmental and Topographical Expression in the Brain," *Proc. Natl., Acad. Sci. USA*, 87:5454–5458 (Jul. 1990).

Escandon et al., "Regulation of Neurotrophin Receptor Expression During Embryonic and Postnatal Development," *The Journal of Neuroscience*, 14(4):2054–2068 (Apr. 1994).

Farinas et al., "Severe Sensory and Sympathetic Deficits in Mice Lacking Neurotrophin–3," *Nature*, 369:658–661 (Jun. 23, 1994).

Fischer et al., "Reversal of Spatial Memory Impairments in Aged Rats by Nerve Growth Factor and Neurotrophins 3 and 4/5 but not by Brain–Derived Neurotrophic Factor," *Proc. Natl. Acad. Sci. USA*, 91:8607–8611 (Aug. 1994).

Furley et al., "The Axonal Glycoprotein TAG–1 is an Immunoglobulin Superfamily Member the Neurite Outgrowth–Promoting Activity," *Cell*, 61:157–170 (Apr. 6, 1990).

Gao et al., "Cerebellar Granule Cell Neurogenesis is Regulated by Cell–Cell Interactions in Vitro," *Neuron*, 6:705–715 (May 1991).

Gao et al., "Neurotrophin–4/5 (NT–4/5) and Brain–Derived Neurotrophic Factor (BDNF) Act at Later Stages of Cerebellar Granule Cell Differentiation," *The Journal of Neuroscience*, 15(4):2656–2667 (Apr. 1995).

Gao et al., "Neurotrophin–3 Reverses Experimental Cisplatin–induced Peripheral Sensory Neuropathy," *Annals of Neurology*, 38(1):30–37 (Jul. 1995).

Garner et al., "Isoforms of the Avian TrkC Receptor: A Novel Kinase Insertion Dissociates Transformation and Process Outgrowth From Survival," *Neuron*, 13:457–472 (Aug. 1994).

Gotz et al., "Neurotrophin–6 is a New Member of the Nerve Growth Factor Family," *Nature*, 372:266–269 (1994).

Gotz et al., "Production and Characterization of Recombinant Mouse Neurotrophin–3," *European Journal of Biochemistry*, 204:745–749 (1992).

Guild et al., "Correlations of Differences in the Density of Innervation of the Organ of Corti With Differences in the Acuity of Hearing, Including Evidence as to the Location in the Human Cochlea of the Receptors for Certain Tones," *Acta Oto–Laryngologica*, Holmgren vol. XV:269–308 (1931).

Hefti, Franz, "Nerve Growth Factor promotes Survival of Septal Cholinergic Neurons After Fimbrial Transections," *J. of Neuroscience*, 6(8):2155–2162 (Aug. 1986).

Hinojosa, "Cochlear Neural Degeneration Without Hair Cell Loss in Two Patients With Aminoglycoside Ototoxicity," *The Journal of Infectious Diseases*, 156(3):449–455 (1987).

Hohn et al., "Identification and Characterization of a Novel Member of the Nerve Growth Factor/Brain–derived Neurotrophic Factor Family," *Nature*, 344–339–341 (Mar. 22, 1990).

Hood et al., "Contemporary Applications of Neurobiology in Human Hearing Assessment," *Neurobiology of Hearing: The Cochlea*, Altschuler et al., New York:Raven Press pp. 397–423 (1986).

Hyman et al., "BDNF is a Neurotrophic Factor for Dopaminergic Neurons of the Substantia Nigra," *Nature*, 350:230–233 (Mar. 21, 1991).

Ip et al., "Mammalian Neurotrophin–4: Structure, Chromosomal Localization, Tissue Distribution, and Receptor Specificity," *Proc. Natl. Acad. Sci. USA*, 89:3060–3064 (Apr. 1992).

Ip et al., "Similarities and Differences in the Way Neurotrophins Interact With the Trk Receptors in Neuronal and Nonneuronal Cells," *Neuron*, 10:137–149 (Feb. 1993).

Jarvis, J., "A Case of Unilateral Permanent Deafness Following Acetylsalicylic Acid," *J. Laryngology and Otology*, 80(3):318–320 (Mar. 1966).

Jones et al., "Molecular Cloning of a Human Gene That is a Member of the Nerve Growth Factor Family," *Proc. Natl. Acad. Sci. USA*, 87:8060–8064 (1990).

Kaplan et al., "The trk Proto–Oncogene Product: A Signal Transducing Receptor for Nerve Growth Factor," *Science*, 252:554–558 (Apr. 26, 1991).

Kaplan et al., "Tyrosine Phosphorylation and Tyrosine Kinase Activity of the trk Proto–oncogene Product Induced by NGF," *Nature*, 350:158–160 (Mar. 14, 1991).

Kelley et al., "The Development Organ of Corti Contains Retinoic Acid and Forms Supernumerary Hair Cells in Response to Exogenous Retinoic Acid in Culture," *Development*, 119:1041–1053 (1993).

Klein et al., "Expression of the Tyrosine Kinase Receptor Gene trkB is Confined to the Murine Embryonic and Adult Nervous System," *Development*, 109:845–850 (1990).

Klein et al., "The trk Proto–Oncogene Encodes a Receptor for Nerve Growth Factor," *Cell*, 65:189–197 (Apr. 5, 1991).

Klein et al., "The trkB Tyrosine Protein Kinase is a Receptor for Neurotrophin–4," *Neuron*, 8:947–956 (May 1992).

Klein et al., "The trkB Tyrosine Protein Kinase is a Receptor for Brain–Derived Neurotrophic Factor and Neurotrophin–3," *Cell*, 66:395–403 (Jul. 26, 1991).

Klein et al., "trkB, A Novel Tyrosine Protein Kinase Receptor Expressed During Mouse Neural Development," *EMBO Journal*, 8(12):3701–3709 (1989).

Knusel et al., "Brain–derived Neurotrophic Factor Administration Protects Basal Forebrain Cholinergic but Not Nigral Dopaminergic Neurons from Degenerative Changes After Axotomy in the Adult Rat Brain," *The Journal of Neuroscience*, 12(11):4391–4402 (Nov. 1992).

Koliatsos et al., "Evidence that Brain–Derived Neurotrophic Factor is a Trophic Factor for Mottor Neurons in vivo," *Neuron*, 10:359–367 (Mar. 1993).

Konings et al., "Reversal by NGF of Cytostatic Drug–induced Reduction of Neurite Outgrowth in Rat Dorsal Root Ganglia in vitro," *Brain Research*, 640:195–204 (1994).

Kopf–Maier et al., "Changes in the Cytoskeleton Pattern of Tumor Cells by Cisplatin in vitro," *Chem–Biol. Interactions*, 82:295–316 (1992).

Korsching, "The Neurotrophic Factor Concept: A Reexamination," *The Journal of Neuroscience*, 13(7):2739–2748 (1993).

Lamballe et al., "trkC, a New Member of the trk Family of Tyrosine Protein Kinases, is a Receptor for Neurotrophin–3," *Cell*, 66:967–979 (Sep. 6, 1991).

Lambert, P., "Inner Ear Hair Cell Regeneration in a Mammal: Identification of a Triggering Factor," *Laryngoscope*, 104:701–718 (Jun. 1994).

Larkfors et al., "Efects of Neurotrophins on Rat Embryonic Cerebellar Purkinje Cells in vitro," *Society for Neuroscience Abstracts*, (Abstract 278.14) 19 (Part 1):667 (1993).

Leake et al., "Chronic Intracochlear Electrical Stimulation in Neonatally Deafened Cats: Effects of Intensity and Stimulating Electrode Location," *Hearing Research*, 64:99–117 (1992).

Lefebvre et al., "Neurtrophins Affect Survival and Neuritogenesis by Adult Injured Auditory Neurons in vitro," *NeuroReport*, 5(8):865–868 (1994).

Lefebvre et al., "Retinoic Acid Stimulates Regeneration of Mammalian Auditory Hair Cells," *Science*, 260:692–695 (Apr. 30, 1993).

Lefebvre et al., "Temporal Pattern of Nerve Growth Factor (NGF) Binding in vivo and the in vitro Effects of NGF on Cultures of Developing Autitory and Vestibular Neurons," *Acta Otolaryngol.*, 111:304–311 (1991).

Leibrock et al., "Molecular Cloning and Expression of Brain–derived Neurotrophic Factor," *Nature*, 341:149–152 (Sep. 14, 1989).

Levi–Montalcini, R., "The Nerve Growth Factor: Thirty–five Years Later," *The EMBO Journal*, 6(5):1145–1154 (1987).

Lim, "Effects of Noise and Ototoxic Drugs at the Cellular Level in the Cochlea: A Review," *Am. J. Otolaryngol.*, 7(2):73–99 (Mar. 1986).

Lippe et al., "Loss of Avian Spiral Ganglion Neurons Following Aminoglycoside–induced Hair Cell Loss and Regeneration," *Assoc. Res. Otolaryngol. Abstracts*, (Abstract 336) p. 84 (1995).

Maisonpierre et al., "Neurotrophin–3: A Neurotrophic Factor Related to NGF and BDNF," *Science*, 247:1446–1451 (Mar. 23, 1990).

Martin–Zanca et al., "Molecular and Biochemical Characterization of the Human trk Proto–Oncogene," *Molecular & Cellular Biology*, 9(1):24–33 (Jan. 1989).

McAlpine et al., "The Ototoxic Mechanism of Cisplatin," *Hearing Research*, 47:191–204 (1990).

McCabe et al., "The Effect of Aspirin Upon Auditory Sensitivity," *The Annals of Otology Rhinology & Laryngology*, LXXIV (2):312–325 (1965).

Mollman, "Cisplatin Neurotoxicity," *New England J. of Medicine*, 322(2):126–127 (Jan. 11 1990).

Myers et al., "Salicylate Ototoxicity," *Arch. Otolaryng.*, 82:483–493 (Nov. 1965).

Nakai et al., "Ototoxicity of the Anticancer Drug Cisplatin," *Acta Otolaryngol.*, 93:227–232 (1982).

Park, David S. et al., "Multiple Pathways of Neuronal Death Induced by DNA–Damaging Agents, NGF Deprivation, and Oxidative Stress," *The Journal of Nuroscience*, vol. 18, No. 3, pp. 830–840 (Feb. 1, 1998).

Pirvola et al., "Brain–derived Neurotrophic Factor and Neurotrophin 3 mRNAs in the Peripheral Target Fields of Developing Inner Ear Ganglia," *Proc. Natl. Acad. Sci. USA*, 89:9915–9919 (1992).

Pryor, "Assessment of Auditory Dysfunction," *Principles of Neurotoxicology*, Loius W. Chang, New York: Marcel Dekker, Inc., pp. 345–371 (1994).

Rastel et al., "An Original Organotypic Culture Method to Study the Organ of Corti of the Newborn Rat in vitro," *Journal of Neuroscience Methods*, 47:123–131 (1993).

Richardson et al., "Cochlear Cultures as a Model System for Studying Aminoglycoside Induced Ototoxicity," *Hearing Research*, 53:293–311 (1991).

Roelofs et al., Peripheral Sensory Neuropathy and Cisplatin Chemotherapy, *Neurology*, 34:934–938 (Jul. 1984).

Rosenthal et al., "Primary Structure and Biological Activity of a Novel Human Neurotrophic Factor," *Neuron*, 4:767–773 (May 1990).

Rybak, L., "Ototoxic Mechanisms," *Neurobiology of Hearing: The Cochlea*, R.A. Altschuler, New York:Raven Press pp. 441–454 (1986).

Schacht, "Molecular Mechanisms of Drug–induced Hearing Loss," *Hearing Reserach*, 22:297–304 (1986).

Scheoterson et al., "Neurotrophin and Neurotrophin Receptor mRNA Expression in Developing Inner Ear," *Hearing Research*, 73:92–100 (1994).

Scopes,"Protein Purification: Principles and Practice," *Springer Advanced Texts in Chemistry*, pp. 176–181 (1987).

Sera et al., "Morphological Changes in the Vestibular Epithelia and Ganglion Induced by Ototoxic Drug," *Scanning Microscopy*, 1(3):1191–1197 (1987).

Shelton et al., "Human trks: Molecular Cloning, Tissue Distribution, and Expression of Extracellular Domain Immunoadhesins," *The Journal of Neuroscience*, 15(1):477–491 (1995).

Siegal et al., "Cisplatin–induced Peripheral Neuropathy," *Cancer*, 66:1117–1123 (Sep. 15, 1990).

Snider, W., "Functions of the Neurotrophins During Nervous System Development: What the Knockouts Are Teaching Us," *Cell* 77:627–638 (Jun. 3, 1994).

Sobkowicz et al., "Organotypic Development of the Organ of Corti in Culture," *Journal of Neurocytology*, 4:543–572 (1975).

Soppet et al., "The Neurotrophic Factors Brain–Derived Neurotrophic Factor and Neurotrophin–3 are Ligands for the trkB Tyrosine Kinase Receptor," *Cell* 65:895–903 (May 31, 1991).

Squinto et al., "trkB Encodes a Functional Receptor for Brain–Derived Neurotrophic Factor and Neurotrophin–3 but Not Nerve Growth Factor," *Cell* 65:885–893 (May 31, 1991).

Stadnicki et al., "Cis–dichlorodiammineplatinum (II) (NSC–119875): Hearing Loss and Other Toxic Effects in Rhesus Monkeys," *Cancer Chemotherapy Reports* 59(3):467–480 (May/Jun. 1975).

Thompson et al., "Cisplatin Neuropathy: Clinical, Electrophysiological, Morphologic, and Toxicologic Studies," *Cancer* 54:1269–1275 (1984).

Tsoulfas et al., "The Rat trkC Locus Encodes Multiple Neurogenic Receptors that Exhibit Differential Response to Neurotrophin–3 in PC12 Cells," *Neuron* 10:975–990 (May 1993).

Tsue et al., "Diffusible Factors Regulate Hair Cell Regeneration in the Avian Inner Ear," *Proc. Natl. Acad. Sci. USA* 91:1584–1588 (Feb. 1994).

Tsue et al., "Hair Cell Regeneration in the Inner Ear," *Otolaryngol Head Neck Surg.*, 111:281–301 (1994).

Valenzuela et al., "Alternative Forms of Rat TrkC with Different Functional Capabilities," *Neuron* 10:963–974 (May 1993).

Vazquez et al., "Pattern of trkB Protein–like Immunoreactivity in vivo and in vitro Effects of Brain–derived Neurotrophic Factor (BDNF) on Developing Cochlear and Vestibular Neurons," *Anat. Embryol.*, 189:157–167 (1994).

Verdi et al., "p75$^{LNGFR}$ Regulates Trk Signal Transduction and NGF induced Neuronal Differentiation in MAH Cells," *Neuron* 12:733–745 (Apr. 1994).

Von Bartheld et al., "Expression of Nerve Growth Factor (NGF) Receptors in the Developing Inner Ear of Chick and Rat," *Development* 113:455–470 (1991).

Wang, Jian et al., "Leupeptin protects sensory hair cells from acoustic trauma," *NeuroReport*, vol. 10, pp. 811–816 (1999).

Warchol et al., "Regenerative Proliferation in Inner Ear Sensory Epithelia from Adult Guinea Pigs and Humans," *Science* 259:1619–1622 (Mar. 12, 1993).

Weskamp et al., "Evidence that Biological Activity of NGF is Mediated Through a Novel Subclass of High Affinity Receptors," *Neuron* 6:649–663 (Apr. 1991).

Wheeler et al., "Expression of BDNF and NT–3 mRNA in Hair Cells of the Organ of Corti: Quantitative Analysis in Developing Rats," *Hearing Research*, 73:46–56 (1994).

Windebank et al., "The Effect of Nerve Growth Factor, Ciliary Neurotrophic Factor, and ACTH Analogs on Cisplatin Neurotoxicity in vitro," *Neurology* 44:488–494 (Mar. 1994).

Wittmaack, "Beitrage zur Kenntnis der Wirkung des Chinins auf das Gehorargan," *Physiologie*, Pfluger, Funfundneunzigster Band pp. 237–263 (1903).

Woodford et al., "Effects of Combinations of Sodium Salicylate and Noise on the Auditory Threshold," *Ann. Otol.*, 87:117–127 (1978).

Yamashita et al., "Induction of Cell Proliferation in Mammalian Inner–ear Sensory Epithelia by Transforming Growth Factor α and Epidermal Growth Factor," *Proc. Natl. Acad. Sci. USA* 92:3152–3155 (1995).

Yan et al., "Brain–derived Neurotrophic Factor Rescues Spinal Motor Neurons from Axotomy–induced Cell Death," *Nature* 360–753–755 (1992).

Yan et al., "Distribution of Intracerebral Ventricularly Administered Neurotrophins in Rat Brain and its Correlation with Trk Receptor Expression," *Experimental Neurology* 127:23–36 (1994).

Ylikoski et al., "Expression Patterns of Neurotrophin and Their Receptor mRNA in the Rat Inner Ear," *Hearing Research* 65:69–78 (1993).

Zheng et al., "Neurotrophin–4/5 Enhances Survival of Cultured Spiral Ganglion Neurons and Protects Them From Cisplatin Neurotoxicity," *The Journal of Neuroscience*, 15(7):5079–5087 (Jul. 1995).

Zheng et al., "Neurotrophin–4/5, Brain–Derived Neurotrophic Factor, and Neurotrophin–3 Promote Survival of Cultured Vestibular Ganglion Neurons and Protect Them Against Neurotoxicity of Ototoxins," *Journal of Neurobiology*, 28(3):330–340 (1995).

Zheng et al., Chemical Abstract 124:1380 (1995).

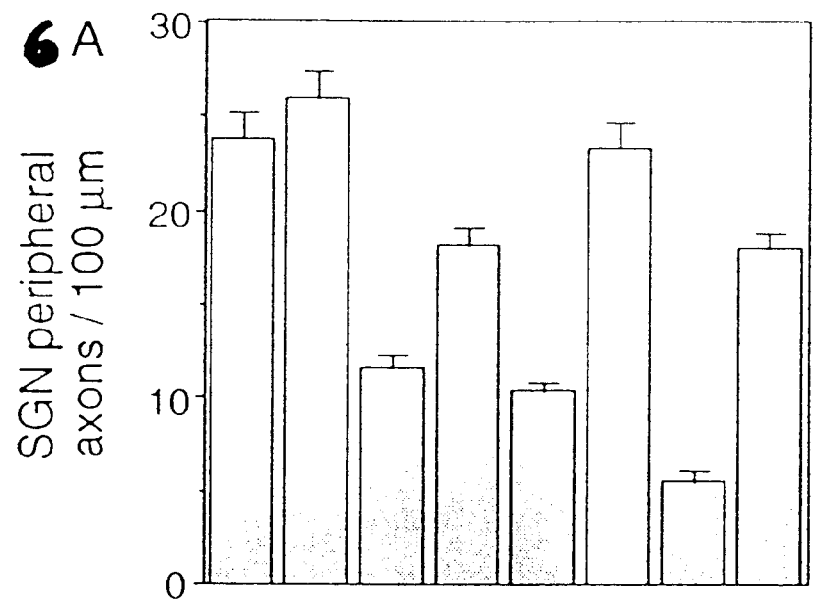
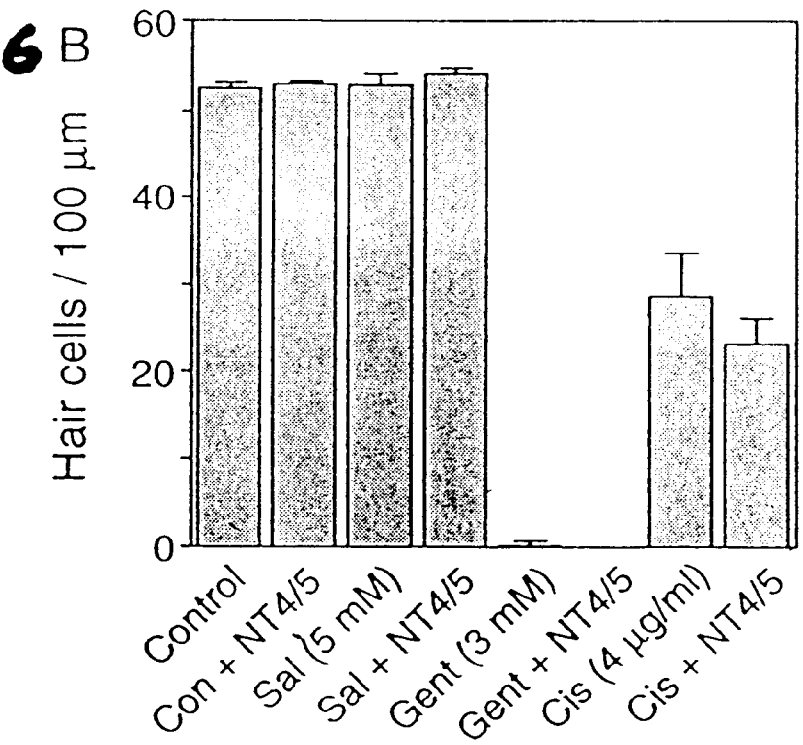

TREATMENT OF HEARING IMPAIRMENTS

This application claims the benefit under 35 U.S.C. §120 as a continuation of U.S. application Ser. No. 08/778,357 filed Jan. 2, 1997, now U.S. Pat. No. 6,225,282, and under 35 U.S.C. §119(e) of U.S. Provisional Application No. 60/044,407 filed Jan. 5, 1996, the contents of which are incorporated herein by reference.

BACKGROUND

1. Technical Field

This application relates to methods for prophylactic and therapeutic treatment of hearing impairments. More particularly, the application relates to prevention or therapy of ototoxin-induced hearing impairments by administration of neurotrophins.

2. Introduction

Hearing impairments are serious handicaps which affect millions of people. Hearing impairments can be attributed to a wide variety of causes, including infections, mechanical injury, loud sounds, aging, and chemical-induced ototoxicity that damages neurons and/or hair cells of the peripheral auditory system. The peripheral auditory system consists of auditory receptors, hair cells in the organ of Corti, and primary auditory neurons, the spiral ganglion neurons in the cochlea. Spiral ganglion neurons ("SGN") are primary afferent auditory neurons that deliver signals from the peripheral auditory receptors, the hair cells in the organ of Corti, to the brain through the cochlear nerve. The eighth nerve connects the primary auditory neurons in the spiral ganglia to the brain stem. The eight nerve also connects vestibular ganglion neurons ("VGN"), which are primary afferent sensory neurons responsible for balance and which deliver signals from the utricle, saccule and ampullae of the inner ear to the brain, to the brainstem. Destruction of primary afferent neurons in the spiral ganglia has been attributed as a major cause of hearing impairments. Damage to the peripheral auditory system is responsible for a majority of hearing deficits (Dublin, 1976; Rybak, 1986; Lim, 1986; Pryor, 1994).

During embryogenesis, the vestibular ganglion, spiral ganglion, and the otic vesicle are derived from the same neurogenic ectoderm, the otic placode. The vestibular and auditory systems thus share many characteristics including peripheral neuronal innervations of hair cells and central projections to the brainstem nuclei. Both of these systems are sensitive to ototoxins that include therapeutic drugs, antineoplastic agents, contaminants in foods or medicines, and environmental and industrial pollutants. Ototoxic drugs include the widely used chemotherapeutic agent cisplatin and its analogs (Fleischman et al., 1975; Stadnicki et al., 1975; Nakai et al., 1982; Berggren et al., 1990; Dublin, 1976; Hood and Berlin, 1986), commonly used aminoglycoside antibiotics, e.g. gentamicin, for the treatment of infections caused by Gram-negative bacteria, (Sera et al., 1987; Hinojosa and Lerner, 1987; Bareggi et al., 1990), quinine and its analogs, salicylate and its analogs, and loop-diuretics.

The toxic effects of these drugs on auditory cells and spiral ganglion neurons are often the limiting factor for their therapeutic usefulness. For example, antibacterial aminoglycosides such as gentamicins, streptomycins, kanamycins, tobramycins, and the like are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169–71 (1980) or most recent edition). Aminoglycoside antibiotics are generally utilized as broad spectrum antimicrobials effective against, for example, gram-positive, gram-negative and acid-fast bacteria. Susceptible microorganisms include Escherichia spp., Hemophilus spp., Listeria spp., Pseudomonas spp., Nocardia spp., Yersinia spp., Klebsiella spp., Enterobacter spp., Salmonella spp., Staphylococcus spp., Streptococcus spp., Mycobacteria spp., Shigella spp., and Serratia spp. Nonetheless, the aminoglycosides are used primarily to treat infections caused by gram-negative bacteria and, for instance, in combination with penicillins for the synergistic effects. As implied by the generic name for the family, all the aminoglycoside antibiotics contain aminosugars in glycosidic linkage. Ototoxicity is a dose-limiting side-effect of antibiotic administration. For example, nearly 75% of patients given 2 grams of streptomycin daily for 60 to 120 days displayed some vestibular impairment, whereas at 1 gram per day, the incidence decreased to 25% (U.S. Pat. No. 5,059,591). Auditory impairment was observed: from 4 to 15% of patients receiving 1 gram per day for greater than 1 week develop measurable hearing loss, which slowly becomes worse and can lead to complete permanent deafness if treatment continues. Ototoxicity is also a serious dose-limiting side-effect for cisplatin, a platinum coordination complex, that has proven effective on a variety of human cancers including testicular, ovarian, bladder, and head and neck cancer. Cisplatin damages auditory and vestibular systems (Fleischman et al., 1975; Stadnicki et al., 1975; Nakai et al., 1982; Carenza et al., 1986; Sera et al., 1987; Bareggi et al., 1990). Salicylates, such as aspirin, are the most commonly used therapeutic drugs for their anti-inflammatory, analgesic, anti-pyretic and anti-thrombotic effects. Unfortunately, they have ototoxic side effects. They often lead to tinnitus ("ringing in the ears") and temporary hearing loss (Myers and Bernstein, 1965). However, if the drug is used at high doses for a prolonged time, the hearing impairment can become persistent and irreversible, as reported clinically (Jarvis, 1966).

Accordingly, there exists a need for means to prevent, reduce or treat the incidence and/or severity of hearing impairments involving auditory nerves, particularly that arising as an unwanted side-effect of ototoxic therapeutic drugs including cisplatin and its analogs, aminoglycoside antibiotics, salicylate and its analogs, and loop diuretics. In addition, there exits a need for methods which will allow higher and thus more effective dosing with these ototoxicity-inducing pharmaceutical drugs, while concomitantly preventing or reducing ototoxic effects caused by these drugs. What is needed is a method that provides a safe, effective, and prolonged means for prophylactic or curative treatment of hearing impairments related to nerve damage, loss, or degeneration, particularly ototoxin-induced. In addition there is needed a rapid, reliable, and facile system for testing the effects and mechanisms of ototoxic agents on hearing in animals, including humans, and for testing the efficacy of therapeutics to prevent, reduce or treat these impairments. The present invention provides a method and system to achieve these goals and others as well.

SUMMARY

The present invention is based in part on the discovery disclosed herein that administration of certain neurotrophins can prevent or reduce gentamicin-, cisplatin-, or salicylate-induced cell death of SGNs in dissociated cell culture and in cochlear explant cultures in a dose-dependent manner. When neurotrophins or other growth factors were added together with sodium salicylate, gentamicin or cisplatin to the culture, SGNs were protected by neurotrophin-4/5 (NT-4/5), brain-derived neurotrophic factor (BDNF) and neurotrophin-3 (NT-3), but not by NGF or other growth factors, including epidermal growth factor (EGF), basic fibroblast growth factor (PFGF), FGF-5, FGF-7, insulin-like growth factor-1 (IGF-1), platelet-derived growth factor (PDGF), transforming growth factor-α (TGF-α), TGF-β1, TGF-β2, TGF-β3, TGF-β5 and retinoic acid. Accordingly, it is one object of the invention to provide a method for treating a mammal to prevent, reduce, or treat the incidence of or severity of a neuron-related hearing impairment, particularly an ototoxin-induced or -inducible hearing impairment, by administering to a mammal in need of such treatment a prophylactically or therapeutically effective amount of a trkB or trkC agonist. The trkB or trkC agonist is preferably a neurotrophin, more preferably NT-4/5, NT-3, or BDNF, and most preferably NT-4/5, or a functional fragment or derivative thereof, a chimeric neurotrophin, a pantropic neurotrophin, or a small molecule or antibody agonist thereof.

According to the method of this invention a composition of the invention can be administered at a suitable interval(s) either prior to, subsequent to, or substantially concurrently with the administration of or exposure to hearing-impairment inducing neuronal damage, preferably ototoxin-induced or -inducible hearing impairment. It is another object of the invention to provide a method for treating a mammal to prevent, reduce, or treat neuronal-damage-related hearing impairments, preferably an ototoxin-induced hearing impairment, by administering to a mammal in need of such treatment a composition containing a prophylactically or therapeutically effective amount of the trkB or trkC agonist in combination with a prophylactically or therapeutically effective amount of a second trkB or trkC agonist or an agent that acts synergistically or additively to enhance or complement the prophylactic or therapeutic effect of the first trkB or trkC agonist.

Also provided are improved compositions and methods for treatments requiring administration of a pharmaceutical having an ototoxic, hearing-impairing side-effect, wherein the improvement includes administering (prophylactically or therapeutically) a therapeutically effective amount of a trkB or trkC agonist to treat the ototoxicity induced by the pharmaceutical. Accordingly, it is an object of the invention to provide an improved composition containing a trkB or trkC agonist, preferably a neurotrophin, more preferably NT-4/5, NT-3, or BDNF, and most preferably NT-4/5, or a functional fragment or derivative thereof, a chimeric neurotrophin, a pantropic neurotrophin, or a small molecule or antibody agonist thereof, in combination with an ototoxic, hearing-impairing pharmaceutical drug for administration to a mammal. Such combination compositions can further contain a pharmaceutically acceptable carrier. The pharmaceutical composition will have lower ototoxicity than the ototoxic pharmaceutical alone, and preferably, will have a higher dosage of the ototoxic pharmaceutical than typically used. Examples of such improved compositions include cisplatin or other ototoxic neoplastic agent or an aminoglycoside antibiotic(s) in combination with a trkB or trkC agonist.

Still further, the invention relates to the use in medicine of compositions of the invention in cases of bacterial infection. The present invention provides a solution to the art that has long sought a therapy and a medicament which can treat the ototoxic effects currently associated with certain antibiotics, and particularly with the more popular and commonly used aminoglycoside antibiotics without sacrificing the antimicrobial effectiveness of the aminoglycosides.

Still further, the invention relates to the use in medicine of compositions of the invention in cases of cancer. The present invention provides a solution to the art that has long sought a therapy and a medicament which can treat the ototoxic effects currently associated with certain chemotherapeutics, and particularly with the more popular and commonly used cisplatin chemotherapeutics without sacrificing the antineoplastic effectiveness of cisplatin or its analogs.

Still further, the invention relates to the use in medicine of compositions of the invention in cases where anti-inflammation, analgesic, or cardiovascular effects are desired. The present invention provides a solution to the art that has long sought a therapy and a medicament which can treat the ototoxic effects currently associated with certain salicylate compounds, and particularly with the more popular and commonly used aspirin, without sacrificing the effectiveness of the salicylate compounds.

Still further, the invention relates to the use in medicine of compositions of the invention in cases where diuretics are needed. The present invention provides a solution to the art that has long sought a therapy and a medicament which can treat the ototoxic effects currently associated with certain diuretics, and particular with the more popular and commonly used loop-diuretics, without sacrificing their diuretic effectiveness.

Still further, the invention relates to the use in medicine of compositions of the invention in cases where quinine or quinine-like compounds are needed. The present invention provides a solution to the art that has long sought a therapy and a medicament which can treat the ototoxic effects currently associated with certain quinines without sacrificing their effectiveness.

Finally, it is an object of the invention to provide a organotypic cochlear explant culture system that allows reliable, rapid, and facile determination of the ototoxic effect of compounds and the prophylactic or therapeutic effect of candidate compositions and methods of the invention.

Additional objects and features of the invention will be apparent to those skilled in the art from the following detailed description and appended claims when taken in conjunction with the figures.

Other aspects of the invention will become apparent from the following detailed description and the claims.

BRIEF DESCRIPTION OF THE DRAWINGS

FIGS. 6A and 6B depict quantitation of toxic effects of sodium salicylate on SGNs (FIG. 6A) and hair cells (FIG. 6B). Cochlear explants were prepared from P3 rats, embedded and cultured in 3-D collagen gels. Ototoxins were added at various concentrations to 2-day cultures for 2 more days. After the preparations were processed for double histochemistry with N52 and phalloidin, they were examined under Zeiss Axiophot epifluorescent microscope. For each culture, SGN peripheral axons and hair cells were counted from 3–4 randomly selected fields in the middle turn of each culture. Data were collected from 6 or more cultures for each of the experimental groups. Two-tailed, unpaired t-test was used for statistical analysis. Note that sodium salicylate selectively induced degeneration of SGNs, but not hair cells loss. The error bars are SEM and double asterisks (**) indicate significant differences between experimental and control cultures (p<0.001).

DETAILED DESCRIPTION

Figure 1:
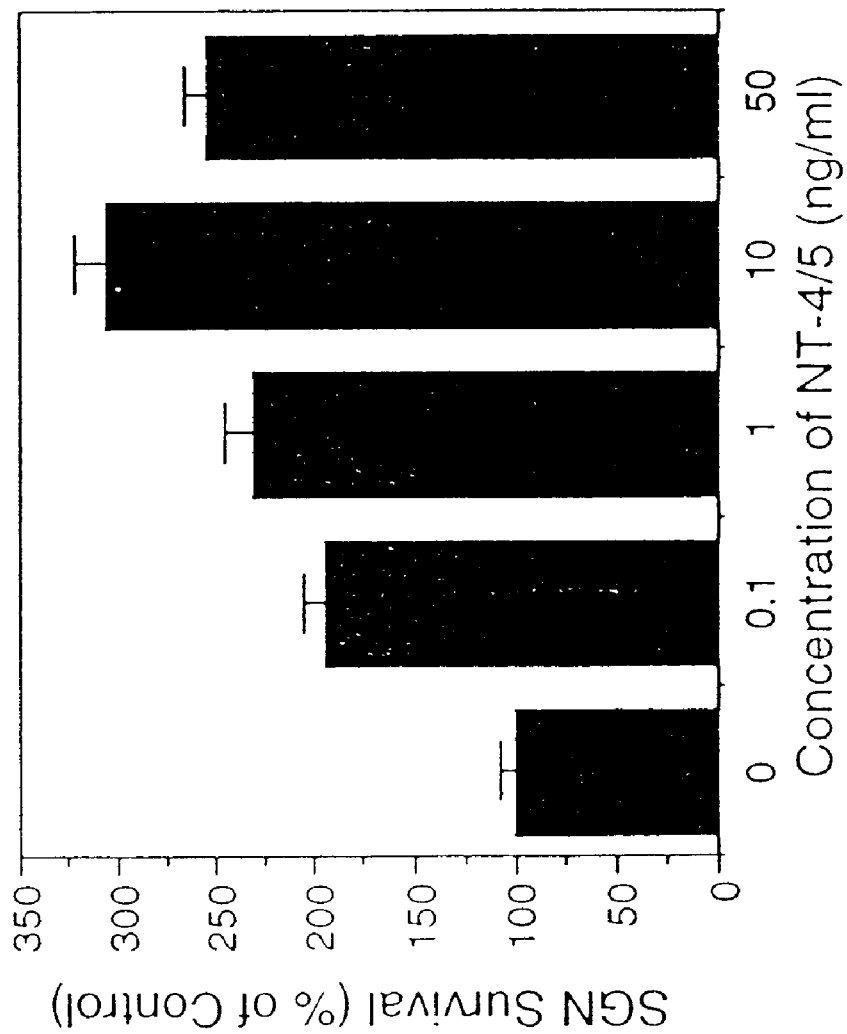
FIG. 1 is a histogram depicting the effects of NT-4/5 on SGN survival. SGNs were prepared from P5 rats, plated and kept for 2 days in serum-free medium in the absence or presence of NT-4/5 at different concentrations. Viable SGNs were identified by labeling with a neurofilament monoclonal antibody (N52), viewed under a Zeiss Axiophot microscope, and counted using a grid ocular reticule covering an area of 1 $m^1m$. For each culture, about 10 randomly selected fields were counted. Data were collected from 3 to 5 cultures and normalized as a percentage of the number of viable neurons in the control cultures in each of the experiments. The error bars represent SEM. As compared to control cultures, NT-4/5 showed very significant survival-promoting effects on SGNs at all doses ($P<0.001$, 2-tailed, unpaired t-test).

In general, the following words or phrases have the indicated definition when used in the description, examples, and claims:

"Treatment" refers to both therapeutic treatment and prophylactic or preventative measures, wherein the object is to prevent or slow down (lessen) neuron-damage-related hearing impairment, preferably ototoxin-induced or inducible. Those in need of treatment include those already experiencing a hearing impairment, those prone to having the impairment, and those in which the impairments are to be prevented. The hearing impairments are due to neuronal damage, wherein the damage is caused by infections, mechanical injury, loud sounds, aging, or, preferably, chemical-induced ototoxicity, wherein ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

By "ototoxic agent" in the context of the present invention is meant a substance that through its chemical action injures, impairs, or inhibits the activity of a component of the nervous system related to hearing to in turn impair hearing. The list of ototoxic agents that cause hearing impairments includes, but is not limited to, neoplastic agents such as vincristine, vinblastine, cisplatin, taxol, or dideoxy-compounds, e.g., dideoxyinosine; alcohol; metals; industrial toxins involved in occupational or environmental exposure; contaminants of food or medicinals; or over-doses of vitamins or therapeutic drugs, e.g., antibiotics such as penicillin or chloramphenicol, or megadoses of vitamins A, D, or B6, salicylates, quinines and loop diuretics. Other toxic agents that can cause ototoxicity-inducing hearing impairment can be identified and characterized by methods as taught herein. By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

"Chronic" administration refers to administration of the agent(s) in a continuous mode as opposed to an acute mode, so as to maintain the initial anti-ototoxic effect for an extended period of time.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

A "patient" for the purposes of the present invention includes both humans and other mammals. Thus the methods are applicable to both human therapy and veterinary applications.

"Non-immunogenic in a human" means that upon contacting the polypeptide in a pharmaceutically acceptable carrier and in a therapeutically effective amount with the appropriate tissue of a human, no state of sensitivity or resistance to the polypeptide is demonstrable upon the second administration of the polypeptide after an appropriate latent period (e.g., 8 to 14 days).

By "hearing impairment" is meant a neurologic disorder, oto-neurological in nature, typically sensorineural, but including composite loss (both sensorineural and conductive loss), preferably either a sensory or a neural (8th nerve related) hearing loss, and most preferably a sensory loss (cochlear related), in which the patient will display, complain of, or is diagnosed to have a hearing loss. Conductive hearing loss is typically related to the external or middle ear. These impairments of interest to the present invention are those associated with damage, loss, or degeneration of a neuron of the auditory system. Less preferably such impairments can occur along with hair cell damage or conductive hearing loss damage. Preferably affected are neurons of the 8th nerve, cochlea and connecting neurons of the brainstem and their temporal lobe connections. The loss can be unilateral. Hair cells are epithelial cells possessing fine projections and located in the maculae and the organ of Corti.

Hearing impairments relevant to the invention are preferably sensory hearing loss due to end-organ lesions, e.g., acoustic trauma, viral endolymphatic labyrinthitis, Meniere's disease. The impairment can also be neural hearing loss due to events including cerebellopontine angle tumors of the 8th nerve. Hearing impairments include tinnitus, which is a perception of sound in the absence of an acoustic stimulus, and may be intermittent or continuous, wherein there is diagnosed a sensorineural loss. Hearing loss may be due to bacterial or viral infection of the 8th nerve ganglia, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chickenpox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than 85 decibels (db) that damages the inner ear. Hearing loss includes presbycusis, which is a sensorineural hearing loss occurring as a normal part of aging, fractures of the temporal bone extending into the middle ear and rupturing the tympanic membrane and possibly the ossicular chain, fractures affecting the cochlea, and acoustic neurinoma, which are tumors generally of Schwann cell origin that arise from either the auditory or vestibular divisions of the 8th nerve. Preferably, the hearing loss is caused by an ototoxic drug that effects the auditory portion of the inner ear, particularly the organ of Corti. Incorporated herein by reference are Chapters 196, 197, 198 and 199 of The Merck Index, 14th Edition, (1982), Merck Sharp & Dome Research Laboratories, N.J. and related chapters in the most recent edition) relating to description and diagnosis of hearing impairments.

Tests are known and available for diagnosing hearing impairments. Neuro-otological, neuro-ophthalmological, neurological examinations, and electro-oculography can be used. (Wennmo et al. *Acta Otolaryngol* (1982) 94:507–15). Sensitive and specific measures are available to identify patients with auditory impairments. For example, tuning fork tests can be used to differentiate a conductive from a sensorineural hearing loss and determine whether the loss is unilateral. An audiometer is used to quantitate hearing loss, measured in decibels. With this device the hearing for each ear is measured, typically from 125 to 8000 Hz, and plotted as an audiogram. Speech audiometry can also be performed. The speech recognition threshold, the intensity at which speech is recognized as a meaningful symbol, can be determined at various speech frequencies. Speech or phoneme discrimination can also be determined and used an indicator of sensorineural hearing loss since analysis of speech sounds relies upon the inner ear and 8th nerve. Tympanometry can be used to diagnose conductive hearing loss and aid in the diagnosis of those patients with sensorineural hearing loss. Electrocochleography, measuring the cochlear microphonic response and action potential of the 8th nerve, and evoked response audiometry, measuring evoked response from the brainstem and auditory cortex, to acoustic stimuli can be used in patients, particularly infants and children or patients with sensorineural hearing loss of obscure etiology. These tests serve a diagnostic function as well as a clinical function in assessing response to therapy.

Sensory and neural hearing losses can be distinguished based on tests for recruitment (an abnormal increase in the perception of loudness or the ability to hear loud sounds normally despite a hearing loss ), sensitivity to small increments in intensity, and pathologic adaptation, including stapedial reflex decay. Recruitment is generally absent in neural hearing loss. In sensory hearing loss the sensation of loudness in the affected ear increases more with each increment in intensity than it does in the normal ear. Sensitivity to small increments in intensity can be demonstrated by presenting a continuous tone of 20 db above the hearing threshold and increasing the intensity by 1 db briefly and intermittently. The percentage of small increments detected yields the "short increment sensitivity index" value. High values, 80 to 100%, is characteristic of sensory hearing loss, whereas a neural lesion patient and those with normal hearing cannot detect such small changes in intensity. Pathologic adaptation is demonstrated when a patient cannot continue to perceive a constant tone above the threshold of hearing; also known as tone decay. A Bekesy automatic audiometer or equivalent can be used to determine these clinical and diagnostic signs; audiogram patterns of the Type II pattern, Type III pattern and Type IV pattern are indicative of preferred hearing losses suitable for the treatment methods of the invention. As hearing loss can often be accompanied by vestibular impairment, vestibular function can be tested, particular when presented with a sensorineural hearing loss of unknown etiology. When possible diagnostics for hearing loss, such as audiometric tests, should be performed prior to exposure in order to obtain a patient normal hearing baseline. Upon exposure, particularly to an ototoxic drug, audiometric tests should be performed twice a week and continued testing should be done even after cessation of the drug treatment since hearing loss may not occur until several days after cessation.

In one embodiment the invention constitutes a method for treating a mammal having or prone to a hearing impairment or treating a mammal prophylactically to prevent or reduce the occurrence or severity of a hearing impairment that would result from exposure to a neuronal injury, loss, or degeneration, preferably caused by an ototoxic agent, wherein a therapeutically effective amount of a trkB or trkC agonist is administered to the mammal. Preferably the agonist is a neurotrophin, more preferably neurotrophin NT-4/5, NT-3, or BDNF, a functional fragment, fusion or derivative thereof, such as a chimeric neurotrophin (having both trkB and trkC agonism), a pantropic neurotrophin, or a small molecule or antibody agonist thereof, as discussed in detail herein. Most preferably the agonist is NT-4/5 or a chimeric or pantropic variant thereof having at least both trkB and trkC agonist activity. A preferred chimeric or pantropic neurotrophin has a region conferring NT-3-receptor binding specificity and a region conferring NT-4/5-receptor binding specificity. A preferred pantropic neurotrophin is MNTS-1. In a preferred embodiment the binding of a chimeric or pantropic neurotrophin to a neurotrophic receptor is at least 80% of the binding of the natural neurotrophin ligand to the receptor. When the patient is human, the neurotrophins are preferably human neurotrophins or derived from human neurotrophin sequences, in part to avoid or minimize recognition of the agonist as foreign. Optionally, the trkB or trkC agonist is administered alone or in combination. Additional optional components include a hair cell growth factor or agonist, which are compounds known to promote hair cell survival, regeneration, growth, proliferation, or prevent or reduce cytotoxicity of hair cells. The methods of the invention are particularly effective when the hearing impairment is ototoxin induced or inducible.

It is another object of the invention to provide a method for treating a mammal to prevent, reduce, or treat a hearing impairment, preferably an ototoxin-induced hearing impairment, by administering to a mammal in need of such treatment a composition containing a prophylactically or therapeutically effective amount of the trkB or trkC agonist in combination with a prophylactically or therapeutically effective amount of a second trkB or trkC agonist or an agent that acts synergistically or additively to enhance or complement the prophylactic or therapeutic effect of the first trkB or trkC agonist. By "complement" is meant that the second agonist agonizes the trk not recognized by the first agonist such that the combination of first and second agonists achieves agonism of both trkB and trkC. An example of one such embodiment of this type is the use of both NT-4/5 and NT-3, which can be administered as a single formulation or as separate formulations.

In one embodiment is a method for treating a hearing impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

The methods of the invention are particularly effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2.

Hearing impairments induced by aminoglycosides can be prevented or reduced by the methods of the invention. Although the aminoglycosides are particularly useful due to their rapid bactericidal action in infections by susceptible organisms, their use is limited to more severe, complicated infections because of ototoxic and nephrotoxic side-effects. For this reason the aminoglycosides are considered to have a low therapeutic/risk ratio compared to other antibiotics used systemically. Damage to ganglion neurons has been noted at high doses of aminoglycosides (Sera et al., 1987) or after a delayed time (Lippe et al., 1995). Aminoglycoside antibiotics were reported to cause direct neuronal loss in the spiral ganglion in two young patients (Hinojosa and Lerner, 1987).

Aminoglycosides are a class of compounds characterized by the ability to interfere with protein synthesis in microorganisms. Aminoglycosides consist of two or more amino sugars joined in a glycoside linkage to a hexose (or aminocyclitol) nucleus. The hexose nuclei thus far known are either streptidine or 2-deoxystreptamine, though others may be anticipated. Aminoglycoside families are distinguished by the amino sugar attached to the aminocyclitol. For example, the neomycin family comprises three amino sugars attached to the central 2-deoxystreptamine. The kanamycin and glutamicin families have only two amino sugars attached to the aminocyclitol. Aminoglycosides include: neomycins (e.g. neomycin B and analogs and derivatives thereof), paromomycin, ribostamycin, lividomycin, kanamycins (e.g. kanamycin A, kanamycin B, and analogs and derivatives thereof), amikacin, tobramycin, viomycin, gentamicin (e.g., gentamicin C1, gentamicin C 1a, gentamicin C2, and analogs and derivatives thereof), sisomicin, netilmicin, streptomycin, dibekacin, fortimicin, and dihydrostreptomycin.

The aminoglycoside antibiotic which can be employed in conjunction with the ototoxicity inhibiting compositions of the invention is any aminoglycoside antibiotic. Examples of such aminoglycoside antibiotics include kanamycin (Merck Index 9th ed. #5132), gentamicin (Merck Index 9th ed. #4224), amikacin (Merck Index 9th ed. #A1), dibekacin (Merck Index 9th ed. #2969), tobramycin (Merck Index 9th ed. #9193), streptomycin (Merck Index 9th ed. #8611/8612), paromomycin (Merck Index 9th ed. #6844), sisomicin (Merck Index 9th ed. #8292), isepamicin and netilmicin, all known in the art. The useful antibiotics include the several structural variants of the above compounds (e.g. kanamycin A, B and C; gentamicin A, C1, C 1a, C2 and D; neomycin B and C and the like). The free bases, as well as pharmaceutically acceptable acid addition salts of these aminoglycoside antibiotics, can be employed.

For the purpose of this disclosure, the terms "pharmaceutically acceptable acid addition salt" shall mean a mono or poly salt formed by the interaction of one molecule of the aminoglycoside antibiotic with one or more moles of a pharmaceutically acceptable acid. Included among those acids are acetic, hydrochloric, sulfuric, maleic, phosphoric, nitric, hydrobromic, ascorbic, malic and citric acid, and those other acids commonly used to make salts of amine-containing pharmaceuticals.

Accordingly, the methods and compositions of the invention find use for the prevention and treatment of opportunistic infections in animals and man which are immunosuppressed as a result of either congenital or acquired immunodeficiency or as a side-effect of chemotherapeutic treatment. According to an alternate embodiment of the present invention, a trkB or trkC agonists is used advantageously in combination with a known antimicrobial agent to provide improved methods and compositions to prevent and/or treat diseases induced by gram positive bacteria including, but not limited to: *Staphylococcus aureus, Streptococcus pneumonia, Hemophilus influenza;* gram negative bacteria including, but not limited to: *Escherichia coli; Bacterium enteritis, Francisella tularensis;* acid-fast bacteria including, but not limited to *Mycobacterium tuberculosis,* and *Mycobacterium leprae.* Use of a combination of an antimicrobial agent together with a trkB or trkC agonist is advantageous with antibacterial aminoglycosides such as gentamicin, streptomycin, and the like which are known to have serious ototoxicity, which reduce the usefulness of such antimicrobial agents. Use of trkB or trkC agonist in combination with such agents permits a lower dosage of the toxic antimicrobial agents while still achieving therapeutic (antibacterial) effectiveness.

In some embodiments the trkB or trkC agonist is co-administered with an ototoxin. For example, an improved method is provided for treatment of infection of a mammal by administration of an aminoglycoside antibiotic, the improvement comprising administering a therapeutically effective amount of a trkB or trkC agonist to the patient in need of such treatment to reduce or prevent ototoxin-induced hearing impairment associated with the antibiotic. In yet another embodiment is provided an improved method for treatment of cancer in a mammal by administration of a chemotherapeutic compound, the improvement comprises administering a therapeutically effective amount of a trkB or trkC agonist to the patient in need of such treatment to reduce or prevent ototoxin-induced hearing impairment associated with the chemotherapeutic drug.

Also provided herein are methods for promoting spiral ganglion neuron survival upon, prior to, or after exposure to an agent or effect that is capable of inducing a sensorineural hearing impairment. Such agents and effects are those described herein. The method includes the step of administering to the neuron an effective amount of trkB or trkC agonist or other compositions containing same as discussed herein. Preferably, the method is used upon, prior to, or after exposure to a hearing-impairing ototoxin.

In one embodiment the methods of treatment are applied to hearing impairments resulting from the administration of a chemotherapeutic agent to treat its ototoxic side-effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas.

In one embodiment the methods of the invention are applied to hearing impairments resulting from the administration of salicylate, e.g., aspirin, or a salicylate-like compound, to treat its ototoxic side-effect. Salicylates, such as aspirin, are the most commonly used therapeutic drugs for their anti-inflammatory, analgesic, anti-pyretic and anti-thrombotic effects. Unfortunately, they have ototoxic side effects. They often lead to tinnitus ("ringing in the ears") and temporary hearing loss (Myers and Bernstein, 1965). Clinical and animal studies have suggested that the site of action of this drug is in the cochlea (Myers and Bernstein, 1965; McCabe and Dey, 1965). Electrophysiological recordings in animals indicate salicylates result in an increase in hearing suprathreshold, which suggests damage to hair cells (Boettcher et al., 1989; Boettcher and Salvi, 1991). However, postmortem examination of a patient who received large doses of aspirin showed normal hair cell numbers, but a significant loss of SGNs (De Moura and Hayden, 1968). The present experiments clearly demonstrate for the first time, see Examples below, the selective toxic effects of salicylates on auditory neurons, but not on hair cells. Interestingly, the dosage (3 mM) of salicylate which starts to induce significant damage to SGNs in the present study is comparable to the peak serum and perilymph levels that result in hearing losses (Myers and Bernstein, 1965; Woodford et al., 1978; Boettcher et al., 1990). The finding that sodium salicylate at both low and high concentrations exclusively induces degeneration of SGNs and their axons, but not hair cells suggests a possibility that the initial hearing disorder caused by salicylates may result from neuronal dysfunction, perhaps axonal degeneration in the eighth nerve or abnormality in SGNs (Wittmaack, 1903). Once the drug is stopped, the damaged axons may regenerate successfully and restore the normal auditory function. Such initial axonal degeneration is therefore reversible. However, if the drug is used at high doses for a prolonged time, the neuronal impairment will become more severe and SGN death occurs. As a consequence, the hearing impairment may become persistent and irreversible, as reported clinically (Jarvis, 1966).

In one embodiment the methods of the invention are applied to hearing impairments resulting from the administration of quinine and its synthetic substitutes, typically used in the treatment of malaria, to treat its ototoxic side-effect.

In another embodiment the methods of the invention are applied to hearing impairments resulting from administration of a diuretic to treat its ototoxic side-effect. Diuretics, particularly "loop" diuretics, i.e. those that act primarily in the Loop of Henle, are candidate ototoxins. Illustrative examples, not limiting to the invention method, include furosemide, ethacrynic acid, and mercurials. Diuretics are typically used to prevent or eliminate edema. Diuretics are also used in nonedematous states such as hypertension, hypercalcemia, idiopathic hypercalciuria, and nephrogenic diabetes insipidus.

In one embodiment the trkB or trkC agonist is administered prior to administration or exposure to a hearing-impairing event such as exposure to an ototoxin.

In another embodiment the trkB or trkC agonist is administered with an agent that promotes hair cell growth, proliferation, regeneration, or survival. As shown herein, low concentrations of gentamicin preferentially kills hair cells while the damage to the ganglion neurons is not significant. High concentrations of gentamicin induces degeneration of ganglion neurons as well as hair cells. Accordingly, this dual toxicity of aminoglycosides can be treated by the methods of the invention, preferably with compositions of the invention.

Preparation and Identification of Agonists

Agonists to trkB or trkC can be prepared by using the known family of ligands for trkB or trkC. Survival of developing sensory neurons is dependent upon trophic factors derived from their target tissues (Davies et al., 1986). Generally, a neurotrophin is a protein involved in the development, regulation and maintenance of the nervous system, and in particular of neurons. Currently, there are at least five known important neurotrophic factors: nerve growth factor (NGF), neurotrophin-3 (NT-3), neurotrophin-4 (NT-4/5, also sometimes called neurotrophin-5 (NT-5) or NT-4/5), brain-derived neurotrophic factor (BDNF), and ciliary neurotrophic factor (CNTF). The best characterized mammalian neurotrophic factors are members of the nerve growth factor (NGF) family of proteins, and are called neurotrophins. These include NGF (Levi-Montalcini, 1987), brain-derived neurotrophic factor (BDNF) (Barde et al., 1982; Leibrock et al., Nature (1989) 341:149) neurotrophin-3 (NT-3) (Hohn et al., Nature, 344: 339 (1990); Maisonpierre et al., Science, 247: 1446 (1990); Rosenthal et al., Neuron, 4: 767 (1990); copending U.S. Ser. No. 07/494,024 filed Mar. 15, 1990; U.S. application Ser. No. 07/490,004, filed Mar. 7, 1990; Emfors et al., 1990; Jones and Reichardt, 1990) and neurotrophin-4/5 (NT-4/5) (Berkemeier et al., 1991; Ip et al., 1992) and neurotrophin-6 (NT-6). While NT-6 is newly cloned from Xenopus (Gotz et al., 1994) and is less well understood, it is now well accepted that the other four mammalian neurotrophins exert their biological functions through activation of high-affinity binding receptors, the trks (Barbacid, 1993; Snider, 1994). Each of the neurotrophins binds to specific high-affinity receptors, the trks (Klein et al., 1990; Kaplan et al., 1991; Klein et al., 1991a; Klein et al., 1991b; Soppet et al., 1991; Squinto et al., 1991; Lamballe et al., 1991; Tsoulfas et al., 1993; Ip et al., 1993). For example, NGF selectively binds to trkA, BDNF and NT-4/5 to trkB, and NT-3 to trkC. Although neurotrophins exert their main effects through binding to the trks, they also bind to the NGF low affinity receptor, P75. Recent studies indicate that the binding of NGF to P75 may enhance the trkA-mediated signal transduction pathway (Davies et al., 1993a; Verdi et al., 1994; Barker and Shooter, 1994; Clary and Reichardt, 1994).

Neurotrophins transduce intracellular signalling at least in part through the ligand-dependent activation of a class of tyrosine kinase-containing receptors of $M_r$=140–145,000 known as the trks (Martin-Zanca, et al. (1989); Kaplan, et al. (1991) Nature; Klein, et al. (1991a); Kaplan, et al. (1991) Science); Klein, et al. (1991b) Cell; Soppet, et al. (1991); Squinto, et al. (1991); Lamballe, et al. (1991); Tsoulfas, et al. (1993)). Thus, the signal transduction pathway of neurotrophins is initiated by this high-affinity binding to and activation of specific tyrosine kinase receptors and subsequent receptor autophosphorylation (Cordon-Cardo, et al. (1991)). Although there is some degree of cross-receptor interaction between the neurotrophins and the different trks, the predominant specificity appears to be NGF/trkA, BDNF/trkB, and NT-3/trkC while NT-4/5 appears to interact primarily with trkB as efficiently as BDNF (see above and Klein, et al. (1992); Klein, et al. (1989)).

Expression of trkB, trkC and p75 mRNAs in embryonic cochleovestibular ganglia (Ylikoski et al., 1993; Schecterson and Bothwell, 1994) and BDNF and NT-3 mRNAs in the inner ear structures (Pirvola et al., 1992; Wheeler et al., 1994; Schecterson and Bothwell, 1994) has been reported. However, the expression of neurotrophin receptors at the protein level has not been well determined, particularly in postnatal tissue.

DNA sequences encoding NGF, BDNF and NT-3 have all been isolated (Ullrich et al., Nature 303:821–825; Hyman et al., WO 91/03568; Hohn et al., WO 91/03569; and Kaisho et al., FEBS Letters 266:187–191). Researchers have transformed animal and non-animal hosts with these sequences in order to express the neurotrophins.

Researchers have expressed human NGF, BDNF and NT-3 in mammalian expression systems. Bruce and Heinrich (1989, Neurobiology of Aging 10:89–94) expressed a DNA sequence encoding the complete precursor for hNGF in COS cells and detected hNGF dimer in the conditioned medium. However, they could not determine the efficiency at which pre-pro-hNGF was converted to mature hNGF. Kakinuma et al. (EP 0 414 151, 1991) expressed active hNGF in CHO cells. Hyman et al. (WO 91/03568, 1991) expressed hBDNF in CHO cells. Nakahama et al. (EP 0 386 752, 1990) and Hohn et al. (WO 91/03569, 1991) expressed hNT-3 in COS cells.

U.S. Pat. Nos. 5,235,043 and 5,229,500 disclose human BDNF sequence and methods for its production and formulation. Applicant's U.S. patent application Ser. No. 08/581, 662 entitled "Treatment of Balance Impairments" is also incorporated herein by reference.

NT-4/5, and its chimeric or pantropic neurotrophins, are most preferred agonists for use in the methods and compositions of the present invention. Its human gene and amino acid sequence are known (U.S. Pat. No. 5,364,769, which is incorporated herein by reference). NT-4/5 is defined to be a polypeptide encoded by the known mature human NT-4/5 nucleotide sequence set forth in U.S. Pat. No. 5,364,769, fragments thereof having greater than about 5 residues comprising an immune epitope or other biologically active site of NT-4/5, amino acid sequence variants of said sequence, wherein an amino acid residue has been inserted N- or C-terminal to, or within, said sequence or its fragment as defined above, and/or amino acid sequence variants of said sequence or its fragment as defined above wherein an amino acid residue of said sequence or fragment thereof has been substituted by another residue, including other animal species of NT-4/5 such as rat preproNT-4/5, and derivatives of NT-4/5 or its fragments as defined above wherein the NT-4/5 or its fragments have been covalently modified by substitution with a moiety other than a naturally occurring amino acid; provided, however, that such fragment or variant is novel and unobvious over the prior art, and is not NGF, BDNF, or NT-3 of any animal species or any known fragment of such NGF, BDNF, or NT-3. Mature NT-4/5 amino acid sequence variants generally will be about 75% (and usually >85%) homologous on an identical residue basis after aligning (introducing any necessary spaces) to provide maximum homology.

NT-4/5 nucleic acid is defined as RNA or DNA which encodes a NT-4/5 polypeptide or which hybridizes to such DNA and remains stably bound to it under stringent conditions and is greater than about 10 bases in length; provided, however, that such hybridizing nucleic acid is novel and unobvious over any prior art nucleic acid including that which encodes or is complementary to nucleic acid encoding BDNF, NT-3, or NGF. Stringent conditions are those which (1) employ low ionic strength and high temperature for washing, for example, 0.15 M NaCl/0.015 M sodium citrate/ 0.1% NaDodSO$_4$ at 50° C., or (2) use during washing a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

DNA encoding NT-4/5 is obtained from brain tissue cDNA libraries, or genomic DNA, or by in vitro synthesis. Hybridizing nucleic acid generally is obtained by in vitro synthesis. Identification of NT-4/5 DNA most conveniently is accomplished by probing human cDNA or genomic libraries by labeled oligonucleotide sequences selected from the known sequence in accord with known criteria, among which is that the sequence should be of sufficient length and sufficiently unambiguous that false positives are minimized. Typically, a $^{32}$P-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. The nucleic acid may be labeled for diagnostic purposes.

Amino acid sequence variants of NT-4/5 are prepared by introducing appropriate nucleotide changes into the NT-4/5 DNA, or by in vitro synthesis of the desired NT-4/5. Such variants include, for example, deletions from, or insertions or substitutions of, residues within the amino acid sequence for human NT-4/5. Any combination of deletion, insertion, and substitution is made to arrive at the final construct, provided that the final construct possesses the desired characteristics. The amino acid changes also may result in further modifications of NT-4/5 upon expression in recombinant hosts, e.g. introducing or moving sites of glycosylation, or introducing membrane anchor sequences (in accordance with U.S. Ser. No. 07/083,757, filed Aug. 6, 1987, which is equivalent to PCT WO 89/01041 published Feb. 9, 1989).

There are two principal variables in the construction of amino acid sequence variants: the location of the mutation site and the nature of the mutation. These are variants may represent naturally occurring alleles (which will not require manipulation of the NT-4/5 DNA) or predetermined mutant forms which are made by mutating the DNA, either to arrive at an allele or a variant that is not found in nature. In general, the location and nature of the mutation chosen will depend upon the NT-4/5 characteristic to be modified. For example, candidate NT-4/5 antagonists or super agonists will be initially selected by locating sites that are identical or highly conserved among NGF, BDNF, NT-3, and NT-4/5. These sites then will be modified in series, e.g., by (1) substituting first with conservative choices and then with more radical selections depending upon the results achieved, (2) deleting the target residue, or (3) inserting residues of the same or different class adjacent to the located site, or combinations of options 1–3.

One helpful technique is called "ala scanning". Here, a residue or group of target residues are identified and substituted by alanine or polyalanine. Those domains demonstrating functional sensitivity to the alanine substitutions then are refined by introducing further or other variants at or for the sites of alanine substitution. Obviously, such variations which, for example, convert NT-4/5 into NGF, BDNF, or NT-3 are not included within the scope of this invention, nor are any other NT-4/5 variants or polypeptide sequences that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed NT-4/5 variants are screened for the optimal combination of desired activity.

Amino acid sequence deletions generally range from about 1 to 30 residues, more preferably about 1 to 10 residues, and typically are contiguous. Deletions may be introduced into regions of low homology among BDNF, NGF, NT-3, and NT-4/5 to modify the activity of NT-4/5. Deletions from NT-4/5 in areas of substantial homology with BDNF, NT-3, and NGF will be more likely to modify the biological activity of NT-4/5 more significantly. The number of consecutive deletions will be selected so as to preserve the tertiary structure of NT-4/5 in the affected domain, e.g., beta-pleated sheet or alpha helix.

Amino acid sequence insertions include amino- and/or carboxyl-terminal fusions ranging in length from one residue to polypeptides containing a thousand or more residues, as well as intrasequence insertions of single or multiple amino acid residues. Intrasequence insertions (i.e., insertions within the mature NT-4/5 sequence) may range generally from about 1 to 10 residues, more preferably 1 to 5, most preferably 1 to 3. An example of a terminal insertion includes fusion of a heterologous N-terminal signal sequence to the N-terminus of the NT-4/5 molecule to facilitate the secretion of mature NT-4/5 from recombinant hosts. Such signals generally will be homologous to the intended host cell and include STII or lpp for E. coli, alpha factor for yeast, and viral signals such as herpes gD for mammalian cells. Other insertions include the fusion of an immunogenic polypeptide such as a bacterial or yeast protein to the N- or C-termini of NT-4/5.

The third group of variants are those in which at least one amino acid residue in the NT-4/5 molecule, and preferably only one, has been removed and a different residue inserted in its place. In some embodiments substitutions of one to five amino acids are made. In yet another embodiment one to three amino acids are substituted. In some preferred embodiments two amino acid substitutions are made. The substitutions can be chosen from the table herein. An example is the replacement of arginine and lysine by other amino acids to render the NT-4/5 resistant to proteolysis by serine proteases, thereby creating a more stable NT-4/5 analogue. The sites of greatest interest for substitutional mutagenesis include sites where the amino acids found in BDNF, NGF, NT-3, and NT-4/5 are substantially different in terms of side chain bulk, charge or hydrophobicity, but where there also is a high degree of homology at the selected site within various animal analogues of NGF, NT-3, and BDNF (e.g., among all the animal NGFs, all the animal NT-3s, and all the BDNFs). This analysis will highlight residues that may be involved in the differentiation of activity of the trophic factors, and therefore, variants at these sites may affect such activities. Examples of such NT-4/5 sites, numbered from the mature N-terminal end, and exemplary substitutions include NT-4/5 ($G_{78}$→K, H, Q or R) and NT-4/5 ($R_{85}$→E, F, P, Y or W). Other sites of interest are those in which the residues are identical among all animal species' BDNF, NGF, NT-3, and NT-4/5, this degree of conformation suggesting importance in achieving biological activity common to all four factors. These sites, especially those falling within a sequence of at least 3 other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gin; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg; | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Sites particularly suited for conservative substitutions include, numbered from the N-terminus of the mature NT-4/5, R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and T118. Cysteine residues not involved in maintaining the proper conformation of NT-4/5 also may be substituted, generally with serine, in order to improve the oxidative stability of the molecule and prevent aberrant crosslinking. Sites other than those set forth in this paragraph are suitable for deletional or insertional studies generally described above.

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another. Such substituted residues also may be introduced into the conservative substitution sites set forth above or, more preferably, into the remaining (non-conserved) sites.

Examples of NT-4/5 variants include NT-4/5 (65NAE67→NAS or NAT) (this adds an N-linked glycosylation site); NT-4/5(R83-Q94); NT-4/5(G1-C61) (variants so depicted are fragments containing the residues indicated); NT-4/5(G1-C17); NT-4/5(C17-C61); NT-4/5(C17-C78); NT-4/5(C17-C90); NT-4/5(C17-C119); NT-4/5(C17-C121); NT-4/5(R11-R27); NT-4/5(R11-R34); NT-4/5(R34-R53); NT-4/5(C61-C78); NT-4/5(R53-C61); NT-4/5(C61-C119); NT-4/5(C61-C78); NT-4/5(C78-C119); NT-4/5(C61-C90); NT-4/5(R60-C78); NT-4/5(K62-C119); NT-4/5(K62-K91); NT-4/5(R79-R98); NT-4/5(R83-K93); NT-4/5(T101-R111); NT-4/5(G1-C121) V L T V K R V R R; NT-4/5(V40-C121) V L T V K R V R R; NT-4/5(V40-C121) S L T I K R I R A; NT-4/5 (V40-C121) T L S R K A G R R A; D D D S P I A R R G E I S V C D S V S D W V S A P D K D T A V D I K G D D V M V L K K V G I N H S V; NT-4/5(V40-C121); hNGF(S1-V48) NT-4/5(V40-C121) hNGF(V109-A120); BDNF(R7-Q48) NT-4/5(V40-C121) BDNF(V110-R119); NT-4/5(ΔC78); NT-4/5(ΔC61); NT-4/5(ΔQ54-ΔT59) (variants depicted in this fashion comprise deletions of the indicated span of residues, inclusive); NT-4/5(ΔR60-ΔD82); NT-4/5(ΔH85-ΔS88); NT-4/5(ΔW86 -ΔT101); NT-4/5 (R53→H); NT-4/5(K91→H); NT-4/5(V108→F); NT-4/5 (R84→Q, H, N, T, Y or W); and NT-4/5(D116→E, N, Q, Y, S or T).

Also included is NT-4/5 wherein position 70 is substituted with an amino acid residue other than G, E, D or P; position 71 with other than A, P or M; and/or position 83 with other than R, D, S or K; as well as cyclized NT-4/5 fragments, including cyclic polypeptides comprising the sequences IKTG, EIKTG, EIKTGN, SPV, SPVK, HQV, KSS, KSSA, YAEHKS, RYAEHKS, RYAEHKSH, YAEHKSH, ANRTS, NRT, ANRT, NRTS, KEA, KEAR, KEARP, IDDK, SENN, TSENN, TSENNK or KLVG.

Also within the scope hereof are BDNF, NT-3, and NGF amino acid variants having analogous structures to the NT-4/5 variants set forth herein. For example, the analogous positions of NGF, NT-3, and BDNF are substituted with a residue other than D, E, or P, respectively, in analogy to the same mutation at position 70 of NT-4/5.

DNA encoding NT-4/5 variants preferably is prepared by site-specific mutagenesis of DNA that encodes an earlier prepared variant or a nonvariant version of NT-4/5. Site-specific mutagenesis allows the production of NT-4/5 variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., DNA, 2: 183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981), the disclosure of which is incorporated herein by reference. These phage are readily commercially available and their use is generally well known to those skilled in the art. Also, plasmid vectors that contain a single-stranded phage origin of replication (Veira et al., Meth. Enzymol., 153: 3 [1987]) may be employed to obtain single-stranded DNA. Alternatively, nucleotide substitutions are introduced by synthesizing the appropriate DNA fragment in vitro and amplifying it by polymerase chain reaction (PCR) procedures known per se in the art.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., Proc. Natl. Acad. Sci. (USA), 75: 5765 (1978). This primer is then annealed with the single-stranded protein-sequence-containing vector, and subjected to DNA-polymerizing enzymes such as E. coli polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated region may be removed and placed in an appropriate vector for protein production, generally an expression vector of the type that is typically employed for transformation of an appropriate host.

Most deletions and insertions, and substitutions in particular, are not expected to produce radical changes in the characteristics of the NT-4/5 molecule, and single substitutions will preserve at least one immune epitope in the NT-4/5 polypeptide.

Since it is often difficult to predict in advance the characteristics of a variant NT-4/5, it will be appreciated that some screening will be needed to select the optimal variant. One can screen for enhanced trophic activity, differential neuron cell type specificity, stability in recombinant cell culture or in plasma (e.g. against proteolytic cleavage), possession of antagonist activity, oxidative stability, ability to be secreted in elevated yields, and the like. For example, a change in the immunological character of the NT-4/5 molecule, such as affinity for a given antibody, is measured by a competitive-type immunoassay. Changes in the enhancement or suppression of neurotrophic activities by the candidate mutants are measured by dendrite outgrowth or explant cell survival assays. Modifications of such protein properties as redox or thermal stability, hydrophobicity, susceptibility to proteolytic degradation, or the tendency to aggregate with carriers or into multimers are assayed by methods well known in the art.

Trypsin or other protease cleavage sites are identified by inspection of the encoded amino acid sequence for paired basic residues, e.g. combinations of adjacent arginyl and lysinyl residues. These are rendered inactive to protease by substituting one of the residues with another residue, preferably a basic residue such as glutamine or a hydrophobic residue such as serine; by deleting one or both of the basic residues; by inserting a prolyl residue immediately after the last basic residue; or by inserting another residue between the two basic residues. A variant NT-4/5 typically is made by site-specific mutagenesis of the native NT-4/5-encoding nucleic acid, expression of the variant nucleic acid in recombinant cell culture, and, optionally, purification from the cell culture, for example, by bioassay of the variant's activity or by immunoaffinity adsorption on a rabbit polyclonal anti-NT-4/5 column (to absorb the variant by binding it to at least one remaining immune epitope). Small fragments, on the order of 40 residues or less, are conveniently made by in vitro methods.

The NT-4/5-encoding nucleic acid, whether variant or cDNA, then is ligated into a replicable vector for further cloning or for expression. Vectors are useful for performing two functions in collaboration with compatible host cells (a host-vector system). One function is to facilitate the cloning of the nucleic acid that encodes the NT-4/5, i.e., to produce usable quantities of the nucleic acid. The other function is to direct the expression of NT-4/5. One or both of these functions are performed by the vector-host system. The vectors will contain different components depending upon the function they are to perform as well as the host cell that is selected for cloning or expression.

Each vector will contain nucleic acid that encodes NT-4/5 as described above. Typically, this will be DNA that encodes the NT-4/5 in its mature form linked at its amino terminus to a secretion signal. This secretion signal preferably is the NT-4/5 presequence that normally directs the secretion of NT-4/5 from human cells in vivo. However, suitable secretion signals also include signals from other animal NT-4/5, signals from NGF, NT-2, or NT-3, viral signals, or signals from secreted polypeptides of the same or related species.

If the signal sequence is from another NT molecule, it may be the precursor sequence spanning from the initiating methionine (M) residue of NT-2, NT-3, or NGF up to the arginine (R) residue just before the first amino acid of the mature protein, or a consensus or combination sequence from any two or more of those precursors taking into account homologous regions of the precursors. The DNA for such precursor region is ligated in reading frame to DNA encoding the mature NT-4/5.

Expression and cloning vectors contain a nucleic acid sequence that enables the vector to replicate in one or more selected host cells. Generally, in cloning vectors this sequence is one that enables the vector to replicate independently of the host chromosomes, and includes origins of replication or autonomously replicating sequences. Such sequences are well-known for a variety of bacteria, yeast and viruses. The origin of replication from the well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells. Origins are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA also is cloned by insertion into the host genome. This is readily accomplished with bacillus species, for example, by including in the vector a DNA sequence that is complementary to a sequence found in bacillus genomic DNA. Transfection of bacillus with this vector results in homologous recombination with the genome and insertion of NT-4/5 DNA. However, the recovery of genomic DNA encoding NT-4/5 is more complex than that of an exogenously replicated vector because restriction enzyme digestion is required to excise the NT-4/5 DNA.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b)

complement auxotrophic deficiencies, or (c) supply critical nutrients not available from complex media, e.g. the gene encoding D-alanine racemase for bacilli.

A suitable selection gene for use in yeast is the trp1 gene present in the yeast plasmid YRp7 (Stinchcomb et al., 1979, Nature 282:39; Kingsman et al., 1979, Gene 7:141; or Tschemper et al., 1980, Gene 10:157). The trp1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR) or thymidine kinase. Such markers enable the identification of cells which were competent to take up the NT-4/5 nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes NT-4/5. Amplification is the process by which genes in greater demand for the production of a protein critical for growth are reiterated in tandem within the chromosomes of successive generations of recombinant cells. Increased quantities of NT-4/5 are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, Proc. Nat'l. Acad. Sci. USA 77:4216. A particularly useful DHFR is a mutant DHFR that is highly resistant to MTX (EP 117,060A). This selection agent can be used with any otherwise suitable host, e.g. ATCC No. CCL61 CHO-K1, notwithstanding the presence of endogenous DHFR. The DHFR and NT-4/5-encoding DNA then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding NT-4/5, wild-type DHFR, and another selectable marker such as the neo gene can be identified using a selection agent for the selectable marker such as G418 and then selected and amplified using methotrexate in a wild-type host that contains endogenous DHFR.

Other methods, vectors and host cells suitable for adaptation to the synthesis of NT-4/5 in recombinant vertebrate cell culture are described in M. J. Gething et al., Nature 293:620–625 (1981); N. Mantei et al., Nature 281:40–46 (1979); and A. Levinson et al., EP 117,060A and 117,058A. A particularly useful plasmid for mammalian cell culture expression of NT-4/5 is pRK5 (EP pub. no. 307,247) or pSVI6B (U.S. Ser. No. 07/441,574 filed Nov. 22, 1989).

Expression vectors, unlike cloning vectors, should contain a promoter which is recognized by the host organism and is operably linked to the NT-4/5 nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to NT-4/5-encoding DNA by removing them from their gene of origin by restriction enzyme digestion, followed by insertion 5' to the start codon for NT-4/5. This is not to say that the genomic NT-4/5 promoter is not usable. However, heterologous promoters generally will result in greater transcription and higher yields of expressed NT-4/5.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist then synthetic oligonucleotide adaptors or linkers are used in accord with conventional practice.

Promoters suitable for use with prokaryotic hosts include the β-lactamase and lactose promoter systems (Chang et al., 1978, Nature 275:615; and Goeddel et al., 1979, Nature 281:544), alkaline phosphatase, a tryptophan (trp) promoter system (Goeddel, 1980, Nucleic Acids Res. 8:4057 and EPO Appln. Publ. No. 36,776) and hybrid promoters such as the tac promoter (H. de Boer et al., 1983, Proc. Nat'l. Acad. Sci. USA 80:21–25). However, other known bacterial promoters are suitable. Their nucleotide sequences have been published, thereby enabling a skilled worker operably to ligate them to DNA encoding NT-4/5 (Siebenlist et al 1980, Cell 20:269) using linkers or adaptors to supply any required restriction sites. Promoters for use in bacterial systems also will contain a Shine-Delgamo (S.D.) sequence operably linked to the DNA encoding NT-4/5.

Suitable promoting sequences for use with yeast hosts include the promoters for 3-phosphoglycerate kinase (Hitzeman et al., 1980, J. Biol. Chem. 255:2073) or other glycolytic enzymes (Hess et al., 1968, J. Adv. Enzyme Reg. 7:149; and Holland, 1978, Biochemistry 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

NT-4/5 transcription from vectors in mammalian host cells is controlled by promoters obtained from the genomes of viruses such as polyoma, cytomegalovirus, adenovirus, retroviruses, hepatitis-B virus and most preferably Simian Virus 40 (SV40), or from heterologous mammalian promoters, e.g. the actin promoter. The early and late promoters of the SV40 virus are conveniently obtained as an SV40 restriction fragment which also contains the SV40 viral origin of replication (Fiers et al., 1978, Nature 273:113). Of course, promoters from the host cell or related species also are useful herein.

Transcription of NT-4/5-encoding DNA by higher eukaryotes is increased by inserting an enhancer sequence into the vector. An enhancer is a nucleotide sequence, usually about from 10–300 bp, that acts on a promoter to increase its transcription and does so in a manner that is relatively orientation and position independent. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenoviral enhancers. The enhancer may be spliced into the vector at a position 5' or 3' to the NT-4/5-encoding sequence, but is preferably located at a site 5' from the promoter.

Expression vectors used in eukaryotic host cells (yeast, fungi, insect, plant, animal, human or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain regions that are transcribed as polyadenylated segments in the untranslated portion of the mRNA encoding NT-4/5. The 3' untranslated regions also include transcription termination sites.

Suitable host cells for cloning or expressing the vectors herein are the prokaryote, yeast or higher eukaryote cells described above. Suitable prokaryotes include gram negative or gram positive organisms, for example $E.$ $coli$ or bacilli. A preferred cloning host is $E.$ $coli$ 294 (ATCC 31,446) although other gram negative or gram positive prokaryotes such as $E.$ $coli$ B, $E.$ $coli$ X1776 (ATCC 31,537), $E.$ $coli$ W3110 (ATCC 27,325), pseudomonas species, or $Serratia$ $Marcesans$ are suitable.

In addition to prokaryotes, eukaryotic microbes such as filamentous fungi or yeast are suitable hosts for NT-4/5-encoding vectors. $Saccharomvces$ $cerevisiae,$ or common baker's yeast, is the most commonly used among lower eukaryotic host microorganisms. However, a number of other genera, species and strains are commonly available and useful herein.

Suitable host cells for the expression of NT-4/5 are derived from multicellular organisms. Such host cells are capable of complex processing and glycosylation activities. In principle, any higher eukaryotic cell culture is workable, whether from vertebrate or invertebrate culture, although cells from mammals such as humans are preferred. Propagation of such cells in culture is per se well known. See Tissue Culture, Academic Press, Kruse and Patterson, editors (1973). Examples of useful mammalian host cell lines are VERO and HeLa cells, Chinese hamster ovary cell lines, the WI38, BHK, COS-7, MDCK cell lines and human embryonic kidney cell line 293.

Host cells are transformed with the above-described expression or cloning vectors and cultured in conventional nutrient media modified as is appropriate for inducing promoters or selecting transformants containing amplified genes. The culture conditions, such as temperature, pH and the like, suitably are those previously used with the host cell selected for cloning or expression, as the case may be, and will be apparent to the ordinary artisan.

Covalent modifications of NT-4/5 molecules are included within the scope of this invention. Variant NT-4/5 fragments having up to about 40 residues may be conveniently prepared by in vitro synthesis. In addition, covalent modifications are introduced into the molecule by reacting targeted amino acid residues of the NT-4/5 polypeptide with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; 0-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking NT-4/5 to a water-insoluble support matrix or surface for use in the method for purifying anti-NT-4/5 antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79–86 [1983]), acetylation of the N-terminal amine, and amidation of any C-terminal carboxyl group. NT-4/5 also is covalently linked to nonproteinaceous polymers, e.g. polyethylene glycol, polypropylene glycol or polyoxyalkylenes, in the manner set forth in U.S. Ser. No. 07/275,296 or U.S. Pat. No. 4,640,835; 4,496,689; 4,301,144; 4,670,417; 4,791,192 or 4,179,337.

NT-4/5 preferably is recovered from the culture medium as a secreted protein, although it also may be recovered from host cell lysates when directly expressed without a secretory signal. When NT-4/5 is expressed in a recombinant cell other than one of human origin, the NT-4/5 is thus completely free of proteins of human origin. However, it is necessary to purify NT-4/5 from recombinant cell proteins in order to obtain preparations that are substantially homogeneous as to protein. As a first step, the culture medium or lysate is centrifuged to remove particulate cell debris. NT-4/5 thereafter is purified from contaminant soluble proteins, for example, by fractionation on immunoaffinity or ion exchange columns; ethanol precipitation; reverse phase HPLC; chromatography on silica or on a cation exchange resin such as DEAE; chromatofocusing; SDS-PAGE; ammonium sulfate precipitation; or gel electrophoresis using, for example, Sephadex G-75. NT-4/5 variants in which residues have been deleted, inserted or substituted are recovered in the same fashion as native NT-4/5, taking account of any substantial changes in properties occasioned by the variation. For example, preparation of an NT-4/5 fusion with another protein, e.g. a bacterial or viral antigen, facilitates purification because an immunoaffinity column containing antibody to the antigen can be used to adsorb the fusion. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native NT-4/5 may require modification to account for changes in the character of NT-4/5 or its variants upon expression in recombinant cell culture.

The trkB and trkC receptor DNA sequences are known. The receptors can be expressed to obtain a soluble form of the receptor by identifying the extracellular domain and excising the transmembrane domain therefrom). The soluble form of the receptor can then be used to screen for trkB or trkC binding molecules, preferably small organic molecules, that are candidate agonists for receptor activity. Screening of agonists uses, for example, transformed cells expressing trkB or trkC receptor. Further or alternative screening uses the assays taught herein.

As discussed above variants of native neurotrophins are made that act as agonists. The receptor binding site(s) of a neurotrophin are determined by binding studies. These regions can be subcloned and tested for agonist activity. Such regions can be also be constructed into larger molecules using known protein engineering techniques, such as template-assembly synthesis. Standard mutagenesis techniques (deletion or radical substitution of appropriate nucleic acids) are used to identify such regions and to create mutants for testing for agonism. Agonist activity can be determined by several means, including the assays described herein.

Chimeric or pantropic neurotrophins that bind either trkB or trkC or preferably both are suitable for use in the methods and compositions of the invention. By the term "pantropic neurotrophins" or "pantropic neurotrophic factors", or grammatical equivalents, herein is meant a neurotrophin which, unlike naturally occurring neurotrophins, has multiple neurotrophin specificities. That is, it contains domains which confer different neurotrophin specificities. WO 95/33829 and corresponding U.S. Ser. No. 08/253,937, are hereby incorporated by reference for describing, making and using pantropic neurotrophic factors suitable for practicing the present invention. The discussions herein pertaining to NT-4/5 or pantropic neurotrophin synthesis, design, expression and use apply to chimeric and other neurotrophins as well. In one embodiment, this means that the pantropic neurotrophins of the present invention will bind to a variety of neurotrophic receptors. Thus, for example, naturally occurring NGF, which is the natural or native ligand for the trkA receptor, does not bind appreciably to either the trkB or trkC receptor with high affinity; for example, NGF binds to these receptors with a 500–1000 fold lower $K_D$ than BDNF or NT-3, respectively. However, a pantropic NGF, i.e. a pantropic neurotrophin whose amino acid backbone is based on NGF, may bind to at least the trkA, trkB and p75 receptor. Alternatively, a pantropic NGF will bind to the trkA, trkC and p75 receptor. One preferred embodiment allows the binding of the trkA, trkB, trkC and p75 receptor. Similarly, naturally occurring BDNF and NT-4/5, which are the natural ligands for the trkB receptor, do not bind appreciably to either the trkA or trkC receptor as above. Thus pantropic BDNF or NT-4/5 will bind to trkB and any combination of trkA, trkC and p75, as shown above for pantropic NGF.

In alternative embodiments, the naturally occurring neurotrophin will bind with poor affinity to several neurotrophin receptors. In this embodiment, the pantropic neurotrophin binds to these receptors with affinities higher than normally found, similar to the affinities seen for the natural ligand. For example, NT-3 binds strongly to trkC, and weakly to trkA and trkB. Thus, a pantropic NT-3 binds to trkC with its normal binding affinity, and will bind to either trkA with an affinity similar to the trkA natural ligand, NGF, or to trkB with an affinity similar to the trkB natural ligands BDNF or NT-4/5, or both.

In a preferred embodiment, methods of treatment use a chimeric or pantropic neurotrophin or variant with a binding affinity for neurotrophin receptors at least about 50–60%, preferably about 75–80%, and even more preferably about 90%, and most preferably 100% of the binding affinity of the natural ligand. Thus, a pantropic NGF will bind to the trkB or trkC receptor with at least 50% of the binding of BDNF or NT-4/5, or NT-3, respectively. This affinity is measured by a variety of ways, as will appreciated by those skilled in the art. The preferred method is the use of competition assays, as shown in (Hulme, et al.) and in Example 2. Generally, binding affinities are reported as $IC_{50}$, that is, the concentration of unlabeled competitor which inhibits 50% of the binding of labeled ligand to the receptor.

In alternative embodiments, the pantropicity of the neurotrophin is measured not by binding affinity to neurotrophin receptors, but rather by the neuronal survival or neurite outgrowth assays. Thus, all neurotrophins support the survival of embryonic neural crest-derived sensory neurons. Survival of embryonic sympathetic neurons is only supported by NGF, while survival of placode-derived sensory neurons is supported by NT-3 and BDNF (Grotz et al., 1992). Survival of sensory neurons of the dorsal root ganglion is supported by both NGF and BDNF. NT-3 elicits neurite outgrowth of sensory neurons from dorsal root ganglion, sympathetic chain ganglia, and nodose ganglion, as well as supports survival of nodose ganglia neurons and dorsal root ganglion neurons. Thus, neuronal survival assays or neurite outgrowth assays can be run to determine the pantropicity of the pantropic neurotrophins.

Thus, neurotrophin specificity is determined by the neurotrophin receptor binding, and the neuronal survival assays and/or neurite outgrowth assays. Thus, a pantropic neurotrophin with NGF specificity means a neurotrophin which exhibits at least the binding characteristics, neuronal survival assay specificity, or the neurite outgrowth assay specificity of NGF. Similarly, a pantropic neurotrophin with BDNF, NT-3 or NT-4/5 specificity exhibits at least the binding characteristics, neuron survival assay specificity, or neurite outgrowth assay specificity of BDNF, NT-3 or NT-4/5, respectively.

In an additional embodiment, pantropic neurotrophins are made by constructing covalent heterodimers. Normally, neurotrophins are homodimers, comprising two identical monomers which are non-covalently associated. In this embodiment, as outlined below, pantropicity is conferred by each monomer containing domains which confer different neurotrophic specificity. Alternatively, pantropicity may be created by covalently attaching two different neurotrophins with different specificities to create a covalent heterodimer. Thus, for example, a NGF monomer may be covalently attached to a NT-3 monomer, resulting in a pantropic neurotrophin with both NGF and NT-3 specificity. Similarly, covalent heterodimers may be made with any combination of NGF, NT-3, NT-4/5, BDNF or CNTF to create pantropic neurotrophins with at least two specificities. In addition, this procedure may be done with monomers which are themselves pantropic, resulting in covalent dimers of any combination of pantropic and single specificity monomers. Thus, a pantropic covalent dimer may be a homodimer of two pantropic monomers. However, to be included within the definition of the present invention, the pantropic covalent dimer must have at least two, and preferably three, neurotrophin specificities.

The covalent attachment is preferably done as a direct fusion of the nucleic acid, such that when the protein is expressed, the C-terminus of the first monomer is attached directly to the N-terminus of the second monomer, creating a single nucleic acid encoding the dimer. In alternative embodiments, a linker may be used, such as short repeats of glycine, or glycine and serine; for example, a linker such as gly-gly or gly-gly-ser-gly-gly may be used. This is done using techniques well known in the art. Other techniques for the covalent attachment of proteins are well known in the art.

Pantropic neurotrophins accomplish pantropic binding, or, as discussed above, pantropic neuronal survival, by containing domains which confer neurotrophin receptor specificity or binding. A domain may be defined in one of two ways. In the first embodiment, a domain is a portion of the neurotrophin which confers some neurotrophic specificity. In this embodiment, a single monomer of the pantropic neurotrophin contains one or several domains which confer different specificities. The domains can range in size from a single amino acid to about 10–15 amino acids. The domain may be comprised of a combination of amino acids from a different neurotrophin than the host neurotrophin, i.e. a domain from one neurotrophin may be substituted into a second neurotrophin, conferring pantropicity to the second neurotrophin. Alternatively, the domain may result from amino acid substitutions which are not based on homology to existing neurotrophins, as outlined below. In the preferred embodiment, the domain comprises a continuous sequence of amino acids; that is, a single stretch of amino acids is replaced. In other embodiments, the domain may be comprised of discontinuous amino acids; for example, several regions within the neurotrophin may confer specificity, and thus replacements at several positions within the neurotrophin are necessary for pantropicity.

In some embodiments, there is more than one domain within a neurotrophin which can confer neurotrophic specificity, which will depend on the particular neurotrophin. BDNF, for example, has a number of domains which appear to confer BDNF specificity. The present invention shows that a single amino acid change in NT-3, from aspartic acid at position 15 to an alanine, confers BDNF specificity to NT-3. This domain can also be imported into the NGF and NT-4/5 sequences at the positions that correspond to position 15 in NT-3; i.e. position 16 in NGF or position 18 in NT-4/5. It should be understood that the corresponding amino acids are determined by an examination of the alignment of the sequences as depicted in U.S. Pat. No. 5,364,769. In addition to this domain, there are other domains within BDNF which confer BDNF specificity. For example, the substitution of the BDNF sequence from positions 78 to 88 (QCRTTQSYVR), or from positions 93–99 (SKKRIG) may confer BDNF specificity (55).

Similarly, NT-3 has a number of domains which may confer NT-3 specificity when substituted into a different neurotrophin. A number of residues of NT-3 have been shown to be important in NT-3 trkC receptor binding as well as bioactivity assays. Specifically, mutations at positions R103, D105, K80, Q83, E54, R56, T22, Y51, V97, Y11, E7, R8, E10 and R68 all contribute to NT-3 specificity, since mutations at these positions in NT-3 cause decreases in NT-3 activity. Of these, K80, Q83, T22, and V97 are within variable regions, and the rest are found within constant regions. In addition, residues in the vicinity of the residues may also give NT-3 specificity. In some embodiments, changes in the constant regions may also give NT-3 specificity. Alternatively, mutations at positions R31 and E92 caused increases in NT-3 binding; specifically, R31A and E92A NT-3 showed increased trkC binding. These mutations can be directly imported into neurotrophins besides NT-3, using the procedures described below. The amino acids at any of these positions may be changed, as outlined below.

NGF has a number of domains which may confer NGF specificity when substituted into a different neurotrophin. The N-terminal amino acids of NGF confer NGF specificity when substituted for the N-terminal residues of NT-3. Specifically, the 7 N-terminal amino acids (SSSHPIF) of NGF may be substituted for the 6 N-terminal amino acids of NT-3 (YAEHKS), resulting in a pantropic NT-3 with NGF specificity. The exact number of NGF N-terminal residues is not crucial; as shown in the Examples, and particularly in Example 3, the histidine at amino acid position 4 appears to be quite important for NGF specificity; thus from about 4 to about 10 N-terminal residues may be exchanged although in some embodiments, a single amino acid change will be sufficient. Similarly, a number of other residues of NGF have been shown to be important in NGF trkA receptor binding as well as bioactivity assays. For example, there are a number of residues which, when mutated, lose NGF activity. This shows the importance of the residue for NGF specificity. These residues include, but are not limited to, H4, P5, V18, V20, G23, D30, Y52, R59, R69, H75, Y79, T81, and R103. Of these, D30, R59, Y79, and T81 are in "variable regions", i.e. regions which vary between the different neurotrophins, with the remainder in constant regions. In some embodiments, the variable region residues are more likely to cause NGF specificity, since constant region residues may be important for general structure and characteristics, and may not confer specificity. However, as shown above for the D15A mutation, mutations in the constant regions can confer specificity as well. Furthermore, there are a number of amino acid substitutions in NGF which increase NGF binding and/or bioactivity. Accordingly, these substitutions may be imported into other neurotrophin backbones to confer NGF specificity. These residues include, but are not limited to, E11, F12, D24, E41, N46, S47, K57, D72, N77, H84, D105, and K115.

Once identified, the residues important in neurotrophin specificity can be replaced by any of the other amino acid residues using techniques described in the examples and well-known techniques for site-directed mutagenesis. Generally, the amino acids to be substituted are chosen on the basis of characteristics understood by those skilled in the art. For example, when small alterations in the characteristics are desired, substitutions are generally made as discussed above.

In the context of a covalent heterodimer, a domain may also refer to the entire neurotrophin monomer. Thus, a pantropic covalent heterodimer can be comprised of a domain which confers NT-3 specificity, i.e. the NT-3 monomer, covalently attached to a domain that confers BDNF specificity, i.e. the BDNF monomer. Similarly, an NT-3 monomer may be paired with an NGF monomer, or an NGF monomer may be paired with a BDNF monomer. In addition, covalent heterodimers may be made with NT-4/5 and CNTF monomers as well. In these embodiments, the domain is large, and generally comprises most or all of the wild-type neurotrophin amino acid sequence.

In one embodiment, the agonist is a pantropic or chimeric NT-3. In this context, a pantropic NT-3 is a pantropic neurotrophin which has an amino acid sequence homologous to the amino acid sequence of NT-3, with domains which confer other neurotrophin specificities. In the preferred embodiment, the domains are substituted for NT-3 residues; that is, some number of amino acids are deleted from the NT-3 sequence, and an identical or similar number of amino acids are substituted, conferring an additional specificity. For example, the MNTS-1 (multiple neurotrophic specificities-1) pantropic NT-3 comprises the first 7 amino acids of NGF replacing the 6 N-terminal residues of NT-3, plus the D15A substitution. The MNTS-1 pantropic NT-3 has NT-3, NGF, and BDNF specificities, and also binds to the p75 receptor. Other pantropic NT-3s are made using minimal changes within the N-terminus. For example, since H4 and P5 are conserved among NGFs, and 2 hydrophobic residues in positions 6 and 7 are conserved, the following variants are made: 1) YASHPIF-hNT-3; 2) YAHPIF-hNT-3; 3) YASHPIS-hNT-3; 4) YAEHPIF-hNT-3; 5) YAQHPIF-hNT-3. When the D15A substitution is added, the resulting neurotrophins exhibit NGF, NT-3 and BDNF specificity. Alternatively, replacing the variable region 2 or 3 or 4, or combinations, of NT-3 with the corresponding region from NGF gives a pantropic neurotrophin with both NT-3 and NGF specificity.

A pantropic NGF can be made with a D16A substitution, which confers BDNF specificity, plus substitutions in the pre-variable region 1 (V18E+V20L+G23T) and in variable region 4 (Y79Q+T81K+H84Q+F86Y+K88R). Alternatively, the substitutions in the pre-variable region 1 can be made with only single amino acid substitutions in variable region 4; for example, V18E+V20L+G23T and one of Y79Q, T81K, H84Q, F86Y, or K88R may be made.

In a preferred embodiment, the agonist is a chimeric or pantropic NT-4/5, preferably made with a trkC binding region. NGF specificity may be conferred on NT- 4/5 by replacing the N-terminal 9 amino acids of NT-4/5 with the N-terminal 7 amino acids of NGF.

In one embodiment, binding to the p75 receptor by the pantropic neurotrophin has been substantially diminished or eliminated. For example, there are a variety of amino acid residues which contribute to p75 binding, in which mutations result in diminished p75 binding. In NT-3, mutations at positions R68, Y11, K73, R114, K115, Y51, K73, R31 and H33 and in NGF, mutations at positions F12, I31, K32, K34, K50, Y52, R69, K74, K88, L112, S113, R114, and K115 all result in diminished p75 binding. Since F12, I31, K50, Y52, R69, and K74 are all within constant regions of the neurotrophins; these changes are expected to alter p75 binding in the other neurotrophins as well. The other residues may be altered as well.

In addition to the amino acid changes outlined above, those skilled in the art understand that some variability of the amino acid sequence is tolerated without altering the specificity and characteristics of the neurotrophin. Thus, pantropic neurotrophins can have amino acid substitutions, insertions or deletions compared to the wild-type sequences which do not affect pantropicity but are merely variations of the sequence. In some embodiments, these mutations will be found within the same positions identified as important to specificity; i.e. in some cases, neutral mutations may be made without changing neurotrophin specificity.

The pantropic neurotrophins of the present invention can be made in a variety of ways, using recombinant technology as discussed above. In a preferred embodiment, the pantropic neurotrophins of the invention are expressed in mammalian cells. Mammalian expression systems are also known in the art. In one embodiment, pantropic neurotrophins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* The methods of introducing exogenous nucleic acid into yeast hosts, as well as other hosts, is well known in the art, and will vary with the host cell used. In a preferred embodiment, pantropic neurotrophins are expressed in bacterial systems. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others. In one embodiment, pantropic neurotrophins are produced in insect cells. Expression vectors for the transformation of insect cells, and in particular, baculovirus-based expression vectors, are well known in the art. Materials and methods for baculovirus/insect cell expression systems are commercially available in kit form; for example the "MaxBac" kit from Invitrogen in San Diego. Recombinant baculovirus expression vectors have been developed for infection into several insect cells. For example, recombinant baculoviruses have been developed for *Aedes aegypti, Autographa californica, Bombyx mori, Drosophila melangaster, Spodoptera frugiperda,* and *Trichoplusia ni.*

Once expressed, chimeric or pantropic neurotrophins are used as neurotrophic factors. These chimeric or pantropic neurotrophins may be utilized in various compositions, assays, and therapeutic applications of the invention.

For use in the assays of the invention the agonist can be labeled. By "labeled" herein is meant an agonist that has at least one element, isotope or chemical compound attached to enable the detection of the neurotrophin bound to a neurotrophin receptor. In general, labels fall into three classes: a) isotopic labels, which may be radioactive or heavy isotopes; b) immune labels, which may be antibodies or antigens; and c) colored or fluorescent dyes. The labels may be incorporated into the neurotrophin at any position. Once labelled, the neurotrophins are used to detect neurotrophin receptors, either in vitro or in vivo. For example, the presence of neurotrophin receptors can be an indication of the presence of certain cell types, useful establishing and in scoring the assays. That is, a subpopulation of certain cell types may be shown by the binding of the labeled neurotrophin to the cells via the receptors.

Additionally, the neurotrophins are useful as standards in assays of the invention. For example, the activity of a variant neurotrophin in any particular assay may be determined using known neurotrophin standards, and then the variant neurotrophin may be used in the diagnosis and quantification of neurotrophins and other agonists.

As will be understood by those skilled in the art, the pantropic neurotrophins of the present invention can replace other neurotrophic factors which are used as media components in the cultures as taught herein and in the methods of treatment taught herein. The amount of the pantropic neurotrophins to be added can be easily determined using standard assays.

Purification of Agonists

Techniques used for separating the agonist from impurities depend on which particular agonist is being employed. These procedures may include, for example, one or more steps selected from immunoaffinity chromatography, ion-exchange column fractionation (e.g., on DEAE or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the trkB or trkC agonist, such as trkB or trkC receptors or antibody-affinity, and ethanol or ammonium sulfate precipitation. A protease inhibitor may be included in any of the foregoing steps to inhibit proteolysis. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin, and benzamidine.

Therapeutic Compositions and Administration of Agonists

Agonists to trkB or trkC alone, in combination with each other, or optionally in combination with ototoxic pharmaceuticals, are believed to find use as drugs for in vivo treatment of mammals, ex vivo treatments involving transplant or assays involving organs such as during perfusion, and in vitro assays and screening methods. For example, the trkB or trkC agonist alone or in combination with each other will be useful in treating hearing impairments in cases where pharmaceutical drugs are limited in their dosage or display side-effect of a oto-neurological hearing impairment.

In the preferred embodiment, the neurotrophin(s) is administered to a patient to treat neural-related (associated with neuron degeneration, damage or loss) hearing impairment, prophylactically or therapeutically. Preferably hair cell loss or damage is not present or not at a significant level that would hinder hearing recovery. Specific examples include, but are not limited to neuropathies, and other conditions characterized by necrosis, damage, or loss of neurons affecting hearing, whether caused by trauma, injury, aging, noise, environmental toxins, or ototoxic pharmaceutical drugs. For example, neuropathies associated with certain conditions such as diabetes, AIDS, or chemotherapy may be treated using the compositions and methods of the present invention.

Therapeutic formulations of agonist(s) (and optionally ototoxic pharmaceutical drug) for treating hearing impairments are prepared for storage by mixing the agonist(s) or drug having the desired degree of purity with optional physiologically acceptable carriers, excipients, or stabilizers (Remington's Pharmaceutical Sciences, 16th edition, Oslo, A., Ed., [1980]), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics, or polyethylene glycol (PEG).

The agonist(s) are also suitably linked to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

The agonist(s) to be used for in vivo administration must be sterile. This is readily accomplished by filtration through sterile filtration membranes, prior to or following lyophilization and reconstitution. The agonist(s) ordinarily will be stored in lyophilized form or in solution. Preferably, it is free or substantially free (at least 80%, preferably at least 90%, more preferably at least 95%, and even more preferably at least 99% pure) of contaminating polypeptides from the purification source.

Therapeutic agonist compositions generally are placed into a container having a sterile access port, for example, an intravenous solution bag or vial having a stopper pierceable by a hypodermic injection needle.

The agonist(s) is administered in an acute or chronic fashion, as may be required, for prophylactic and therapeutic applications, by a number of routes including: injection or infusion by intravenous, intraperitoneal, intracerebral, intramuscular, intradermally, intraocular, intraarterial, subcutaneously, or intralesional routes, topical administration, orally if an orally active small molecule is employed, using sustained-release systems as noted below, or by an indwelling catheter using a continuous administration means such as a pump, by patch, or implant systems, e.g., intracerebral implantation of a sustained-release vehicle. Agonist(s) is administered continuously by infusion or by periodic bolus injection if the clearance rate is sufficiently slow, or by administration into the blood stream, lymph, CNS or spinal fluid. A preferred administration mode is directly to the affected portion of the ear or vestibule, topically, and, preferably to the affected neurons, so as to direct the molecule to the source and minimize side effects of the agonists.

Neurotrophin, preferably NT-4/5, can be injected through chronically implanted cannulas or chronically infused with the help of osmotic minipumps. Subcutaneous pumps are available that deliver proteins through a small tubing to the appropriate area. Highly sophisticated pumps can be refilled through the skin and their delivery rate can be set without surgical intervention. Examples of suitable administration protocols and delivery systems involving a subcutaneous pump device or continuous infusion through a totally implanted drug delivery system are those used for the administration of dopamine, dopamine agonists, and cholinergic agonists to Alzheimer patients and animal models for Parkinson's disease described by Harbaugh, J. Neural Transm. Suppl., 24: 271–277 (1987) and DeYebenes et al., Mov. Disord., 2: 143–158 (1987), the disclosures of which are incorporated herein by reference. It is envisioned that it may be possible to introduce cells actively producing agonist into areas in need of increased concentrations of agonist.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res., 15: 167–277 [1981] and Langer, Chem. Tech., 12: 98–105 [1982] or poly (vinylalcohol)), polylactides (U.S. Pat. No. 3,773,919, EP 58,481), copolymers of L-glutamic acid and gamma ethyl-L-glutamate (Sidman et al., Biopolymers, 22: 547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133, 988). The agonist(s) also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, micro emulsions, nano-particles and nanocapsules), or in macroemulsions. Such techniques are disclosed in Remington's Pharmaceutical Sciences, 16th edition, Osol, A., Ed., (1980).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release agonist(s) compositions also include liposomally entrapped agonist(s). Liposomes containing agonist(s) are prepared by methods known per se: DE 3,218,121; Epstein et al., Proc. Natl. Acad. Sci. USA, 82: 3688–3692 (1985); Hwang et al., Proc. Natl. Acad. Sci. USA, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal agonist therapy. A specific example of a suitable sustained-release formulation is in EP 647,449.

An effective amount of agonist(s) to be employed therapeutically will depend, for example, upon the therapeutic objectives, the route of administration, the species of the patient, and the condition of the patient. Accordingly, it will be necessary for the therapist to titer the dosage and modify the route of administration as required to obtain the optimal therapeutic effect. As is known in the art, adjustments for age as well as the body weight, general health, sex, diet, time of administration, drug interaction and the severity of the disease may be necessary, and will be ascertainable with routine experimentation by those skilled in the art. A typical daily dosage of trkB or trkC agonist used alone might range from about 1 μg/kg to up to 100 mg/kg of patient body weight or more per day, depending on the factors mentioned above, preferably about 10 μg/kg/day to 10 mg/kg/day. Typically, the clinician will administer agonist until a dosage is reached that repairs, maintains, and, optimally, reestablishes neuron function to relieve the hearing impairment. Generally, the agonist is formulated and delivered to the target site at a dosage capable of establishing at the site an agonist level greater than about 0.1 ng/ml, more typically from about 0.1 ng/ml to 5 mg/ml, preferably from about 1 to 2000 ng/ml. In a specific embodiment of the invention, a effective pharmaceutical composition, for example for promoting the survival of SGNs, may provide a local neurotrophin protein concentration of between about 1 and 100 ng/ml, preferably 5 to 25 ng/ml, and more preferably, between 10 and 20 ng/ml. The progress of this therapy is easily monitored by conventional assays and neurological diagnostic methods.

If two agonists are administered together, they need not be administered by the same route, nor in the same formulation. However, they can be combined into one formulation as desired. In a preferred embodiment NT-4/5 optionally is combined with or administered in concert with or formed as a pantropic neurotrophin with a neurotrophic agonist to trkC. Both agonists can be administered to the patient, each in effective amounts, or each in amounts that are sub-optimal but when combined are effective. Preferably such amounts are about 10 μg/kg/day to 10 mg/kg/day of each. In another preferred embodiment, the administration of both agonists is by injection using, e.g., intravenous or subcutaneous means, depending on the type of agonist employed. Typically, the clinician will administer the agonist(s) until a dosage is reached that achieves the desired effect for treatment of the hearing impairment. The progress of this therapy is easily monitored by conventional assays.

The two types of agonists, if used together, may be formulated together in an appropriate carrier vehicle to form a pharmaceutical composition that preferably does not contain cells. In one embodiment, the buffer used for formulation will depend on whether the composition will be employed immediately upon mixing or stored for later use, since long-term storage may bring into issue stability such as solubility and aggregation that can be addressed by altering the pH. The final preparation may be a stable liquid or lyophilized solid.

The agonist(s) optionally is combined with or administered in concert with ototoxic pharmaceutical drugs. Initially the drugs are administered in conventional therapies known for the ototoxic pharmaceutical. Adjustments to the therapies are at the discretion of the skilled therapist to titrate dosages and conditions that decrease ototoxicity-related hearing while maintaining, and preferably improving, treatment outcomes with the ototoxic pharmaceutical drug.

Accordingly, methods for preventing or reducing ototoxicity of an aminoglycoside antibiotic or other ototoxic pharmaceutical are disclosed herein, which comprise the administration of an effective dose of a trkB or trkC agonist. In addition, provided herein are compositions having reduced ototoxicity as a result of incorporation of the ototoxicity-inhibiting trkB or trkC agonists of the present invention. These pharmaceutical compositions comprise an effective ototoxicity-inhibiting amounts of agonists as described herein, therapeutically effective amounts of the ototoxic pharmaceutical drug, e.g. aminoglycosides antibiotic, anti-neoplastic agent such as cisplatin, and optionally a pharmaceutically acceptable carrier and/or vehicle which would be familiar to one skilled in the pharmaceutical arts. The actual amounts of ototoxic pharmaceutical drug employed will range from those given in standard references for prescription drugs, e.g. "Physicians Desk Reference" (1995), "Drug Evaluations" AMA, 6th Edition (1986); to amounts somewhat larger since the ototoxicity potential is reduced in these compositions.

The effective amounts of such agents, if employed, will be at the physician's or veterinarian's discretion. Dosage administration and adjustment is done to achieve the best management of hearing (and when used in conjunction with an ototoxic pharmaceutical drug, the indication for the ototoxic drug). The dose will additionally depend on such factors as the type of drug used and the specific patient being treated. Typically the amount employed will be the same dose as that used if the drug were to be administered without agonist; however, lower doses may be employed depending on such factors as the presence of side-effects, the condition being treated, the type of patient, and the type of agonist and drug, provided the total amount of agents provides an effective dose for the condition being treated. For example, a test dose may be 5 mg, which is then ramped up to 10–20 mg per day, once a day, to 25 mg twice per day (BID) or three times per day (TID), and may be titrated to 50 mg BID or TID as the patient tolerates it. Tolerance level is estimated by determining whether decrease in hearing impairment is accompanied by signs of observed side-effects. A discussion of the dosage, administration, indications and contraindications associated with ototoxic pharmaceuticals optionally used with the neurotrophins in the methods of the invention can be found in the *Physicians Desk Reference,* Medical Economics Data Production Co., Montvale, N.J. (1995).

In preferred embodiments therapeutic formulations contain NT-4/5, a fragment, variant, or pantropic, and can be prepared for storage by mixing NT-4/5 having the desired degree of purity with optional physiologically acceptable carriers, excipients or stabilizers (Remington's Pharmaceutical Sciences, supra,) in the form of lyophilized cake or aqueous solutions.

The compositions herein also can suitably contain other growth factors, most preferably hair cell growth factors, or combination of factors, for example retinoic acid or retinoic acid in combination with TGF-α. Such growth factors, including peptide growth factors, are suitably present in an amount that is effective for the purpose intended, i.e., to promote survival, growth, proliferation, regeneration, restoration or recovery of hair cells when desired, and optionally, to enhance growth or recovery of auditory neurons, e.g., spiral ganglia. Although the present results indicate that particular neurotrophins have strong protective effects on SGNs, they did not protect hair cells from the ototoxic drugs. Accordingly, if hair cell loss due to ototoxicity is significant, hearing impairment recovery can be improved by new hair cell growth, survival, proliferation, or regeneration. While not to be constrained by the mechanism forwarded, it is believed that two mechanisms may be available damage of hair cells by aminoglycosides (Lim, 1986; Rybak, 1986). One is the reversible blockage of transduction channels on the hair cells. The other mechanism is impairment of the cell maintenance machinery required for cell repair and survival. The latter is believed to be irreversible and probably occurs intracellularly through a mechanism which inhibits certain enzymes such as phosphatidylinositol phospholipase C, affecting degradation of phospholipids and membrane permeability (Schacht, 1986; Au et al., 1987). Agents that antagonize the reversible blockage of transduction channels on the hair cells, by aminoglycosides for example, are suitable for use in the compositions of the invention and methods of their use. Agents that antagonize ototoxin-induced membrane permeability changes of hair cells, by aminoglycosides for example, are suitable for use in the compositions of the invention and methods of their use. Agents that promote the growth or proliferation of new hair cells, agents that support survival of hair cells, and agents that support regeneration of hair cells are suitable for use in the compositions of the invention and in methods of their use. Recent studies have suggested possible candidates (Forge et al., 1993; Cotanche and Lee, 1994; Tsue et al., 1994a; Cotanche and Lee, 1994; Kelley et al., 1995). For example, diffusible factors such as TGF-α and EGF (Lambert, 1994; Yamashita and Oesterle, 1995) or components derived from antibiotic treated inner ear tissue (Tsue et al., 1994b) stimulate proliferation of supporting cells. Retinoic acid alone or in combination with TGF-α facilitates hair cell regeneration in vitro (Lefebvre et al., 1993, 1995).

The effectiveness of treating hearing impairments with the methods of the invention can be evaluated by the following signs of recovery, including recovery of normal hearing function, which can be assessed by known diagnostic techniques including those discussed herein, and normalization of nerve conduction velocity, which is assessed electrophysiologically.

In another embodiment, agonist compositions of the invention are used during clinical cochlear implants to keep or improve viability of spiral ganglion neurons. Preferably a combination of a trkB and a trkC neurotrophin and a hair cell growth factor(s) will be used, either alone or in combination with a cochlear implant.

Cochlear Explants

In one embodiment of the invention is provided a method of assaying for a trkB or trkC agonist that provides spiral ganglion neuron protection or survival from an ototoxin. The assay steps include culturing a cochlear explant, administering a trkB or trkC agonist to the culture, administering an ototoxin to the culture, and determining the amount of protection or survival compared to a control culture to which the trkB or trkC agonist was not administered.

In a preferred embodiment of the invention is provided an organotype cochlear explant culture that utilizes a 3-D collagen matrix cultures and maintains its normal, in vivo architecture to provide an auditory assay system. The spiral ganglion remain attached. The explant is cultured in three-dimensional ("3-D") collagen gel in serum free medium.

Embedding the cochlear explants in the 3-D collagen was better for maintaining their normal architecture than floating the explants or placing the explants on a monolayer substrate, since the explant tissue could be kept unfolded and cell migration out of the tissue could be limited. By using neurofilament (N52) and phalloidin-FITC conjugate double labeling, the integrity of SGNs and the hair cells in the cochlea was demonstrated. Cochlear explants prepared according to the invention maintained normal architecture in the 3-D collagen gel cultures as observed by Nomarski micrographs. The SGNs remained in their normal locations. No gross cell death of SGNs or hair cells occurred under this culture condition. The peripheral axons of the SGNs which innervate the hair cells in the organ of Corti were seen to maintain consistently a radial projection pattern, as seen in vivo.

Organotypic cultures of postnatal cochlear explants provided herein, in which the afferent innervation of hair cells by primary auditory neurons are intact, are useful to examine ototoxicity of different classes of ototoxins, including ototoxic pharmaceutical drugs, for example, salicylate, gentamicin, and cisplatin, and to search for or test candidate agents that protect against the ototoxic effect. To determine if an ototoxin is able to induce degeneration of SGNs and/or hair cells in the cochlear explant cultures, the ototoxin, preferably an ototoxic pharmaceutical drug, is added at different concentrations to the culture after allowing the culture to recover from the in vitro explant. Histochemical double-labeling of the cochlear explant cultures with a neurofilament antibody (Texas red-mediated) and phalloidin (FITC-conjugated) can be used to compare control cultures (untreated) with cultures treated with ototoxin. While the neurofilament antibody (Texas red-mediated) labels the somata and peripheral axons of SGNs, the phalloidin-FITC conjugate stains the stereocilia bundles of hair cells. Cell count of the remaining hair cells and SGNs can be done to determine and quantify ototoxic effect. Since the density of the axons of SGNs is a reliable index of the number of surviving SGNs, in one embodiment the number of the SGN axons from a given length (e.g., 100 $\mu$m) in the middle of the cochlea is counted. Phalloidin-labeled hair cells can also be counted in the same way.

Organotypic culture of cochlear explants offers advantages to explore the mechanism of actions of ototoxins (Anniko and Sobin, 1986), to discover protective agents (Richardson and Russell, 1991) and to search for hair cell growth factors (Lefebvre et al., 1993), as it keeps the afferent neuronal innervation of hair cells intact and appears to follow closely the normal development pathway (Sobkowicz et al., 1975; Kelley et al., 1993; Rastel et al., 1993; Kelley et al., 1995). According to the present invention, provided herein is a reliable, rapid, and facile method of testing the effects of ototoxic agents and the drugs that prevent, reduce or treat these ototoxic effects. As exemplified herein an organotypic culturing of postnatal cochlear explants in a 3-D collagen matrix in well defined, serum-free medium provides these advantages without the need for a cumbersome Maximov slide assembly (Sobkowicz et al., 1975; Rastel et al., 1993) or undefined medium. Embedding the cochlear explants in the 3-D collagen was better for maintaining the normal architecture than floating the explants or placing the explants on a monolayer substrate, since the explant tissue could be kept unfolded and cell migration out of the tissue could be limited.

The protective effect of a trkB or trkC agonist, preferably a neurotrophin, against ototoxicity can be readily determined in the organotypic cultures of postnatal cochlear explants described herein. The explants and methods of the invention can be used to find agents that can protect SGNs and hair cells from an ototoxin. The protective agonist can be added prior to, concomitant with, or subsequent to addition of the ototoxin to the culture.

The following examples are offered by way of illustration and not by way of limitation. The disclosures of all citations in the specification are expressly incorporated herein by reference.

EXAMPLES

Example I

NT-4/5 is a Potent and Specific Survival Factor for SGNs in Culture

The effects of trkB or trkC agonists to enhance neuronal survival was determined using SGNs in cell culture. Texas red microscopy was used to show neurofilament immunohistochemistry on wholemount of P5 cochlear tissue. When cochlear tissue containing both the spiral ganglion and organ of Corti was immunolabeled with the monoclonal antibody N52 against neurofilament protein (200 kd), the somata and processes of the SGNs were intensively stained. Neuronal innervations of hair cells in the organ of Corti from the cell somata in the spiral ganglion were easily seen. Since both the somata and processes of SGNs were heavily labeled and their innervation of hair cells was evident, this antibody was used to identify SGNs in the dissociated cell cultures.

Bright field microscopy was used to demonstrate neurofilament protein immunocytochemistry in the SGN cultures in serum-free medium alone or in medium containing 10 ng/ml of NT-4/5, respectively. Identical results (not shown) were also obtained with a different neuronal marker, a monoclonal antibody 3A10 (Furley et al., 1990). SGNs were dissociated from postnatal day 5 (P5) rat cochleae and plated in defined serum-free medium. After spiral ligament and stria vascularis tissues were removed, the remaining spiral ganglia were incubated in a mixture of 0.125% trypsin and 0.125% collagenase for 25 min at 37° C. The enzyme was inactivated with a mixture of 0.005% soybean trypsin inhibitor (Sigma) and 0.005% DNase (Worthington) before trituration with 0.05% DNase in Eagle's Basal Medium ("BME"). The dissociated cells were preplated on a 35 mm untreated tissue culture dish for 25 min to enrich the neuronal population. Under these experimental procedures, about 10% of the cell population were spiral ganglion neurons ("SGNs") as determined by immunocytochemistry with a monoclonal antibody (N52; Boehringer) against neurofilaments (200 kd; Boehringer). The cell suspension was finally plated on polylysine (500 $\mu$g/ml)/laminin (10 $\mu$g/ml) coated 16-well LabTek slides in 200 $\mu$l of serum-free medium (BME plus insulin-transferrin-sodium selenite media supplement (Sigma I-1884), 1% BSA, 2 mM glutamine, and 5 mg/ml glucose) without antibiotics as modified from Baired et al. (1992). Cells were plated at a density of 80,000/well. In control cultures about 75% of SGNs died after 2 days, presumably due to a lack of growth factors. Addition of NT-4/5 to the culture greatly enhanced the number of surviving SGNs in a dose-dependent manner (FIG. 1). A wide range of doses (from 0.1 ng/ml to 50 ng/ml) were tested and a maximal effect of approximately 3-fold increase was seen at a concentration of 10 ng/ml. Neurofilament immunocytochemical staining revealed that cultured SGNs showed bipolar or Y-shaped branching patterns, as seen in vivo.

Figure 2:
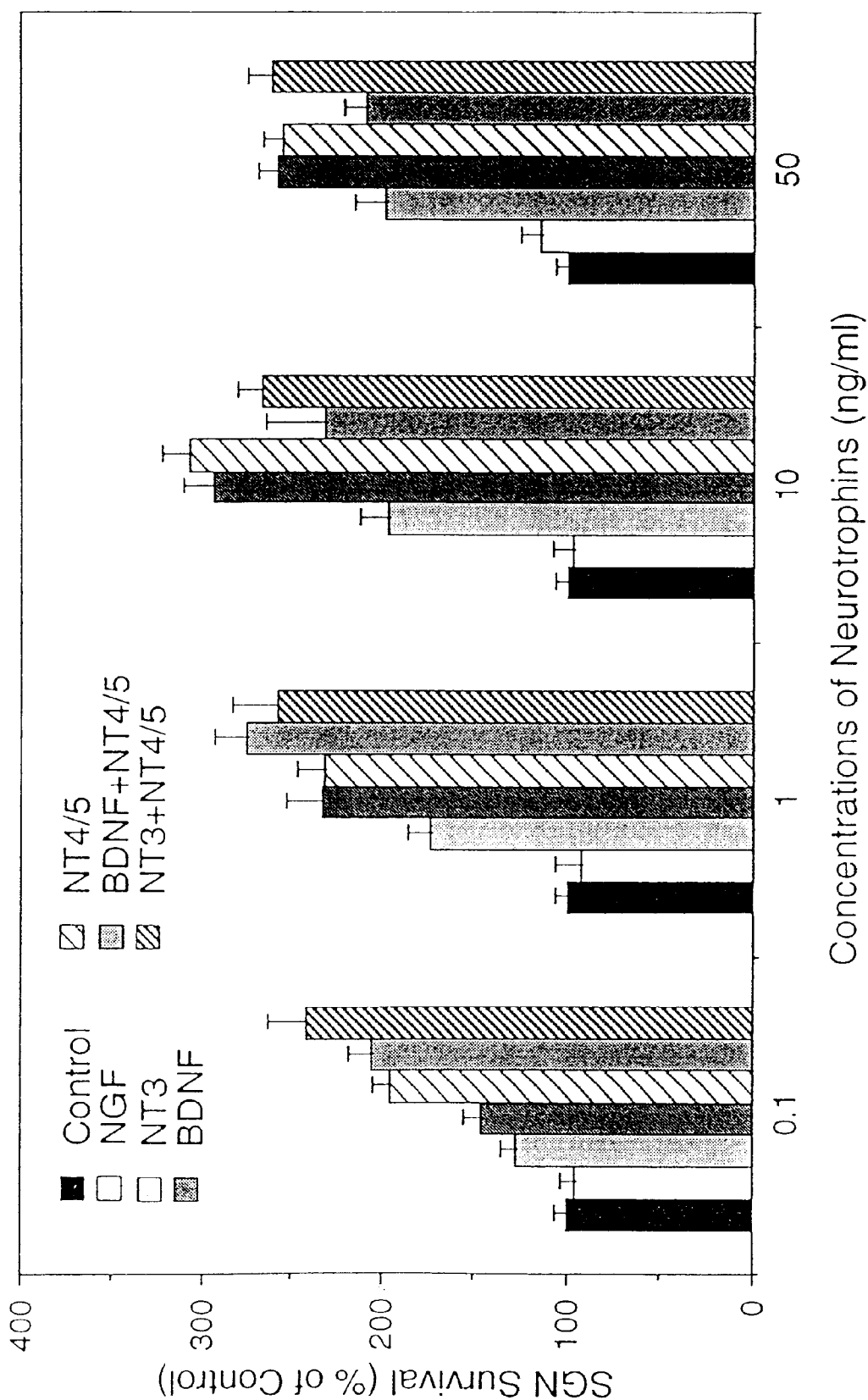
FIG. 2 is a histogram depicting the effects of different neurotrophins on SGN survival. SGNs were prepared from P5 rats and maintained for 2 days in serum-free medium without or with different neurotrophins at different concentrations. Quantitation of viable SGNs was made in the same way as in FIG. 1 and the error bars are SEM. When compared to control cultures, NT-4/5 and BDNF showed very significant survival-promoting effects on SGNs at all doses (P<0.001, 2-tailed, unpaired t-test). NT-3 also showed significant effects (P<0.05 at 0.1 ng/ml; P<0.001 at doses from 1 to 50 ng/ml). Difference between NT-3 and NT-4/5 or BDNF was very significant at all doses (P<0.001). No statistical difference was found between NT-4/5 and BDNF except the dose of 0.1 ng/ml (P<0.01).

Effects of other neurotrophins including NGF, BDNF, and NT-3 on SGN survival in vitro were examined. Among the four neurotrophins, BDNF was equal in potency to NT-4/5 at concentrations from 1–50 ng/ml ($P<0.001$ as compared to the control; FIG. 2). At 0.1 ng/ml, NT-4/5 was more potent than BDNF ($P<0.01$). NT-3 also displayed a significant survival-promoting effect ($P<0.05$ at 0.1 ng/ml; $P<0.001$ at higher doses), although this effect was less potent than NT-4/5 or BDNF at all doses (0.1–50 ng/ml) ($P<0.001$). In contrast, NGF showed no detectable effects in SGN cultures at all doses examined (FIG. 2).

To test whether NT-4/5, BDNF and NT-3 have synergistic effects, NT-4/5 was added together with BDNF or NT-3 into the culture; no additive effects were observed at saturated concentrations (FIG. 2).

To determine if SGNs respond to other growth factors, epidermal growth factor (EGF), basic fibroblast growth factor (βFGF), transforming growth factor-β1 (TGF-β1), TGF-β2, TGF-β3, or TGF-β5 was added to the cultures. No survival-promoting effects were seen, indicating selective responses of SGNs to NT-4/5, BDNF and NT-3.

Example II

SGNs Make TrkB Protein, the High-affinity Binding Receptor for BDNF and NT-4/5

To determine whether SGNs make trkB protein, the high-affinity binding receptor for BDNF and NT-4/5, trkB immunohistochemistry was performed on cross sections of P5 spiral ganglion with a polyclonal antiserum against trkB extracellular domain. Dual-immunohistochemistry was performed on cross sections of the spiral ganglion with trkB, trkA, or P75 and neurofilament protein antibodies. Texas red microscopy was used to show the staining pattern of antibodies against trkB, trkA and P75, respectively. Fluorescent microscopy was used to show the immunostainings of neurofilament antibody (N52) in the same sections as for Texas red microscopy. The SGN tissue was immersed in 4% paraformaldehyde (0.1M phosphate buffer, pH7.4) for 1 hour. After the preparations were cryoprotected with a 30% sucrose solution, cross sections were cut on a cryostat. The sections were first blocked with a 10% normal goat serum in 1% Triton X-100 in phosphate buffered saline ("PBS") for 20 minutes and then incubated with a mixture of a monoclonal antibody (N52) against neurofilament 200 kD (Boehringer, 5 ug/ml) and a rabbit antibody against extracellular trkB (anti-trkB$_{23-36}$; 2 ug/ml; Yan et al., 1994; Gao et al., 1995), a trkA antiserum, or a P75 antiserum in PBS containing 3% normal goat serum and 1% Triton X-100 overnight at 4° C. FITC-conjugated goat anti-mouse and Texas red-conjugated goat anti-rabbit secondary antibodies (1:70–100; Cappel) were then used to reveal the double labeling pattern in the sections. For neurofilament immunohistochemistry on cochlear wholemounts, the preparations were incubated with primary antibody for 2 days at 4° C. and then Texas red-conjugated goat anti-mouse antiserum (1:100; Cappel) was used to reveal the staining pattern. For neurofilament immunocytochemistry, SGN cultures were fixed in 4% paraformaldehyde (in 0.1M phosphate buffer, pH 7.4) for 30 minutes, washed in PBS (pH 7.4), and the immunostainings were performed with a biotinylated sheep anti-mouse secondary antibody and a streptavidin-horseradish peroxidase conjugate (1:200: Amersham Life Science) as described in Gao et al. (1995b).

N52 intensely labeled both somata and processes of SGNs in the spiral ganglions. SGN somata and processes were heavily labeled by trkB and P75 antibodies. In contrast, trkA antiserum (1:10,000; Clary et al., 1994) failed to detect the presence of trkA protein in these neurons. These results indicate that the effects of NT-4/5 and BDNF on these neurons are direct.

When the sections of spiral ganglion were double-labeled with a monoclonal antibody (N52) against neurofilament protein and trkB or trkA antiserum, the majority of the neurofilament-positive SGNs were also labeled by the trkB antiserum, but not the trkA antiserum, suggesting that most SGNs produce trkB, but not trkA proteins. It is of interest that SGNs were also immunoreactive to an antiserum against P75 (1:10,000; Weskamp and Reichardt, 1991), the low-affinity receptor for all neurotrophins. It appeared that all SGNs made the P75 protein. In addition, both trkB and P75 immunostainings extended into the cochlear epithelium; however, the immunoreactivities were confined to the afferent nerve terminals of SGNs, being undetectable in the hair cells.

Example III

TrkB-IgG Fusion Protein Blocks the Survival-promoting Activity of NT-4/5

Figure 3:
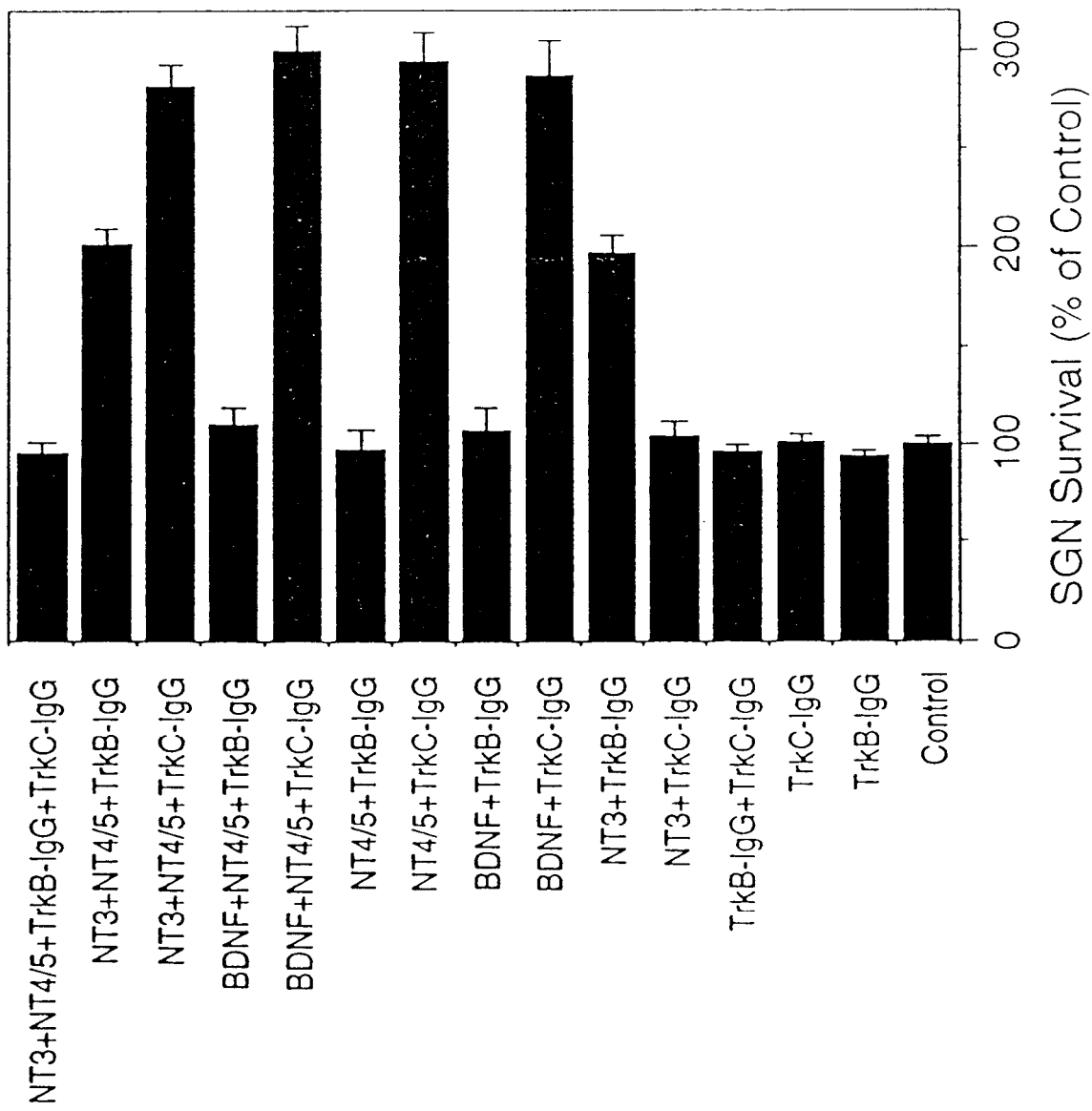
FIG. 3 is a histogram depicting trkB-IgG protein inhibition of the survival-promoting activity of NT-4/5 or BDNF. SGNs were prepared from P5 rats and kept for 2 days in serum-free medium containing 1 $\mu$g/ml trkB-IgG and/or trkC-IgG alone or in combination with 10 ng/ml neurotrophins. Quantitation of viable SGNs was done in the same way as in FIG. 1. The error bars indicate SEM.

To provide further evidence that NT-4/5 acts specifically on the SGNs, trkB-IgG fusion protein, a specific antagonist for NT-4/5 and BDNF (Shelton et al., 1995), was added to the SGN cultures containing NT-4/5 or BDNF. As shown in FIG. 3, addition of the trkB-IgG fusion protein completely inhibited the survival-promoting effects of NT-4/5 and/or BDNF. As expected, the trkB-IgG fusion protein did not block the activity of NT-3. On the other hand, trkC-IgG fusion protein, a specific antagonist for NT-3 (Shelton et al., 1995), abolished the effects of NT-3, but failed to block the effects of NT-4/5 and/or BDNF (FIG. 3). The specific blocking effects of trkB-IgG or trkC-IgG on NT-4/5 and BDNF or NT-3, respectively, were also seen when more than one neurotrophin was present in the culture. In addition, trkB-IgG and/or trkC-IgG themselves did not show detectable effects on the survival of SGNs in normal cultures (FIG. 3). These experiments considered together confirmed the specificity of trkB-IgG and trkC-IgG and indicate that the survival-promoting effects of NT-4/5 on SGNs are specific and result from agonism of trkB or trkC.

Example IV

Figure 4:
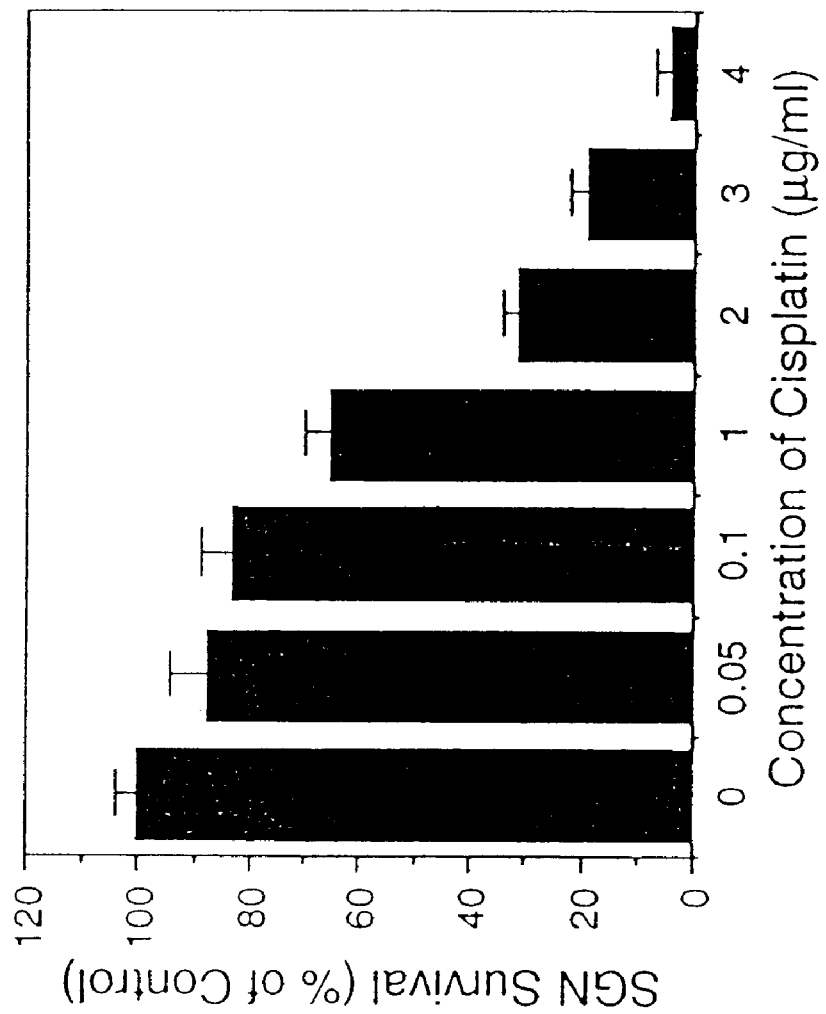
FIG. 4 is a histogram depicting cisplatin dose-dependent induction of neuronal cell death. SGNs were prepared from P5 rats, plated in serum-free medium containing different doses of cisplatin and assayed after 2 days in culture. Quantitation of viable SGNs was made in the same way as in FIG. 1. The error bars are SEM.

NT-4/5, BDNF and NT-3, but not NGF, Protect SGNs Against Cisplatin Neurotoxicity The ability of trkB or trkC agonists to protect neurons from ototoxicity was determined using SGNs in cell culture. When cisplatin was added to the SGN cultures, it induced a dose-dependent inhibition of SGN survival (FIG. 4). At a dose of 4 μg/ml or higher, virtually all SGNs died in the culture within 2 days. In contrast, cisplatin at a concentration of 4 µg/ml had no inhibitory effects on survival of postnatal neurons harvested from central nervous system such as cerebellar granule neurons or hippocampal neurons in vitro; the majority of cerebellar granule neurons and hippocampal neurons survived and elaborated neurites in the culture containing 4–6 µg/ml of cisplatin, suggesting that SGNs are selectively vulnerable to cisplatin.

Figure 5:
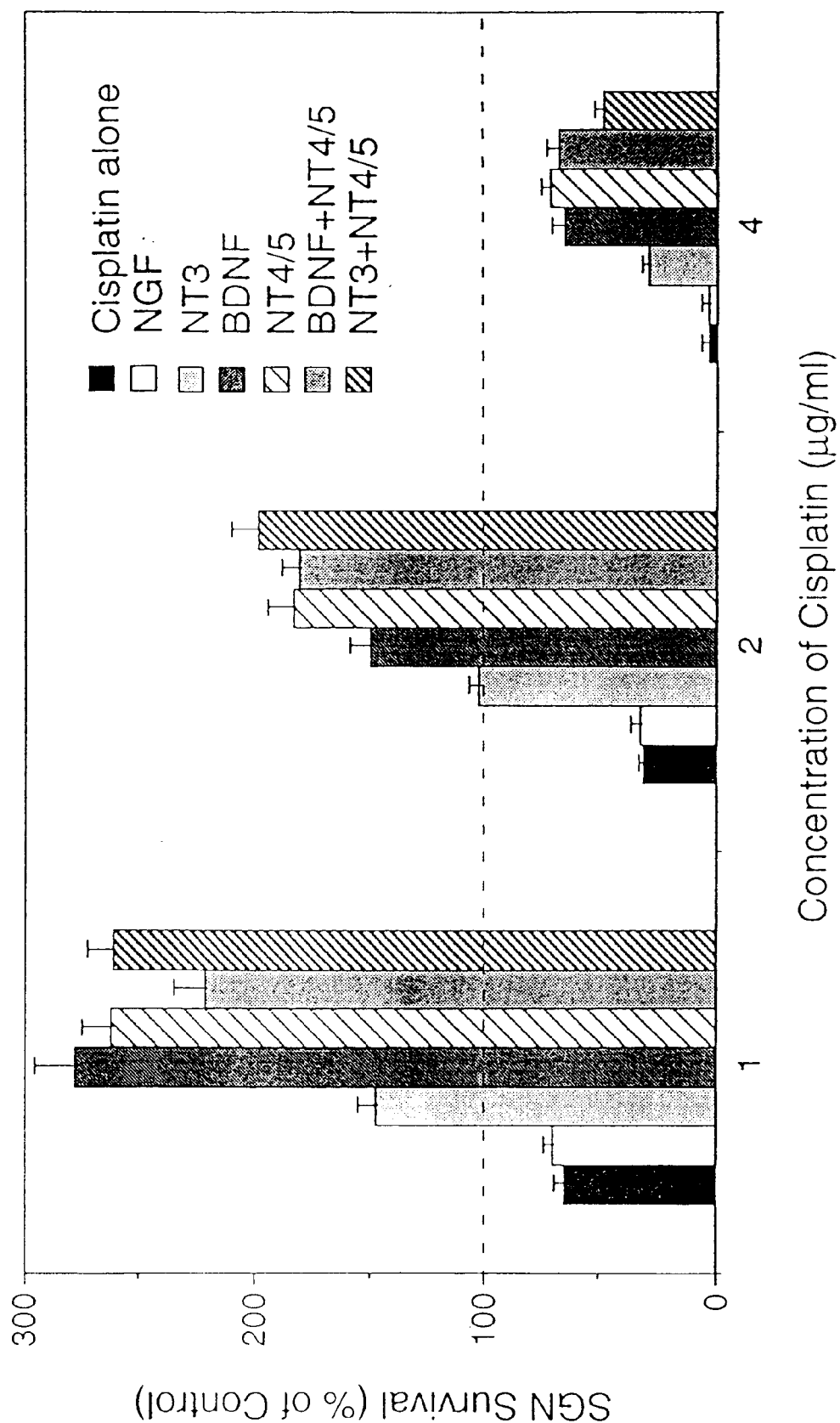
FIG. 5 is a histogram depicting NT-4/5, BDNF and NT-3 protection of SGNs against cisplatin neurotoxicity. SGNs were prepared from P5 rats and cultured for 2 days in serum-free medium containing 1 $\mu$g/ml, 2 $\mu$g/ml or 4 $\mu$g/ml of cisplatin alone or with 10 ng/ml of different neurotrophins. Quantitation of viable SGNs was done in the same way as in FIG. 1. The error bars stand for SEM. The dashed horizontal line indicates the survival level of normal cultures without cisplatin. Note that even in the cultures containing 4 $\mu$g/ml cisplatin, NT-4/5, BDNF and NT-3 showed very significant protecting effects on SGNs as compared to the culture containing cisplatin alone (P<0.001). While no difference was found between cultures containing NT-4/5 and cultures containing BDNF, the difference between cultures containing NT-3 and cultures containing NT-4/5 or BDNF was statistically very significant (P<0.001).

To determine if NT-4/5 could protect the SGNs from cisplatin neurotoxicity, 10 ng/ml NT-4/5 was added along with 3 different doses of cisplatin. At concentrations of 1 µg/ml or 2 µg/ml cisplatin, the percentage of surviving SGNs was higher than that in the control cultures lacking cisplatin (FIG. 5). This suggests that NT-4/5 promotes SGN survival and protects SGNs from cisplatin neurotoxicity. At 4 µg/ml of cisplatin, NT-4/5 still significantly protected SGNs from cell death ($P<0.001$), although the survival level was only 70% of control cultures in the absence of cisplatin (FIG. 5), Equivalent protective effects against cisplatin neurotoxicity were observed for 10 ng/ml BDNF. NT-3 at 10 ng/ml also displayed significant protective effects ($P<0.001$), but was less potent compared to NT-4/5 or BDNF ($P<0.001$). Combinations of NT-4/5 and BDNF or of NT-4/5 and NT-3 did not show additive effects as compared to that of NT-4/5 alone. Finally, NGF at 10 ng/ml did not show any protective effects (FIG. 5).

Example V

Cochlear Explant Cultures.

An organotype cochlear explant culture that utilizes a 3-D collagen matrix cultures and maintains its normal, in vivo architecture. Cochleae were dissected from postnatal day 3 (P3) Wistar rats. After spiral ligament and stria vascularis tissues were removed, the remaining cochlear tissue containing the spiral ganglion and organ of Corti was cut into 3 pieces according to the basal, middle and apical turns. The explants were then embedded in a three-dimensional ("3-D") collagen matrix of a droplet (20 µl) of freshly made collagen gel which was placed on the bottom of a 35 mm Nunc tissue culture dish, modified from what described previously (Gao et al., 1991) as follows. Rat tail collagen (type I, Collaborative Research) was mixed with 10× BME medium and 2% sodium carbonate in a ratio of 10:1:1 and placed on ice just before use. The collagen matrix containing the cochlear explants were incubated at 37° C. for 5–10 min until it gelled. The matrix was then cultured in defined serum-free medium using sufficient medium to cover the explants (2 ml of serum-free medium (BME plus serum-free supplement (Sigma 1–1884), 1% BSA, 2 mM glutamine, and 5 mg/ml glucose; containing no antibiotics). The culture medium was changed every other day thereafter.

Embedding the cochlear explants in the 3-D collagen was better for maintaining the normal architecture than floating the explants or placing the explants on a monolayer substrate, since the explant tissue could be kept unfolded and cell migration out of the tissue could be limited. Cochlear explants prepared according to the invention maintained normal architecture in the 3-D collagen gel cultures as observed by Nomarski micrographs of cochlear tissue dissected from P3 rats and grown for 2 days in vitro at low and high magnifications. Fluorescence microscopy showed the phalloidin staining of stereocillia bundles of hair cells in the cochlear explant cultured for 4 days. The cultured cochlear explants maintained normal laminar structures including the somata of the spiral ganglion, 1 row of inner hair cells, and 3 rows of outer hair cells in the organ of Corti. The SGNs and hair cells in the explants grew well and maintained their normal connectivity, such as the afferent innervation of hair cells by SGNs and stereocillia bundles of hair cells, as revealed by double histochemical labeling with a monoclonal antibody against neurofilament protein and a phalloidin-FITC conjugate. The SGNs and hair cells remained in their normal locations. No supernumerary rows of hair cells or gross cell death of SGNs and hair cells occurred under this culture condition. With the neurofilament antibody staining, the peripheral axons of the SGNs which innervate the hair cells in the organ of Corti were seen to maintain consistently a radial projection pattern, as seen in vivo.

Example VI

Ototoxicity in Cochlear Explant Cultures

Organotypic cultures of postnatal cochlear explants provided herein, in which the afferent innervation of hair cells by primary auditory neurons are intact, were used to examine ototoxicity of three different classes of clinical drugs represented by salicylate, gentamicin, and cisplatin. To determine if ototoxins were able to induce degeneration of SGNs and hair cells in the cochlear explant cultures, ototoxic therapeutic drugs were added to the culture at different concentrations. Histochemical double-labeling of the cochlear explant cultures with a neurofilament antibody (Texas red-mediated) and phalloidin (FITC-conjugated) was used to compare control cultures (untreated) with cultures treated with sodium salicylate, gentamicin, or cisplatin. While the neurofilament antibody (Texas red-mediated) labeled the somata and peripheral axons of SGNs, the phalloidin-FITC conjugate stained the stereocillia bundles of hair cells. Three cultures per experimental paradigm were studied in each individual experiment. Three or more separate repetitions of the experiment were conducted to validate the ototoxic effect.

Sodium salicylate was found to specifically induce neuronal degeneration, but not hair cell loss, in the cochlear explant cultures. Inclusion of sodium salicylate, an analog of aspirin, at a concentration of 5 mM in the culture induced massive death of SGNs and degeneration of their peripheral axons. In contrast, all hair cells remained intact. The sodium salicylate induced SGN degeneration was dose dependent (FIG. 6A). As the density of the radial peripheral axons of SGNs appeared to be a reliable index of the number of surviving SGNs, the number of the peripheral axons of SGNs from a given length (100 µm) in the middle turn of the cochlea was counted for different experimental groups and plotted in FIG. 6A. Phalloidin-labeled hair cells were also counted in the same way (FIG. 6B). In the control culture, there were approximately 24 radial peripheral axons and about 53 hair cells within a 100 µm length of the middle turn of the cochlea. In the presence of sodium salicylate, the number of SGN peripheral axons decreased sharply (FIG. 6A), but the number of hair cells remained the same (FIG. 6B). Even at a high concentration (10 mM), no significant hair cell loss was observed (FIG. 6B).

Figure 7A:
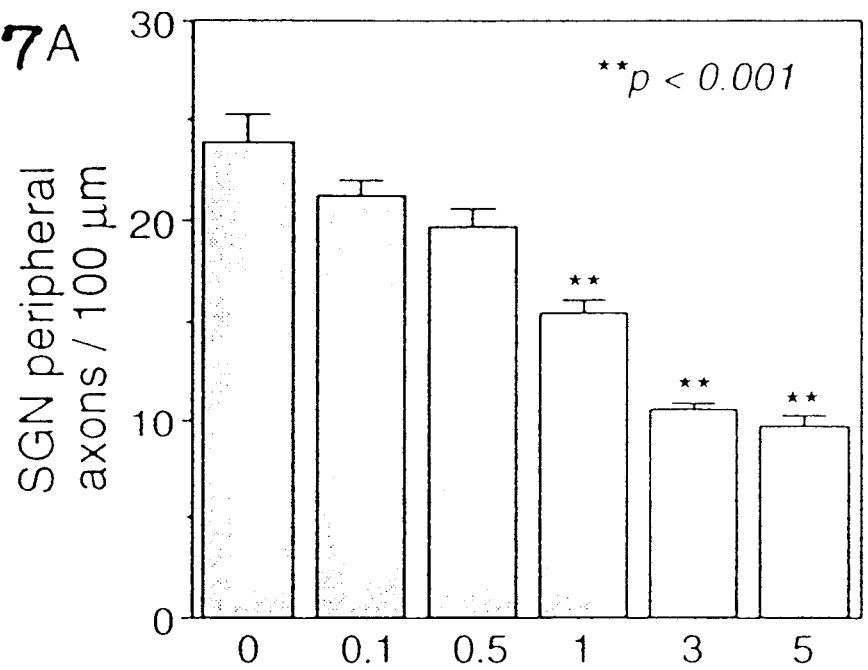
FIGS. 7A and 7B depict quantitation of toxic effects of gentamicin on SGNs (FIG. 7A) and hair cells (FIG. 7B). The same experimental procedures were performed as in FIGS. 6A and 6B. Note that gentamicin primarily destroyed hair cells at low doses, but started to induce damage to SGNs at doses higher than 1 mM. The error bars stand for SEM and double asterisks (**) indicate that as compared to the control cultures, p<0.001.
Figure 7B:
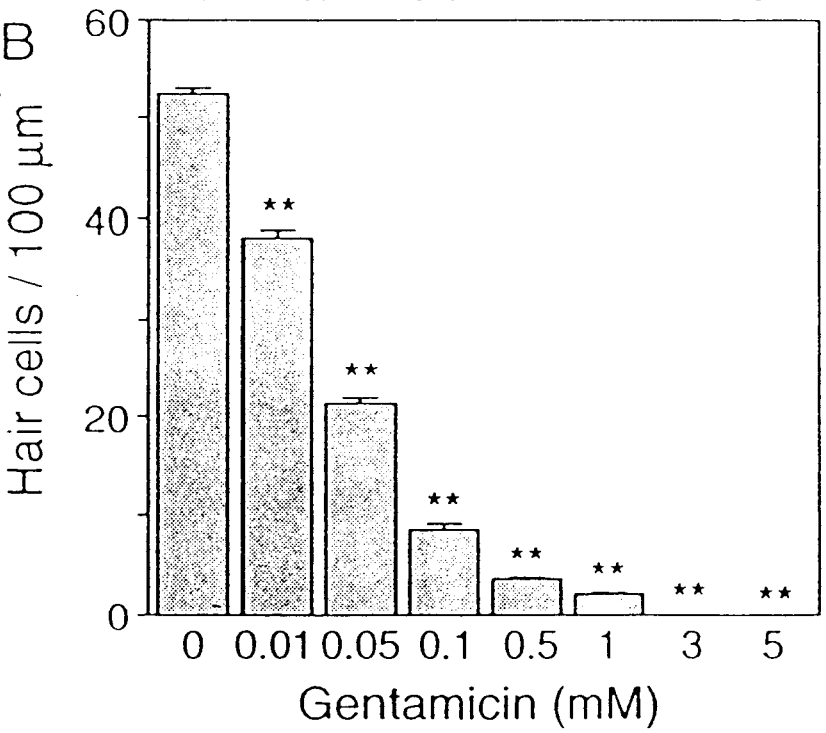

When the aminoglycoside gentamicin was added to the cochlear explant cultures, it preferentially destroyed hair cells at low doses. At concentrations ranging from 0.01 to 0.5 mM, a substantial number of hair cells in the cochlea were killed (FIG. 7B), but the SGNs were not significantly damaged ($P>0.05$; FIG. 7A). However, at higher concentrations (1–5 mM), gentamicin not only eliminated virtually all hair cells (FIG. 7B), it started to induce SGN degeneration as well (FIG. 7A). Debris of dead hair cells was easily seen in the region of organ of Corti. Nevertheless, even at a concentration of 5 mM, still approximately 40% of the SGNs remained intact (FIG. 7A). Similar results were observed when neomycin, another aminoglycoside, was added to the culture (data not shown), suggesting a common toxic mechanism amongst aminoglycosides.

Figure 8A:
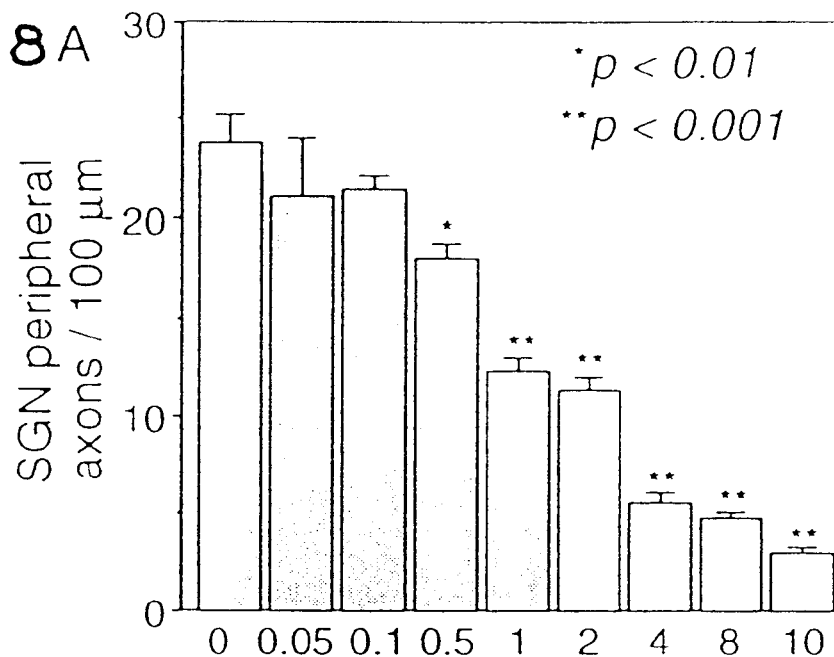
FIGS. 8A and 8B depict quantitation of toxic effects of cisplatin on SGNs (FIG. 8A) and hair cells (FIG. 8B). The same experimental procedures were performed as in FIGS. 6A and 6B. Note that cisplatin damaged both hair cells and SGNs and showed a more profound toxic effect on SGNs than on hair cells. The error bars are SEM. * and ** indicate that as compared to the control cultures, p<0.01 and p<0.001, respectively.
Figure 8B:
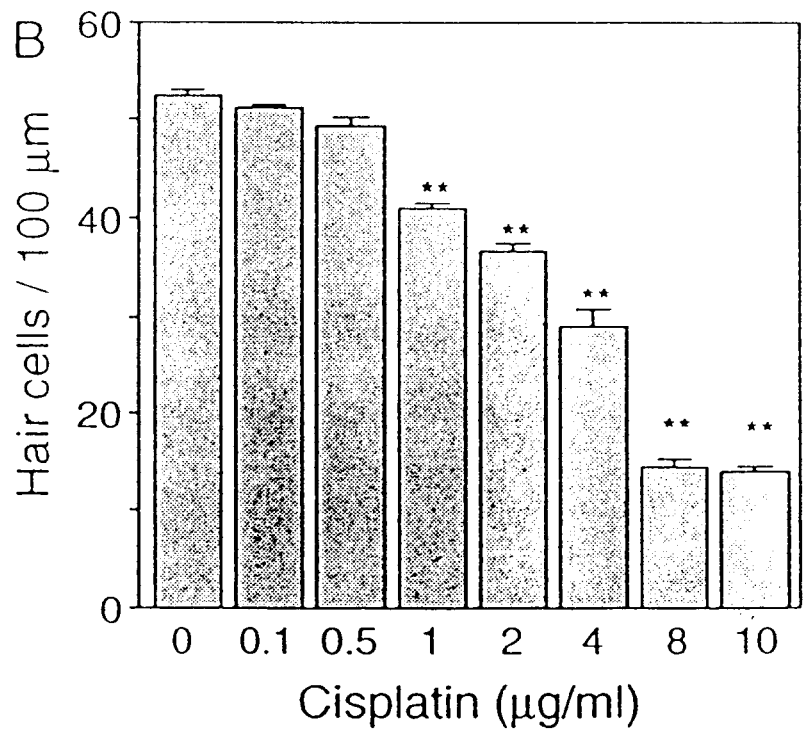

It has been reported that cisplatin induces hair cell loss in the organ of Corti (Fleischman et al., 1975; McAlpine and Johnstone, 1990). In the dissociated cell cultures reported herein, cisplatin induced SGN cell death, indicating a direct toxic effect on SGNs. Cisplatin ototoxicity was further studied by adding various concentrations of cisplatin to the cochlear explant cultures of the invention in which innervation of hair cells by SGNs were intact. Cisplatin damaged both SGNs and hair cells at a wide range of concentrations (1–10 µg/ml) (FIGS. 8A, 8B). However, it showed a more profound toxic effect on SGNs than on hair cells. At a concentration of 0.5 mg/ml, cisplatin induced a significant degeneration of SGNs and their peripheral axons (p<0.01, FIG. 5A). In contrast, hair cell loss was not statistically significant (p>0.05, FIG. 8B). When the cisplatin dose was raised to 1–2 µg/ml, between 20–30% of hair cells was destroyed while about 50% of SGNs degenerated; the damages to both SGNs and hair cells became significant (p<0.001; FIGS. 8A, 8B). At a concentration of 4 µg/ml, cisplatin destroyed most of the SGNs and about 55% hair cells still remained intact. At even higher concentrations (8–10 µg/ml), this drug destroyed a majority of hair cells as well (FIG. 8B).

Example VII

Protective Effects of Neurotrophins in Cochlear Explant Cultures

The protective effect of neurotrophins against ototoxicity was determined in the organotypic cultures of postnatal cochlear explants described in the Examples above. Sodium salicylate (Sigma), gentamicin sulfate (Sigma) or cisplatin (Bristol-Myers Squibb) was added at various concentrations to 2-day cultures of cochlear explants. A human recombinant neurotrophin (Genentech, Inc.) or other growth factors, alone or in combination, was added to the culture at the same time the ototoxin was added. Three cultures per experimental paradigm were studied in each individual experiment. Three or more separate repetitions of the experiment were conducted to demonstrate the neuroprotective effect.

Two days after treatment with ototoxins or co-treatment with ototoxins and neurotrophins (or other growth factors), the cochlear explant cultures were fixed in 4% paraformaldehyde in 0.1 M phosphate buffer (pH 7.4) for 30 min, washed in PBS, and subjected to double histochemical staining of the cochlear explant cultures. After incubation with the monoclonal antibody N52 against neurofilament protein (200 kd) in 1% Triton X100 containing 3% normal goat serum ("NGS") for 2 days at 4° C., the explants were incubated with a Texas red-conjugated goat anti-mouse secondary antibody (1:70; Cappel) at room temperature for 40 min. The preparations were then stained with FITC-conjugated phalloidin (0.5 µg/ml; Sigma) for 45 min, washed in PBS and mounted in Fluoromount-G (Southern Biotechnology Associates, Birmingham, Ala.) which contains an anti-fading agent.

Quantitative analysis of the numbers of peripheral axons of SGNs and hair cells in the cochlear explants were performed. The N52 and phalloidin double-labeled cochlear explants were examined under a Zeiss Axiophot epifluorescent microscope. As the density of radial peripheral axons of SGNs reflects the number of surviving SGNs, the number of these axons was counted using a grid ocular reticule covering a distance of 100 µm in the middle turns only. The surviving hair cells were counted in a similar manner. The density of the radial axons in the apical turn was a little higher than that in the basal turn and hair cells in the apical turn were somewhat more resistant to ototoxins. For each culture, SGN peripheral axons and hair cells were counted from 3–4 randomly selected fields in the middle turn of each culture. Data were collected from 6 or more cultures for each of the experimental groups. Two-tailed, unpaired t-test was used for statistical analysis.

Figure 9A:
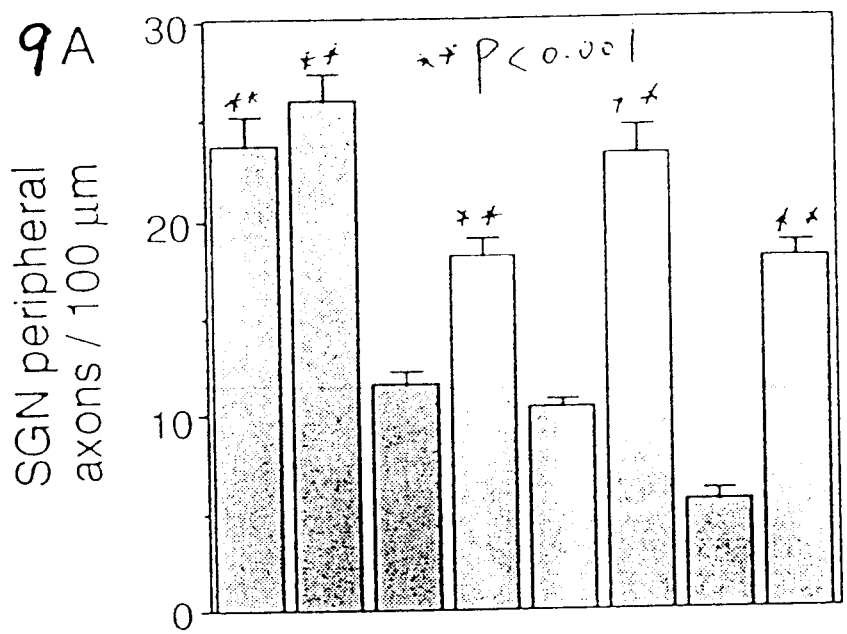
FIGS. 9A and 9B depict quantitation of protective effects of NT-4/5 on SGNs (FIG. 9A) and hair cells (FIG. 9B). Cochlear explants were prepared from P3 rats, embedded and cultured in a 3-D collage gel. Sodium salicylate ("Sal"; 5 mM), gentamicin ("Gent"; 3 mM) or cisplatin ("Cis"; 4 $\mu$g/ml) was added either alone or in combination with NT-4/5 (20 ng/ml) to 2-day cultures and the cultures were kept for 2 more days. The same experimental procedures were performed as in FIGS. 6A and 6B. The error bars are SEM and ** indicate that as compared to the cultures containing an ototoxin alone, p<0.001. "Con" indicates control culture.
Figure 9B:
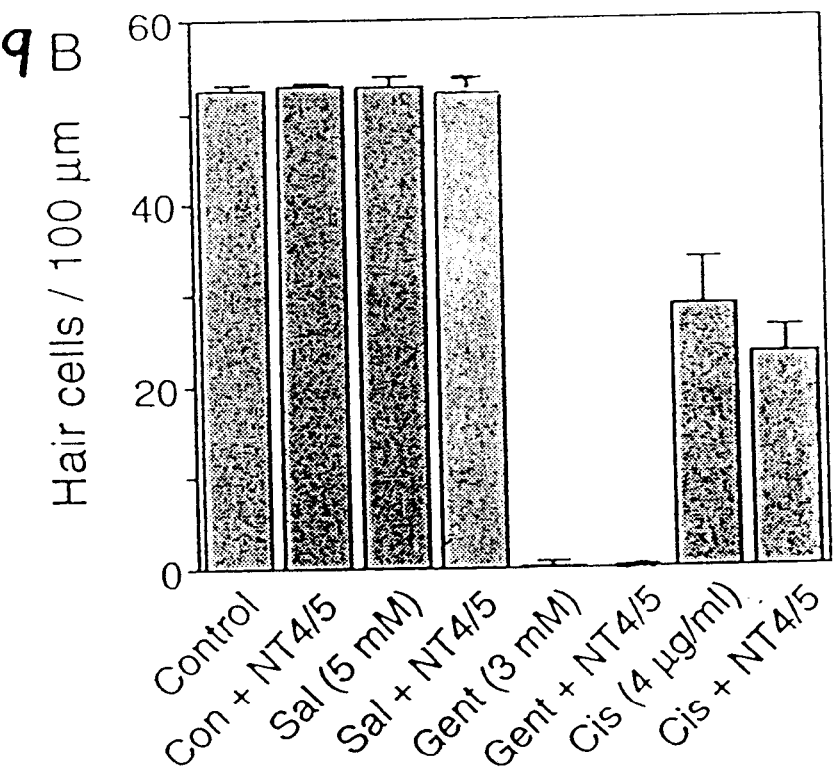
Figure 10:
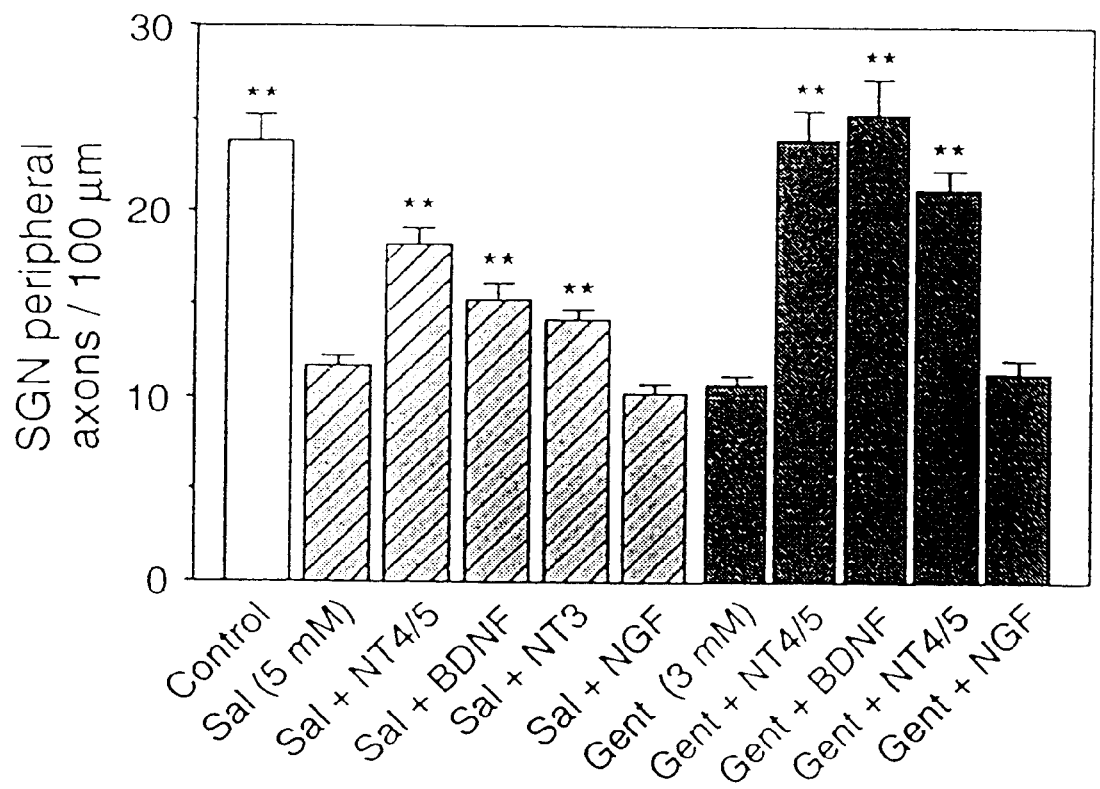
FIG. 10 depicts quantitation of neuroprotection of different neurotrophins against sodium salicylate (Sal) and gentamicin (Gent). Cochlear explants were prepared from P3 rats, embedded and cultured in a 3-D collagen gel. Sodium salicylate (5 mM) or gentamicin (3 mM) was added either alone or in combination with one of the neurotrophins (20 ng/ml) to 2-day cultures and the cultures were kept for 2 more days. The same experimental procedures were performed as in FIGS. 6A and 6B. Note that NT-4/5, BDNF and NT-3, but not NGF showed significant neuroprotection. The error bars are SEM and ** indicate that as compared to the cultures containing an ototoxin alone, p<0.001.

The three types of drugs induced differential damage to auditory neurons and hair cells in the cochlea as shown in the above Examples. Sodium salicylate (3–10 mM) specifically induced degeneration of auditory neurons, but not hair cell loss. Gentamicin (0.01–0.5 mM) preferentially caused hair cell death, though loss of auditory neurons was also seen at higher concentrations (1–5 mM). In contrast, addition of cisplatin to the culture resulted in degeneration of both auditory neurons and hair cells at a wide range of doses tested (1–10 µg/ml), with more profound damage to auditory neurons than to hair cells. When neurotrophins and other growth factors were added to the culture together with the ototoxins, neuronal degeneration was prevented by neurotrophin-4/5 ("NT-4/5"), brain-derived neurotrophic factor ("BDNF") and neurotrophin-3 ("NT-3"), but not by NGF or other growth factors. In contrast, the hair cell loss caused by cisplatin or gentamicin was not prevented by the presence of neurotrophins. While other growth factors, including epidermal growth factor (EGF) ( Collaborative Research), basic fibroblast growth factor (βFGF) (Gibco), FGF-5 (R & D Systems), FGF-7 (R&D Systems), insulin-like growth factor-1 (IGF-1) (Genentech), platelet-derived growth factor (PDGF) (Gibco), transforming growth factor-α (TGF-α) (R & D Systems), TGF-β1 (Genentech), TGF-β2, TGF-β3, TGF-β5 (R & D Systems) or retinoic acid (Sigma), did not show detectable protective effects on either SGNs or hair cells (data not shown), specific neurotrophins—those that bind trkB or trkC—displayed significant protection for SGNs against the three ototoxins. When NT-4/5 was added at a concentration of 20 ng/ml together with an ototoxin, degeneration of SGNs and their peripheral axons was prevented as determined by histochemical double labeling (a neurofilament antibody (Texas red-mediated) and phalloidin (FITC-conjugated)) of cochlear explant cultures of a culture co-treated with sodium salicylate (5 mM) and NT-4/5 (20 ng/ml), a culture co-treated with gentamicin (3 mM) and NT-4/5 (20 ng/ml), and a culture co-treated with cisplatin (4 µg/ml) and NT-4/5 (20 ng/ml). As compared to the ototoxicity observed in the Examples above, NT-4/5 protected SGNs, but not hair cells, from all of the three ototoxins. However, hair cell loss caused by gentamicin or cisplatin was not stopped by the presence of NT-4/5. Quantitation of protective effects of NT-4/5 on SGNs and hair cells against the three ototoxins is shown in FIGS. 9A and 9B. The presence of NT-4/5 in control cultures did not enhance the number of SGNs or hair cells (p>0.05), though it significantly protected SGNs from the three ototoxins (p<0.001; FIGS. 9A and 9B). The protective effects on SGNs but not on hair cells were also observed with BDNF and NT-3 (FIG. 10). In contrast, NGF did not show any detectable protection (FIG. 10). The finding that the three ototoxins tested induced differential damage to auditory neurons and hair cells in the cochlea, suggests (a hypothesis forwarded solely for discussion and not necessarily as the underlying fact of the present invention) that salicylates, aminoglycosides and chemotherapeutic agents act through different mechanisms. Nonetheless, as show herein, all are treatable with compositions and methods of the invention.

Neurotrophins are members of the NGF family of proteins. They have been widely shown to regulate the differentiation and survival of developing neurons (Korsching, 1993, Gao et al., 1995a) as well as to aid in the repairing or recovery of adult CNS neurons from injury and toxins (Hefti, 1986; Knusel et al., 1992; Yan et al., 1992; Gao et al., 1995b). They exert their biological functions through activation of high-affinity binding receptors, the trks with high characteristic specificity (Barbacid, 1993; Snider, 1994). Previous studies indicate that the SGNs express specific trk genes (Ylikoski et al., 1993; Schecterson and Bothwell, 1994). As reported herein, SGNs express specific trk proteins (see also Vazquez et al., 1994). Hair cells express certain neurotrophin genes (Pirvola et al., 1992; Schecterson and Bothwell, 1994; Wheeler et al., 1994). In dissociated cell culture systems, as shown herein, specific neurotrophins promote survival of SGNs (Vazquez et al., 1994; Lefebvre et al., 1994). As demonstrated for the first time herein, neurotrophins protect SGNs from cisplatin ototoxicity. Similarly, as demonstrated for the first time herein, these neurotrophins also protect vestibular ganglion neurons from gentamicin in vitro. The results presented with organotypic cochlear explants are consistent with the dissociated neuronal culture findings. As the organotypic culture keeps the afferent innervation of hair cells by SGNs intact, it better represents the in vivo system and , consequently, allows exploration of the mechanism of actions of ototoxins and, most importantly, provides a system to discover and test candidate protective agents. While NT-4/5, BDNF and NT-3 protect SGNs against all three ototoxins, they are particularly preferred to prevent salicylate-induced hearing disorders.

Salicylates, such as aspirin, are the most commonly used therapeutic drugs for their anti-inflammatory, analgesic, anti-pyretic and anti-thrombotic effects. Unfortunately, they have ototoxic side effects. They often lead to tinnitus ("ringing in the ears") and temporary hearing loss (Myers and Bernstein, 1965). Although clinical and animal studies suggest that the site of action of this drug is in the cochlea (Myers and Bernstein, 1965; McCabe and Dey, 1965), the mechanism for the ototoxicity of salicylates is still unclear. Electrophysiological recordings in animals indicate salicylates result in an increase in hearing suprathreshold, which suggests damage to hair cells (Boettcher et al., 1989; Boettcher and Salvi, 1991). However, postmortem examination of a patient who received large doses of aspirin showed normal hair cell numbers, but a significant loss of SGNs (De Moura and Hayden, 1968). The results presented in this specification clearly demonstrate for the first time the selective toxic effects of salicylates on auditory neurons, but not on hair cells. Interestingly, the dosage (3 mM) of salicylate which starts to induce significant damage to SGNs in the present study is comparable to the peak serum and perilymph levels that result in hearing losses (Myers and Bernstein, 1965; Woodford et al., 1978; Boettcher et al., 1990). The finding that sodium salicylate at both low and high concentrations exclusively induces degeneration of SGNs and their axons, but not hair cells suggests a possibility that the initial hearing disorder caused by salicylates may result from neuronal dysfunction, perhaps axonal degeneration in the eighth nerve or abnormality in SGNs (Wittmaack, 1903). Once the drug is stopped, the damaged axons may regenerate successfully and restore the normal auditory function. Such initial axonal degeneration is therefore reversible. However, if the drug is used at high doses for a prolonged time, the neuronal impairment will become more severe and SGN death occurs. As a consequence, the hearing impairment may become persistent and irreversible, as reported clinically (Jarvis, 1966).

It is interesting to note that while many previous studies suggested that the primary action site of cisplatin is the hair cell (Fleischman et al., 1975; McAlpine and Johnstone, 1990; Pryor, 1994), the experiments presented in this specification indicates for the first time that cisplatin damages both hair cells and SGNs, and that at low concentrations it shows a more profound toxic effects on SGNs than hair cells. Neurotoxicity of cisplatin was also noted on proprioceptive sensory neurons in vivo (Thompson et al., 1984) and in vitro (Windebank et al., 1994; Konings et al., 1994), resulting in peripheral sensory neuropathy (Siegal and Haim, 1990; Gao et al., 1995b). The action of cisplatin on cancer cells is to interfere with DNA synthesis as it induces inter- and intra-strand cross linking of DNA molecules. In a rat model of cisplatin-induced peripheral neuropathy, cisplatin also induces cytoplasmic patching of neurofilament protein (Gao et al., 1995b), one of the components of the cytoskeletal complex. Although not meant to be limiting to the invention, it is suggested that the susceptibility of SGNs and hair cells to cisplatin may be attributable to the fact that they are highly enriched in cytoskeletal components, such as neurofilament and actin. In support of this notion, cisplatin has been reported to affect the intermediate and microfilament cytoskeletal network in cultured squamous carcinoma cells (Kopf-Maier and Muhlhausen, 1992). The results of the cochlear explants in the above Examples support the notion that cisplatin directly damages ganglion neurons, as observed in the dissociated cell cultures in the Examples herein.

Although the present results indicate that particular neurotrophins have strong protective effects on SGNs, they did not protect hair cells from the ototoxic drugs. In addition, none of the presently known growth factors including EGF, βFGF, FGF-5, FGF-7, IGF-1, PDGF, TGF-α, TGF-β1, TGF-β2, TGF-β3, TGF-β5 or retinoic acid shows protective effects on SGNs or hair cells. These results suggest that most presently known growth factors are not critical for protection or maintenance of hair cells. If hair cell loss due to ototoxicity is significant, hearing recovery could be improved by new hair cell growth or regeneration. Recent studies have suggested possible candidates (Forge et al., 1993; Cotanche and Lee, 1994; Tsue et al., 1994a; Cotanche and Lee, 1994; Kelley et al., 1995). For example, diffusible factors such as TGF-α and EGF (Lambert, 1994; Yamashita and Oesterle, 1995) or components derived from antibiotic treated inner ear tissue (Tsue et al., 1994b) stimulate proliferation of supporting cells. Retinoic acid alone or in combination with TGF-α facilitates hair cell regeneration in vitro (Lefebvre et al., 1993, 1995). As taught herein, neurotrophins will provide for prevention of neuronal cell death after injury or insult by ototoxins. Furthermore, although cochlear implants have been performed clinically with patients benefiting from the cochlear implants, a gradual SGN loss still occurs (Leake et al., 1992). Neurotrophins will prove to be important in keeping ganglion neurons alive in cochlear implants. A combination of specific neurotrophins and hair cell growth factors or cochlear implants will prove preferably competent for recovery or repairing of hearing loss caused by ototoxins or injury.

REFERENCES

Anniko M, Sobin A (1986) Cisplatin: Evaluation of its ototoxic potential. Am J Otolaryngol 7:276–293.

Apfel S C, Lipton R B, Arezzo J C, Kessler J A (1991) Nerve growth factor prevents toxic neuropathy in mice. Ann. Neurol. 29:87–89.

Ard, M. D., Morest, D. K., and Hauger, S. H. (1985). Trophic interactions between the cochleovestibular ganglion of the chick embryo and its synaptic targets in culture. Neurosci. 16:151–170.

Au S, Weiner N D, Schacht J (1987) Aminoglycoside antibiotics preferentially increase permeability in phosphoinositide-containing membranes: a study with carboxyflurorescein in liposomes. Biochem Biophys Acta 902:80–86.

Baired D H, Hatten M E, Mason C A (1992) Cerebellar target neurons provide a stop signal for affrent neurite extension in vitro. J. Neurosic. 12:619–634.

Barbacid, M. (1993). The trk family of neurotrophin receptors: molecular characterization and oncogenic activation in hauman tumors. In *Molecular Genetics of Nervous System Tumors.* Levin, A. G. and Schmidek, H. H., eds. (New York: Wiley-Liss), pp123–136.

Barde Y A, Edgar D, Thoenen H (1982) Purification of a new neurotrophic factor from mammalian brain. EMBO J. 1:549–553.

Bareggi, R., Grill, V., Narducci, P., Zweyer, M., Tesei, L, and Russolo, M. (1990).Genetamicin ototoxicity: Histological and ulstructural alterations after transtympanic administration. *Pharmacol. Res.* 22:635–644.

Barker, P. A., and Shooter, E. M. (1994). Disruption of NGF binding to the low affinity neurotrophin receptor $p75^{LNTR}$ reduces NGF binding to trkA on PC12 cells. *Neuron* 13:203–215.

Berggren, D, Anniko, M, Thornell, L. -E., Ramaekers, F. C. S., and Virtanem, I. (1990). Intermediate filament proteins in the embryonic inner ear of mice under normal conditions and after exposure to ototoxic drugs. *Acta Otolaryngol.* (*Stockh*) 109:57–65.

Berkemeier L R, Winslow J W, Kaplan D R, Nikolics K, Goeddel D V, Rosenthal A (1991) Neurotrophin-5: A novel neurotrophic factor that activates trk and trkB. Neuron 7:857–866.

Boettcher F A, Bancroft B R, Salvi R J, Henderson D (1989) Effects of sodium salicylate on evoked-response measures of hearing. Hear Res 42: 129–142.

Boettcher F A, Bancroft B R, Salvi R J, Henderson D (1990) Concentration of salicylate in serum and perilymph of the chinchillla. Arch Otolaryngol Head Neck Surg 116:681–684.

Boettcher F A, Salvi R J (1991) Salicylate ototoxicity: review and synthesis. Am. J Otolaryngol 12: 33–47.

Carenza, L., Villani, C., Framarino dei Malatesta, M. L., Prosperi Porta, R., Millefiorine, M., Antonini, G., Bolasco, P., Bandiera, G., and Marzetti, L. (1986). Peripheral neuropathy and ototoxicity of dichlorodiamineplatinum: instrumental evaluation. *Gynecol. Oncol.* 25:244–249.

Chao, M. V., Bothwell, M. A., Ross, A. H., Koprowski, H., Lanahan, A. A., Buck, C. R., and Sehgal, A. (1986). Gene transfer and molecular cloning of the human NGF receptor. *Science* 232:518–521.

Chao, M. V. (1992). Growth factor signalling: where is the specificity? *Cell* 68:995–997.

Clary, D. O., and Reichardt, L. F. (1994). An alternatively spliced form of the nerve growth factor receptor trkA confers an enhanced response to neurotrophin 3. *Proc. Natl. Acad. Sci. USA* 91:11133–11137.

Clary, D. O., Weskamp, G., Austin, L. R., and Reichardt, L. F. (1994). trkA cross-linking mimics neuronal responses to nerve growth factor. *Mol. Biol. Cell* 5:549–563.

Cohen A, Bray G M, Aguayo A J (1994) Neurotrophin-4/5 (NT-4/5) increases adult rat retinal ganglion cell survival and neurite outgrowth in vitro. J. Neurobiol. 25:953–959.

Cordon-Cardo, C., Tapley, P., Jing, S., Nanduri, V., O'Rourke, E., Lamballe, F., Kovary, K., Klein, R., Jones, K. R., Reichhardt, L. F. and Barbacid, M. (1991), Cell, 66, 173–183

Corwin J T, Warchol M E (1991) Auditory hair cells: structure, function, development, and degeneration. Ann Rev Neurosci 14: 301–333.

Cotanche D A, Lee K H (1994) Regeneration of hair cells in the vestibulocochlear system of birds and mammals. Curr Opinion Neurobiol 4: 509–514.

Davies, A. M., Lee, K. F., and Jaenisch, R. (1993). p75-deficient trigeminal sensory neurons have an altered response to NGF but not to other neurotrophins. *Neuron* 11:565–574.

Davies A M, Horton A, Burton L E, Schmelzer C, Vandlen R, Rosenthal A (1993b) Neurotrophin-4/5 is a mammalian-specific survival factor for distinct populations of sensory neurons. J. Neurosci. 13:4961–4967.

Davies, A. M., Thoenen, H., and Barde, Y. -A. (1986). Different factors from the central nervous system and peripheral regulate the survival of sensory neurons. *Nature* 319:497–502.

De Moura L F P, Hayden R C (1968) Salicylate ototoxicity. Arch Otolaryng 87:60–64.

Dublin W B (1976) Fundamentals of sensorineural auditory pathology. Springfield, Ill.: C. C. Thomas.

Duckert, L. G., and Rubel, E. W. (1994). Morphological correlates of the functional recovery in the chicken inner ear after gentamicin treatment. *J. Comp. Neurol.* 331:75–96.

Ernfors P, Ibanez C F, Ebendal T, Olson L, Persson H (1990) Molecular cloning and neurotrophic activities of a protein with structural similarities to nerve growth factor: developmental and topographic expression in the brain. Proc. Natl. Acad. Sci. USA 87:5454–5458.

Emfors, P., Lee, K. -F., and Jaenisch, R. (1994). Mice lacking brain-derived neurotrophic factor develop with sensory deficits. *Nature* 368:147–150.

Ernfors P, Loring J, Jaenisch R, Van De Water T R (1995) Function of neurotrophins in the auditory and vestibular systems: Analysis of BDNF and NT-3 gene knockout mice. Assoc. Res Otolaryngol Abstr p190.

Escandon E, Soppet D, Rosenthal A, Mendoza-Ramierz J-L, Szonyi E, Burton L E, Henderson C E, Parada L F, Nikolics K (1994) Regulation of neurotrophin receptor expression during embryonic and postnatal development. J. Neurosci. 14:2954–2068.

Falbe-Hansen J (1941) Clinical and experimental histological studies on effects of salicylate and quinine on the ear. Acta Otolaryng suppl 44: 1–216.

Fariñas, I., Jones, K. R., Backus, C., Wang, X. -Y., and Reichardt, L. F. (1994). Severe sensory and sympathetic deficits in mice lacking neurotrophins-3. *Nature* 369:658–661.

Fischer W, Sirevaag A, Wiegand S J, Lindsay R M, Bj örklund A (1994) Reversal of spatial memory impairments in aged rats by nerve growth factor and neurotrophins 3 and 4/5 but not by brain-derived neurotrophic factor. Proc. Natl. Acad. Sci. USA 91:8607–8611.

Fleischman, R. W., Stadnicki, S. W., Ethier, M. F., and Schaeppi, U. (1975). Ototoxicity of cis-dichlorodiammine platinum (II) in the guinea pig. *Toxicol Appl. Pharmacol.* 33:320–332.

Forge A, Li L, Corwin J T, Nevill G (1993) Ultrastructural evidence for hair cell regeneration in the mammalian inner ear. Science 259:1616–1619.

Fritzsch, B., Smyene, R., Fagan, A., Selos-Santiago, I. (1995). Mice homologous for a non-functional trk-B receptor lack selectively in the innervation of semicircular canals. Assoc. Res. Otolaryngol. Abstr. p190.

Furley A, Morton S B, Malano D, Karagogeos, Dodd J, Jessell T M (1990) The axonal glycoprotein TAG-1 is an immunoglobin superfamily member with neurite outgrowth-promoting activity. Cell 61:157–170.

Gao W-Q, Heitz N, Hatten M E (1991) Cerebellar granule cell neurogenesis is regulated by cell-cell interactions in vitro. Neuron 6:705–715.

Gao W-Q, Dybdal N, Shinsky N, Muurane A, Schmelzer C, Siegel M, Keller G, Hefti F, Phillips H S, Winslow J W (1995b) Neurotrophin-3 reverses experimetal cisplatin-induced peripheral sensory neuropathy. Ann Neurol (1995) 38:30–37.

Gao, W. -Q., Zheng, J. L., and Karihaloo, M. (1995). Neurotrophin-4/5 (NT-4/5) and brain-derived neurotrophic factor (BDNF) act at later stages of cerebellar granule cell differentiation. *J. Neurosci.* 15:2656–2667.

Garner A S, Large T H (1994) Isoforms of the avian trkC receptor: A novel kinase insertion dissociates transformation and process outgrowth from survival. Neuron 13:457–472.

Gotz, R., Koster, R., Winkler, C., Raulf, F., Lottspelch, F., Scharti, M., and Thoenen, H. (1994). Neurotrophin-6 is a new member of the nerve growth factor family. *Nature* 372:266–269.

Grotz et al., Eur. J. Biochem. 204:745–749 (1992)

Guild S, Cowe S, Bunch C, Polvogt (1931) Correlations of differences in sensory of innervation of the organ of Corti with differences in the acuity of hearing, including evidences as to the location in the human cochlea of receptors for certain tones. Acta Otolaryngol. (Stockh) 15:269–308.

Hefti F (1986) Nerve growth factor (NGF) promotes survival of septal cholinergic neurons after fimbrial transections. J Neurosci 6:2155–2162.

Hinojosa, R., and Lerner, S. A. (1987). Cochlear neural degeration without hair cell loss in two patients with aminoglycoside ototoxicity. *J. Infect. Dis.* 156: 449–455

Hohn A, Leibrock J, Bailey K, Barde Y A (1990) Identification and characterization of a novel member of the nerve growth factor/brain-derived neurotrophic factor family. Nature 344:339–341.

Hood J L, Berlin C I, Ed., *Contemporary applications of neurobiology in human hearing assessment* (Raven Press, New York, 1986).

Hulme, E. C. and Birdsall, M. J. M., Strategy and Tactics in Receptor Binding Studies, p63–212 in Receptor-Ligand Interactions, Ed. E. C. Hulme Hyman C, Hofer M, Barde Y A, Juhasz M, Yancopoulos G D, Squinto S P, Lindsay R M (1991) BDNF is a neurotrophic factor for dopaminergic neurons of the substantia nigra. Nature 350:230–233.

Hynes M A, Poulsen K, Armanini M, Berkemeier L, Phillips H, Rosenthal A (1994) Neurotrophin-4/5 is a survival factor for embryonic midbrain dopaminergic neurons in enriched cultures. J. Neurosci. Res. 37:144–154.

Ip N Y, Stitt T N, Tapley P, Klein R, Glass D J, Fandl J, Greene L A, Barbacid M, Yancopoulos G D (1993) Similarities and differences in the way neurotrophins interact with the trk receptors in neuronal and nonneuronal cells. Neuron 110:137–149.

Ip N Y, Ibáñez C F, Nye S H, McClain J, Jones P F, Gies D R, Belluscio L, LeBeau M M, Espinso III R, Squinto S P, Persson H, Yancopoulos G D (1992) Mammalian neurotrophin-4: Structure, chromosomal localization, tissue distribution, and receptor specificity. Proc. Nat. Acad. Sci. USA 89:3060–3064.

Jarvis J F (1966) A case of unilateral permanent deafness following acetyl salicylic acid. J Laryngol 80: 318–320.

Jones K R, Reichardt L F (1990) Molecular cloning of a human gene that is a member of the nerve growth factor family. Proc. Natl. Acad. Sci. USA 87:8060–8064.

Kaplan, D. R., Hempstead, B., Martin-Zanca, D., Chao, M., and Parada, L. F. (1991) Science 252, 554–558

Kaplan D R, Martin Z D, Parada L F (1991) Tyrosine phosphorylation and tyrosine kinase activity of the trk proto-oncogene product induced by NGF. Nature 350:158–160.

Kelley M W, Telreja D R, Corwin J T (1995) Replacement of hair cells after microbeam irradiation in cultured organs of Corti from embryonic and neonatal mice. J Neurosci 15:3013–3026.

Kelley M W, Xu X-M, Wagner M A, Warchol M E, Corwin J T (1993) The developing organ of Corti contains retinoic acid and forms supernumerary hair cells in response to exogenous retinoic acid in culture. Development 119:1041–1053.

Klein R, Jing S Q, Nanduri V, O'Rourke E, Barbacid M (1991a) The trk proto-oncogene encodes a receptor for nerve growth factor. Cell 65:189–197.

Klein R, Nanduri V, Jing S A, Lamballe F, Tapley P, Bryant S, Cordon-Cardo C, Jones K R, Reichardt L F, Barbacid M (1991b) The trkB tyrosine protein kinase is a receptor for brain-derived neurotrophic factor and neurotrophin-3. Cell 66:395–403.

Klein R, Martin-Zanca D, Barbacid M, Parada L F (1990) Expression of the tyrosine kinase receptor gene trkB is confined to the murine embryonic and adult nervous system. Development 109:845–850.

Klein, R., Lamballe, F., Bryant, S., and Barbacid, M. (1992) Neuron 8, 947–956

Klein, R., Parada, L. F., Coulier, F. and Barbacid, M. (1989), EMBO J., 8, 3701–3709

Knusel B, Beck K D, Winslow J W, Rosenthal A, Burton L E, Widmer H R, Nikolics K, Hefti F (1992) Brain-derived neurotrophic factor administration protects basal forebrain cholinergic but not nigral dopaminergic neurons from degenerative changes after axotomy in the adult rat brain. J Neurosci 12:4391–4402.

Koliatsos V E, Clatterbuck R E, Winslow J W, Cayouette M H, Price D L (1993) Evidence that brain-derived neurotrophic factor is a trophic factor for motor neurons in vivo. Neuron 10:359–367.

Konings P N M, Makkink W K, van Delft A M L, Ruigt G S F (1994) Reversal by NGF of cytostatic drug-induced reduction of neurite outgrowth in rat dorsal root ganglia in vitro. Brain Res 640:195–204.

Kopf-Maier P, Muhlhausen SK (1992) Changes in the cytoskeleton pattern of tumor cells by cisplatin in vitro. Chem. Biol Interact 82:295–316.

Korsching, S. (1993). The neurotrophic factor concept: A reexamination. *J. Neurosci.* 13:2739–2748.

Lamballe F, Klein R, Barbacid M (1991) trkC, a new member of the trk family of tyrosine protein kinase, is a receptor for neurotrophin-3. Cell 66:967–979.

Lambert P R (1994) Inner ear hair cell regeneration in a mammal: identification of a triggering factor. Laryngoscope 104:701–718.

Lärkfors L, Ebendal T, Lindsay R M, Alderson R F (1993) Effects of neurotrophins on rat embryonic cerebellar purkinje cells in vitro. Abstr. Soc. Neurosci. 19: A278.14.

Leake P A, Snyder R L, Hradek G T, Rebscher S J (1992) Chronic intracochlear electrical stimulation in neonatally deafened cats: effects of intensity and stimulating electrod location. Hear Res 64:99–117.

Lefebvre P P, Malgrange B, Staecher H, Moghadass M, Van De Water T R, Moonen G (1994) Neurotrophins affect survival and neuritogenesis by adult injured auditory neurons in vitro. NeuroReport 5:865–868.

Lefebvre, P. P., Malgrange, B., Staecker, H., Moonen, G. and Van De Water, T. R. (1993). Retinoic acid stimulates regeneration of mammalian auditory hair cells. *Science* 260:692–695.

Lefebvre, P. P., Van De Water, T. R., Represa, J., Liu, W., Bernd, P., Modlin, S., Moonen, G., and Mayer, M. B. (1991). Temporal pattern of nerve growth factor (NGF) binding in vivo and the in vitro effects of NGF on cultures of developing auditory and vestibular neurons. *Acta Otolaryngol (Stockh)* 111 :304–311.

Lefebvre P P, Malgrange B, Moonen G, Van De Water T R (1995) Response to: Regeneration and mammalian auditory hair cells. Science 267: 709–711.

Leibrock J, Lottspeich F, Hohn A, Hofer M, Hengerer B, Masiakowski P, Thoenen H, Barde Y A (1989) Molecular cloning and expression of brain-derived neurotrophic factor. Nature 341:149–152.

Levi-Montalcini R (1987) The nerve growth factor: thirty-five years later. EMBO J. 6:1145–1154.

Lim D J (1986) Effects of noise and ototoxic drugs at the cellular level in the cochlea: A review. Am J Otolaryngol 7: 73–99.

Lippe W R, Hathaway O, Parlotz D (1995) Loss of avian spiral ganglion neurons following aminoglycosie-induced hair cell loss and regeneration. Assoc Res Otolaryngol Abstr. p84.

Maisonpierre P C, Belluscio L, Squinto S, Ip N Y, Furth M E, Lindsay R M, Yancopoulos G D (1990) Neurotrophin-3: a neurotrophic factor related to NGF and BDNF. Science 247:1446–1451.

Martin-Zanca, D., Oskam, R., Mitra, G., Copeland, T. and Barbacid, M. (1989), Mol.Cell. Biol., 9, 24–33

McAlpine D, Johnstone B M (1990) The ototoxic mechanism of cisplatin. Hear Res 47:191–204.

McCabe P, Dey F (1965) The effects of aspirin upon auditory sensitivity. Ann Otol 74: 312–324.

Mollman J E (1990) Cisplatin neurotoxicity. N. Engl. J. Med. 322:126–127.

Myers E N, Berstaein J M (1965) Salicylate ototoxicity: A clinical and experimental study. Arch Otolaryngl Head Neck Surg 82: 483–493.

Nakai, Y., Konishi, K., Chang, K. C., Ohashi, K., Morisaki, N., Minowa, Y., and Morimoto, A. (1982). Ototoxicity of the anticancer drug cisplatin. *Acta Otolaryngol* 93:227–232.

Pirvola, U., Ylikoski, J., Palgi, J., Lehtonen, E., Arumae, U., and Saarma, M. (1992). Brain-derived neurotrophic factor and neurotrophin 3 mRNAs in the peripheral target fields of developing inner ear ganglia. Proc. Natl. Acad. Sci. USA 89:9915–9919.

Pryor G (1994) Assessment of auditory dysfunction. In Principle of Neurotoxicology. Chang L W, ed., Marcel Dekker, Inc. PP345–371.

Rastel D, Abdouh A, Dahl D, Roman R (1993) An original organotypic culture method to study the organ of Corti of the newborn rat in vitro. J Neurosci Methods 47:123–131.

Richardson G P, Russell I J (1991) Cochlear cultures as a model system for studying aminoglycoside ototoxicity. Hear Res 53:293–311.

Roelofs, R. I., Hrushesky, W., Rogin, J., and Rosenberg, L. (1984). Peripheral sensory neuropathy and cisplatin chemotherapy. *Neurology* 34:934–938.

Rosenthal A, Goeddel D, Nguyen T, Lewis M, Shih A, Laramee G R, Nikolics K, Winslow J W (1990) Primary structure and biological activity of a novel human neurotrophic factor. Neuron 4:767–773.

Rybak L P (1986) Ototoxic mechanisms. In: Neurobiology of Hearing. Altschuler R A, Bobbin R P, Hoffman D W, Eds. Raven Press (New York) PP441–454.

Schacht J (1986) Molecular mechanisms of drug-induced hearing loss. Hear Res 22: 297–304.

Schecterson, L. C., and Bothwell, M. (1994). Neurotrophin and neurotrophin receptor mRNA expression in developing inner ear. *Hear. Res.* 73:92–100.

Scopes, R., Protein Purification, Springer-Verlag, N.Y. (1982)

Sera, K., Harada, Y., Tagashira, N., Suzuki, M., Hirakawa, K., and Ohya, T. (1987). Morphological changes in the vestibular epithelia and ganglion induced by ototoxic drug. *Scanning Microsc.* 1:1191≈1197.

Shelton, D. L., Sutherland, J., Gripp, J., Camertato, T., Armanini, M. P., Phillips, H. S., Carroll, K., Spencer, S. D., and Levinson, A. D. (1995). Human trks: Molecular cloning, tissue distribution, and expression of extracellular domain immunoadhesins. *J Neurosci.* 15:477–491.

Siegal T, Haim N (1990) Cisplatin-induced peripheral neuropathy. Cancer 66:1117–1123.

Snider, W, D, (1994), Functions of the neurotrophins during nervous system development: What the knockouts are teaching us. *Cell* 77: 627–638.

Sobkowicz H M, Bereman B, Rose J E (1975) Organotypic develoment of the organ of Corti in culture. J. neurocytol. 4:543–572.

Soppet D, Escandon E, Maragos J, Middlemas D S, Reid S W, Blair J, Burton L E, Stanton B R, Kaplan D R, Hunter T, Nikolics K, Parada L F (1991) The neurotrophic factors brain-derived neurotrophic factor and neurotrophin-3 are ligands for the trkB tyrosine kinase receptor. Cell 65:895–903.

Squinto S P, Stitt T N, Aldrich T H, Davis S, Bianco S M, Radziejewski C, Glass D J, Masiakowski P, Furth M E, Valenzuela D M, DiStefano P S, Yancopoulos G D (1991) trkB encodes a functional receptor for brain-derived neurotrophic factor and neurotrophin-3 but not nerve growth factor. Cell 65:885-893.

Stadnicki, S. W., Fleischman, R. W., Schaeppi, U., and Merriam, P. (1975). Cis-dichlorodiammineplatinum (II) (NSC-119875): Hearing loss and other toxic effects in rhesus monkeys. *Cancer Chemother. Rep.* 59:467–480.

Thompson, S. W., Davis, L. E., Kornfeld, M., Hilgers, R. D., and Standefer, J. C. (1984). Cisplatin neuropathy. *Cancer* 54:12691–1275.

Tsoulfas P, Soppet D, Escandon E, Tessarollo L, Mendoza-Ramirez J-L, Rosenthal A, Nikolics K, Parada L F (1993) The rat trkC locus encodes multiple neurogenic receptors that exhibit differential response to neurotrophin-3 in PC12 cells. Neuron 10:975- 990.

Tsue T T, Oesterle E C, Rubel E W (1994a) Diffusible factors regulate hair cell regeneration in the avian inner ear. Proc Natl Acad. Sci USA 91:1584–1588.

Tsue T T, Oesterle E C, Rubel E W (1994b) Hair cell regeneration in the inner ear. Otolaryngol. HeadNeck Surg 111:281–301.

Valenzuela D M, Maisonpierre P C, Glass D J, Rojas E, Nunez L, Kong Y, Gies D R, Stitt T N, Ip N Y, Yancopoulos G D (1993) Alternative forms of rat trkC with different functional capabilities. Neuron 10: 963–974.

Vazquez E, Van De Water T R, Del Valle M, Veta J A, Staecker H, Giráldez F, Represa J (1994) Pattern of trkB protein-like immunoreactivity in vivo and the in vitro effects of brain-derived neurotrophic factor (BDNF) on developing cochlear and vestibular neurons. Anat. Embryol. 189:157–167.

Verdi, J. M., Birren, S. J., Ibanez, C. F., Persson, H., Kaplan, D. R., Benedett, M., Chao, M. V., and Anderson, D. J. (1994). p75$^{LNGFR}$ regulates trk signal transduction and NGF-induced neuronal differentiation in MAH cells. *Neuron* 12:7 on Bartheld, C. S., Patterson, S. L., Heuer, J. G., Wheeler, E. F., Bothwell, M., and Rubel, E. W. (1991). Expression of nerve growth factor (NGF) receptors in the developing inner ear of chick and rat. *Development* 113: 455–470.

Warchol, M. E., Lambert, P. R., Goldstein, B. J., Forge, A., and Corwin, J. T. (1993). Regenerative proliferation in inner ear sensory epithelia from adult Guinea pigs and humans. *Science* 259:1619–1622.

Weskamp, G., and Reichardt, L. F. (1991). Evidence that biological activity of NGF is mediated through a novel subclass of high affinity receptors. *Neuron* 6:649–663.

Wheeler, E. F., Bothwell, M., Schecterson, L. C., and Von Bartheld, C. S. (1994). Expression of BDNF and NT-3 mRNA in hair cells of the organ of corti: Quantitative analysis in developing rats. *Hear. Res.* 73:46–56.

Windebank A J, Smith A G, Russell J W (1994) The effect of nerve growth factor, ciliary neurotrophic factor, and ACTH analogs on cisplatin neurotoxicity in vitro. Neurology 44: 488–494.

Wittmaack K (1903) Beitrage zur Kenntnis der Wirkung des Chinins auf das Gehoerorgan. Pflueger Arch Ges Physiol 95:237.

Woodford C M, Henderson D, Hamernik R P (1978) Effects of combinations of sodium salicylate and noise on the auditory threshold. Ann Otol Rhinol Laryngol 87:117–127.

Yamashita H, Oesterle E C (1995) Induction of cell proliferation in mammalian inner-ear sensory epithelia by transforing growth factor a and epidermal growth factor. Proc Natl Acad Sci USA 92:3152–3155.

Yan Q, Elliott J L, Snider W D (1992) Brain-derived neurotrophic factor rescues spinal motoneurons from axotomy induced cell death. Nature 360:753–755.

Yan, Q., Matheson, C., Sun, J., Radeke, M. J., Feinstein, S. C., and Miller, J. A. (1994). Distribution of intracerebral ventricularly administered neurotrophins in rat brain and its correlation with trk receptor expression. *Exper. Neurology* 127:23–36.

Ylikoski, J., Pirvola, U., Moshnyakov, M., Palgi, J., Arumae, U., and Saarma, M. (1993). Expression patterns of neurotrophin and their receptor mRNAs in the rat inner ear. Hear. Res. 65:69–78.

What is claimed is:

1. A method for treating hearing impairment in a post-natal mammal, the method comprising administering to the mammal a therapeutically effective amount of a trkB or trkC agonist, wherein said hearing impairment is the result of neuronal damage.

2. The method of claim 1, wherein the agonist is selected from the group consisting of a neurotrophin, a chimeric neurotrophin, a pantrophic neurotrophin, a small molecule agonist and an antibody agonist or an antigen-binding fragment thereof.

3. The method of claim 2, wherein said neurotrophin is selected from the group consisting of NT-4/5, BDNF or NT-3.

4. The method of claim 3, wherein the neurotrophin is NT-4/5.

5. The method of claim 2, wherein said pantrophic neurotrophin is MNTS-1.

6. The method of claim 1, wherein said neuronal damage is damage to spiral ganglion neurons.

7. The method of claim 6 wherein said damage is caused by an ototoxic agent.

8. The method of claim 7, wherein the ototoxic agent is a pharmaceutical drug.

9. The method of claim 8, wherein said pharmaceutical drug is selected from the group consisting of an aminoglycoside antibiotic, a chemotherapeutic agent, a salicylate or salicylate-like compound, a loop diuretic, and a quinine or quinine-like compound.

10. The method of claim 9, wherein said aminoglycoside antibiotic is selected from the group consisting of neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin.

11. The method of claim 8, wherein the ototoxic agent is an anti-neoplastic drug.

12. The method of claim 11, wherein the ototoxic agent is cisplatin or a cisplatin-like compound.

13. The method of claim 1, wherein the trkB or trkC agonist is administered with an agent that promotes hair cell growth, proliferation, survival, or differentiation.

14. The method of claim 13 wherein said agent is retinoic acid or retinoic acid in combination with TGF-α.

15. The method of claim 1 further comprising administering a therapeutically effective amount of a further trkB or trkC agonist.

16. A method of treating damage to spiral ganglion neurons in a post-natal mammal, comprising administering to the mammal a therapeutically effective amount of a trkB or trkC agonist.

17. The method of claim 16 wherein the agonist is selected from the group consisting of a neurotrophin, a chimeric neurotrophin, a pantrophic neurotrophin, a small molecule agonist and an antibody agonist or an antigen-binding fragment thereof.

18. The method of claim 17, wherein said neurotrophin is selected from the group consisting of NT-4/5, BDNF and NT-3.

19. The method of claim 18 wherein said neurotrophin is NT-4/5.

20. The method of claim 17 wherein said pantrophic neurotrophin is MNTS-1.

21. The method of claim 16 wherein said damage to spiral ganglion neurons is caused by an ototoxic agent.

22. The method of claim 21, wherein said ototoxic agent is selected from the group consisting of an aminoglycoside antibiotic, a chemotherapeutic agent, a salicylate or salicylate-like compound, a loop diuretic, and a quinine or quinine-like compound.

23. The method of claim 22 wherein said aminoglycoside antibiotic is selected from the group consisting of neomycin, paromomycin, ribostamycin, lividomycin, kanamycin, amikacin, tobramycin, viomycin, gentamicin, sisomicin, netilmicin, streptomycin, dibekacin, fortimicin and dihydrostreptomycin.

24. The method of claim 21 wherein the ototoxic agent is an anti-neoplastic drug.

25. The method of claim 24 wherein the ototoxic agent is cisplatin or a cisplatin-like compound.

26. A method of preventing hearing impairment in a post-natal mammal comprising administering to the mammal a therapeutically effective amount of a trkB or trkC agonist, wherein it is known that said mammal will be exposed to an external factor that can injure spiral ganglion neurons.

27. The method of claim 26 wherein the agonist is selected from the group consisting of a neurotrophin, a chimeric neurotrophin, a pantrophic neurotrophin, a small molecule agonist and an antibody agonist or an antigen-binding fragment thereof.

28. The method of claim 27 wherein said neurotrophin is selected from the group consisting of NT-4/5, BDNF and NT-3.

29. The method of claim 28 wherein said neurotrophin is NT-4/5.

30. The method of claim 26 wherein said pantrophic neurotrophin is MNTS-1.

31. The method of claim 26 wherein said external factor is an ototoxic agent.

32. The method of claim 31 wherein said ototoxic agent is to be administered therapeutically to said mammal.

33. The method of claim 32 wherein the ototoxic agent is a pharmaceutical drug.

34. The method of claim 33, wherein said pharmaceutical drug is selected from the group consisting of an aminoglycoside antibiotic, a chemotherapeutic agent, a salicylate or salicylate-like compound, a loop diuretic and a quinine or quinine-like compound.

35. The method of claim 34 wherein said aminoglycoside antibiotic is selected from the group consisting of neomycin, paromomycin, ribostamycin, lividomycin, kanamycin, amikacin, tobramycin, viomycin, gentamicin, sisomicin, netilmicin, streptomycin, dibekacin, fortimicin and dihydrostreptomycin.

36. The method of claim 33 wherein the ototoxic agent is an anti-neoplastic drug.

37. The method of claim 36 wherein the ototoxic agent is cisplatin or a cisplatin-like compound.

38. The method of claim 26 wherein said external factor is administered to the mammal in combination with the agonist.

* * * * *